US010717964B2

(12) United States Patent
Papoutsakis et al.

(10) Patent No.: US 10,717,964 B2
(45) Date of Patent: *Jul. 21, 2020

(54) SYNTHETIC METHYLOTROPHY TO LIQUID FUELS AND CHEMICALS

(71) Applicant: University of Delaware, Newark, DE (US)

(72) Inventors: Eleftherios T. Papoutsakis, Newark, DE (US); Sergios Nicolaou, Larnaca (CY); Alan Fast, Newark, DE (US); Vasiliki Falara, Newark, DE (US); Robert Kyle Bennett, Elkton, MD (US); William Brian Whitaker, Newark, DE (US); Nicholas Richard Sandoval, Newark, DE (US); Jacqueline Gonzalez, Elkton, MD (US); Maciek Antoniewicz, Baltimore, MD (US)

(73) Assignee: University of Delaware, Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,257

(22) Filed: Jul. 23, 2018

(65) Prior Publication Data
US 2019/0048310 A1 Feb. 14, 2019

Related U.S. Application Data

(63) Continuation of application No. 15/112,364, filed as application No. PCT/US2015/010795 on Jan. 9, 2015, now Pat. No. 10,059,920.
(Continued)

(51) Int. Cl.
C12N 1/32 (2006.01)
C12P 7/16 (2006.01)
(Continued)

(52) U.S. Cl.
CPC ............. C12N 1/32 (2013.01); C12N 9/0006 (2013.01); C12N 9/88 (2013.01); C12N 9/90 (2013.01);
(Continued)

(58) Field of Classification Search
None
See application file for complete search history.

(56) References Cited

U.S. PATENT DOCUMENTS 8,178,327 B2    5/2012   Burk et al.
8,268,607 B2    9/2012   Burgard et al.
(Continued)

FOREIGN PATENT DOCUMENTS

WO    WO 2009/111513 A1    9/2009
WO    WO 2013/110797 A1    8/2013
(Continued)

OTHER PUBLICATIONS

UniProtKB—SwissProt Accession No. P42327.1, published Nov. 28, 2012.
(Continued)

Primary Examiner — Richard C Ekstrom
(74) Attorney, Agent, or Firm — RatnerPrestia

(57) ABSTRACT

A non-naturally occurring microbe capable of growing in a medium comprising methanol is provided. The methanol contributes to a significant percentage (e.g., at least 40%) of the carbon source for the non-naturally occurring microbe, which expresses heterologous methanol dehydrogenase (MDH) and heterologous ribulose monophosphate (RuMP) pathway enzymes. Methods for producing liquid fuels and chemicals by the non-naturally occurring microbe and methods for preparing the non-naturally occurring microbe are also provided.

19 Claims, 35 Drawing Sheets

Specification includes a Sequence Listing.

Related U.S. Application Data

(60) Provisional application No. 61/928,052, filed on Jan. 16, 2014, provisional application No. 61/979,058, filed on Apr. 14, 2014, provisional application No. 62/023,208, filed on Jul. 11, 2014, provisional application No. 62/061,731, filed on Oct. 9, 2014, provisional application No. 62/091,799, filed on Dec. 15, 2014.

(51) Int. Cl.

| | | |
|---|---|---|
| *C12P 7/40* | (2006.01) | |
| *C12P 7/42* | (2006.01) | |
| *C12P 7/44* | (2006.01) | |
| *C12P 7/46* | (2006.01) | |
| *C12P 7/62* | (2006.01) | |
| *C12N 9/04* | (2006.01) | |
| *C12N 9/88* | (2006.01) | |
| *C12N 9/90* | (2006.01) | |
| *C12N 15/52* | (2006.01) | |
| *C12N 15/70* | (2006.01) | |

(52) U.S. Cl.
CPC ............ *C12N 15/52* (2013.01); *C12N 15/70* (2013.01); *C12P 7/16* (2013.01); *C12P 7/40* (2013.01); *C12P 7/42* (2013.01); *C12P 7/44* (2013.01); *C12P 7/46* (2013.01); *C12P 7/625* (2013.01); *Y02E 50/10* (2013.01)

(56) References Cited

U.S. PATENT DOCUMENTS

| | | |
|---|---|---|
| 8,349,587 B2 | 1/2013 | Fischer et al. |
| 8,377,666 B2 | 2/2013 | Haselbeck et al. |
| 8,637,286 B2 | 1/2014 | Burgard et al. |
| 8,691,553 B2 | 4/2014 | Burk et al. |
| 8,697,421 B2 | 4/2014 | Burk et al. |
| 10,059,920 B2* | 8/2018 | Papoutsakis .............. C12N 1/32 |
| 2003/0104527 A1 | 6/2003 | Figueira et al. |
| 2003/0119155 A1 | 6/2003 | Yasueda et al. |
| 2004/0191875 A1 | 9/2004 | Takeshita et al. |
| 2009/0203070 A1 | 8/2009 | Devroe et al. |
| 2010/0279390 A1 | 11/2010 | Saphire |
| 2011/0016586 A1 | 1/2011 | Sanz Molinero et al. |
| 2013/0071883 A1* | 3/2013 | Burk .................. C12N 9/0008 435/92 |
| 2013/0145495 A1 | 6/2013 | Sayre |
| 2013/0330796 A1 | 12/2013 | Beck et al. |
| 2014/0147900 A1 | 5/2014 | Trawick et al. |
| 2014/0256011 A1 | 9/2014 | Zelle et al. |
| 2015/0337338 A1 | 11/2015 | Furutani et al. |

FOREIGN PATENT DOCUMENTS

| | | |
|---|---|---|
| WO | WO 2014/035925 A1 | 3/2014 |
| WO | WO 2014/071286 A1 | 5/2014 |

OTHER PUBLICATIONS

Brautaset et al., Journal Bacteriology, 186(5):1229-38 (2004).
Chu and Papoutsakis, Biotechnol. Bioeng., 29(1): 55-64 (1987).
Datsenko and Wanner, PNAS, 97(12):6640-45 (2000).
International Preliminary Report on Patentability for PCT/US2015/010795 dated Jul. 19, 2016.
Jakobsen et al., Journal Bacteriology, 188(8):3063-72 (2006).
Krog et al., PLOS One, 8(3):59188, pp. 1-10 (2013).
Nash, Biochemical Journal, 55:416-21 (1953).
PCT/US2015/010795 International Search Report issued by Blaine R. Copenheaver, dated May 6, 2015.
Rai et al., Bioresource Technology, pp. 1-5 (2017).
Gaida et al., Nature Communications, pp. 1-10 (2015).
Leßmeier et al., Appl Microbiol Biotechnol, 99:10163-76 (2015).
Mitsui et al., Applied Environmental Microbiology, 69(10):6128-32 (2003).
Müller et al., Metabolic Engineering, 28:190-201 (2015).
Orita et al., Appl Microbiol Biotechnol, 76:439-45 (2007).
Rohlhill et al., ACS Synthetic Biology, 6:1584-95 (2017).
Witthoff et al., Applied and Environmental Microbiology, 81(6):2215-25 (2015).

\* cited by examiner

FIG. 32A

```
ATGGTTAATCTGACGATCGACGGTCAACGTGTTACGGCGCCTGAGGGTATGACGATCTTGGAGGTT
GCGCGTGAGAACGGTATCCACATTCCAACGCTGTGTCATCACCCGAAACTGCGTCCGCTGGGCTACT
GTCGTCTGTGCCTGGTGGATATCGAGGGTGCAGCGAAGCCGATGACCGCGTGCAATACCCCGGTGG
CCGAGGGTATGGTGATTCGCACCAGCACCCCGGTGATCGAAGAGATGCGCAAGGGTATCATTGAGA
TGTTGCTGAGCCTGCATCCTGAGGACTGTCTGACGTGCGAAAAGGCGGGTAACTGTCAGCTGCAGG
ATTGTGCATATACGTACGGCGTAAAACATGGTGAGCTGCCGGTCAAGCGCGAAGAATTACCGGTGTT
GAAAGAAAACCCGTTTATCGTGCGTGATTACAACAAGTGTATTGTCTGTGGTCGTTGTGTGCGCGCG
TGCCAGGAAGTGCAAGTTCAGCGTGTTGTGGACCTGGTCGGTAAGGGTAGCGCGGCACGCGTCGG
CGCTACCAAGGCCGGTGCTGAAGTTAGCCTGGAAGAGGGCGGCTGCGTTTTCTGCGGCAATTGCGT
CCAAGTTTGTCCGGTGGGTGCGCTGACCGAGAAAGCCGGCCTGGGCCAGGGTCGTGAGTGGGAAT
TCAAAAAGTTCGCTCGATCTGTAGCTATTGCGGTGTGGGCTGCAATCTGACTCTGTACGTGAAGGA
CGGTAAAGTCGTTAAGGTTCGCGGTTATGAGAACCCGGAAGTAAACAACGGTTGGCTGTGTGTTAA
GGGCCGCTTCGGTTTTGATTACATTCACAACCCGGACCGTATTACGCGTCCGCTGATTCGCGAGGGC
GATCGTGAGAAAGGTTATTTCCGTGAGGCGTCCTGGGAAGAAGCGCTGGCCCTGGTGAGCCAGAAA
CTGACCCAAATCAAAGGTTCTTACGGTTCCGAAGCACTGGGTTTTCTGTGCAGCGCCAAGTGCACGA
ACGAAGAGAATTACCTGTTGCAAAAGTTAGCTCGTGGTGTGCTCGGTACCAATAACGTCGATCATTG
TGCACGCCTGTGACACTCTTCTACGGTTGCAGGTCTGCACCAAACGTTCGGCAGCGGTGCCATGA
CCAATAGCATCGCGGATATTGCGAGCGCGGACTGCATTTTTGTTATCGGTAGCAACACCACCGAAAA
TCACCCGGTTATTGCCCTGAAAGTCAAAGAGGCAGTCCGTCGTGGTGCGCGTCTGATCGTCGCGGA
TCCTCGCCGTATCGAGTTGGTCAATTTCAGCTATCTTTGGCTGCGCCAGAAGCCGGGTACCGACTTG
GCCCTGCTGAATGGCCTGTTGCACGTTATCATTAAAGAAGAACTGTACGATAAAGAATTCATCGCAC
AGCGTACCGAAGGCTTTGAGGCTTTGAAACTGGCAGTGGAAGAGTACACTCCGGCAAAAGTTTCCG
AGGTCACCGGTGTGCCGGCAGGCGACATTATCGAAGCGGCTCGCACCTATGCGCGTGGTCCATCCA
GCACCATTCTGTATGCGATGGGTATTACGCAACACATTACGGGCACCGCAAACGTGATGGCATTAGC
GAATCTGGCGATGGCGTGCGGCCAGGTTGGTAAGGAAGGCAACGGCGTCAACCCGCTGCGCGGTC
AATCAAACGTTCAGGGTGCGTGCGACATGGGTGGCCTGCCGAATGTCCTCCCGGGTTATCAACCGG
TTACCGACCCGGGTGTGCGTCACAAGTTCAGCGAAACTTGGGGTGTGCCGGATCTGCCGGGTGAGC
CAGGTCTGACGCTGATGGAGATGATGGCAGCGGCCCAGGAGGGCAAGTTGAAGGGTATGTATATCC
TGGGTGAAAACCCTGTTCTGACCGATCCAGACGTGAGCCATGTTAAAGAGGCCCTGAAGAACCTGG
AATTCTTGGTCGTCCAAGACATCTTTCTGACGGAAACCGCACGCATGGCTGATGTTGTGCTGCCGGG
TGCGAGCTTTGCGGAGAAAGAAGGCACCTTTACTTCCACCGAGCGTCGTGTGCAGCTGCTGCATAAA
GCAATTGAACCGCCTGGCGAGGCGCGTCCGGATTGGCTGATTCTGAATGACCTGTTGCTGTTGATG
GGCTATCCGCGCAAATACAGCAGCCCGGGTGAGATCATGCAAGAAATTGCGGGCCTGACCCCGAGC
TATGCGGGTATCACCTACGAGCGTCTGGAGGACAAGGGCCTGCAGTGGCCGGTTCTGAGCCTGGAG
CACCCGGGTACGCCGGTCCTGCACCGTGAGAAATTCAGCCGTGGCTACGGTCAGTTCCAAGTTGTC
CATTACCGTCCACCGGCAGAGGAACCGGACGAAGAGTACCCGTTTCTGTTTACCACCGGCCGTAACC
TGTACCACTATCACACCGTCATCTCGCGCAAGAGCCGCGGTTTGGAAGAAATGTGCCCAGCCCCGG
TTGTCGAGATTAATGATAACGATGCCGCTCGCCTGGGCATCCGTGAGGGCGAGATGATTGAGATTGT
GAGCCGTCGCGGTAAGGTCCGTGTTAAAGCGCTGGTGACCGACCGTATCCCTCGCGGCCAAGTGTT
TATGAATTTCCATTTCCACGAAGCGGCTGCCAATCTGCTGACGATTGCTGCGCTGGATCCGGTCGCT
AAGATTCCGATTATCAAACCGGTTCTGTAA (SEQ ID NO: 1)
```

FIG. 32B

ATGAAAATCGTTCTGGTGCTGTATGATGCCGGCAAACATGCGGCCGATGAAGAAAAACTGTACGGCT
GCACCGAAAACAAACTGGGTATCGCAAATTGGCTGAAAGATCAGGGCCACGAACTGATTACCACGA
GTGATAAAGAAGGTGAAACCAGCGAACTGGATAAACATATCCCGGATGCCGATATTATCATTACCAC
GCCGTTTCACCCGGCATATATTACGAAAGAACGCCTGGATAAAGCAAAAAACCTGAAACTGGTGGTT
GTGGCGGGCGTTGGTAGTGATCATATCGATCTGGATTACATTAACCAGACCGGCAAGAAAATTAGCG
TTCTGGAAGTGACGGGTAGCAATGTTGTGTCTGTGGCAGAACACGTTGTGATGACCATGCTGGTTCT
GGTGCGTAACTTTGTTCCGGCGCATGAACAGATCATTAATCACGATTGGGAAGTGGCAGCGATCGC
GAAAGATGCCTATGATATTGAAGGCAAAACCATCGCGACGATTGGCGCCGGTCGTATTGGTTACCGC
GTTCTGGAACGTCTGCTGCCGTTCAACCCGAAAGAACTGCTGTATTACGATTATCAGGCCCTGCCGA
AAGAAGCAGAAGAAAAAGTTGGCGCGCGTCGCGTGGAAAATATCGAAGAACTGGTGGCCCAGGCA
GATATTGTTACCGTGAACGCACCGCTGCATGCGGGCACGAAAGGTCTGATCAACAAAGAACTGCTG
AGTAAATTCAAGAAAGGCGCGTGGCTGGTTAATACCGCACGCGGTGCGATTTGTGTTGCCGAAGAT
GTTGCGGCAGCCCTGGAAAGCGGTCAGCTGCGTGGTTATGGCGGTGATGTGTGGTTCCCGCAGCC
GGCACCGAAAGATCATCCGTGGCGTGATATGCGCAACAAATATGGCGCCGGTAATGCAATGACCCC
GCACTACAGCGGTACCACGCTGGATGCGCAGACCCGCTATGCCGAAGGCACGAAAAACATTCTGGA
ATCTTTCTTTACCGGTAAATTCGATTACCGTCCGCAGGATATCATTCTGCTGAATGGCGAATATGTGA
CGAAAGCGTACGGTAAACACGATAAAAAATAA (SEQ ID NO: 2)

FIG. 32C (1)

CCGGTTTGCTGATAGTTTTCTTTACCACCAGCGCTTCTGAGTTACCCAGTTTTGACGCCAGCAAGAAG
ACTTCAATCGGCACCTGTTGGCTGGCTGCAACCGCTAACGGGCTGGAACCAAGGTTGCCGATTTGC
ACGTCGCCAGAAGCCAGCGCCCGCACGATGCTGGCTCCGCTGTCAAACTTACGCCAGTCCACGGTT
GCTCCGCTTTCTTTAGCAAAGGTGTTGTCGGCCTGAGCCACTTTCGCCGGTTCGGCTGAGGTTTGAT
ACGCCACGGTGACGTTCACCGCCTGTGCCTGAAAAGCGATGAATGCCAGTGCGGCAAGAAGTGTGT
TTCGCGATGAAATTGCCATGATTGTCTGCTCCCTGTCTTGTTATGGGAGCAGTATTCAGGAATAAAA
ACATTCATTAAAGAATTAGTCGTTATCGCACAGATGATTTTATTCTTAGCAAAAAAACGGTGATGCT
GCCAACTTACTGATTTAGTGTATGATGGTGTTTTTGAGGTGCTCCA**GTGGCTTCTGTTTCTATCAGC
TGTCCCTCCTGTTCAGCTACTGACGGGGTGGTGCGTAACGGCAAAAGCACCGCCGGACATCA
GCGCTATCTCTGCTCTCACTGCCGTAAAACATGGCAACTGCAGTTCACTTACACCGCTTCTCA
ACCCGGTACGCACCAGAAAATCATTGATATGGCCATGAATGGCGTTGGATGCCGGGCAACT
GCCCGCATTATGGGCGTTGGCCTCAACACGATTTTACGTCACTTAAAAAACTCAGGCCGCAG
TCGGTAA**CCTCGCGCATACAGCCGGGCAGTGACGTCATCGTCTGCGCGGAAATGGACGAACAGTG
GGGCTATGTCGGGGCTAAATCGCGCCAGCGCTGGCTGTTTTACGCGTATGACAGGCTCCGGAAGAC
GGTTGTTGCGCACGTATTCGGTGAACGCACTATGGCGACGCTGGGGCGTCTTATGAGCCTGATGTC
ACCCTTTGACGTGGTGATATGGATGACGGATGGCTGGCCGCTGTATGAATCCCGCCTGAAGGGAAA
GCTGCACGTAATCAGCAAGCGATATACGCAGCGAATTGAGCGGCATAACCTGAATCTGAGGCAGCA
CCTGGCACGGCTGGGACGGAAGTCGCTGTCGTTCTCAAAATCGGTGGAGCTGCATGACAAAGTCAT
CGGGCATTATCTGAACATAAAACACTATCAATAAGTTGGAGTCATTACCTAGAACGTAATTTACCTGC
CGGAACTTATTCACTCCGACAAGAACTTATCCGTACAGGAGATTAAAATGATAAAACGGACGTTATTA
GCGGCGGCCATTTTTAGCGCATTGCCCGCTTATGCCGGGTTAACTTCCATTACCGCGGGCTACGATT
TTACCGATTATTCTGGCGATCATGGCAACCGTAATTTAGCGTATGCTGAACTGGTGGCGAAAGTTGA
AAACGCAACGCTGCTTTTTAATCTTTCCCAGGGGCGTCGTGATTATGAAACTGAACATTTCAATGCCA
CTCGCGGTCAGGGTGCGGTCTGGTATAAATGGAATAACTGGCTGACAACCCGAACGGGTATTGCCT
TTGCGGATAATACGCCGGTCTTTGCCCGCCAGGATTTTCGTCAGGATATTAACCTGGCCCTGTTGCC
AAAAACGCTTTTCACGACCGGTTATCGCTACACTAAATATTACGATGATGTCGAAGTCGATGCCTGGC
AAGGCGGCGTATCACTCTATACTGGCCCGGTGATCACCAGCTACCGCTATACCCATTATGACTCCAG

FIG. 32C (2)

```
CGATGCAGGTGGTAGTTATAGCAATATGATTTCCGTGCGTCTGAATGACCCGCGCGGCACTGGTTAT
ACGCAACTATGGCTAAGCCGCGGAACAGGCGCTTACACCTATGACTGGACGCCAGAAACACGCTAC
GGCAGCATGAAGAGCGTCAGTCTGCAACGTATTCAACCGCTGACTGAGCAACTTAATCTCGGGCTGA
CGGCAGGTAAAGTGTGGTACGACACCCCAACCGATGATTATAACGGTCTGCAACTTGCAGCCCATCT
GACCTGGAAATTCTGATTCCTTCTGCCGCCCGCTATCCGGGGCGGCCTTCCCTGCCGATTAGCCCCC
CCCTTTCCTCTTTGTTTTCCGACCACATTCACCGGATAAATTTTATTCTCCAGTGTTATATACTATAGG
GGGGTATGCATTGAC*ATATAGCATACCCCCCTATAGTATATTGCGTGCAGATAATGAGGTGCG
AA*ATGCCCAGTACTCCGGAAGAGAAGAAAAAGGTCCTTACTCGAGTTCGTCGTATTCGAGGGCAGA
TTGATGCTCTGGAACGGTCGCTGGAGGGTGATGCCGAATGCCGTGCCATACTCCAACAGATCGCTG
CCGTTCGGGGCGCGGCTAATGGGCTGATGGCAGAAGTGCTTGAAAGCCATATCCGGGAAACGTTTG
ACCGAAATGACTGCTACAGCCGCGAAGTCAGCCAATCCGTTGACGACACTATTGAACTGGTTCGAGC
CTATCTTAAATAGCTGAATCTATTACCATATTGAGGAAGAGCGAGAGATGAAATCACGTGCTGCCG
TTGCATTTGCTCCCGGTAAACCGCTGGAAATCGTTGAAATTGACGTTGCACCACCGAAAAAA
GGTGAAGTGCTGATTAAAGTCACCCATACCGGCGTTTGCCATACCGACGCATTTACCCTCTCC
GGGGATGACCCGGAAGGTGTATTCCGGTGGTTCTCGGTCACGAAGGGGCCGGCGTTGTGG
TTGAAGTCGGTGAAGGCGTAACCAGCGTCAAACCTGGCGACCATGTGATCCCGCTTTACACC
GCGGAGTGCGGCGAGTGTGAGTTCTGTCGTTCTGGCAAAACTAACCTCTGTGTTGCGGTTCG
CGAAACCCAGGGTAAAGGCTTGATGCCAGACGGCACCACCGTTTTTCTTACAACGGGCAGC
CGCTTTATCACTACATGGGATGCTCAACATTCAGTGAATACACCGTGGTCGCGGAAGTGTCT
CTGGCCAAAATTAATCCAGAAGCAAACCATGAACACGTCTGCCTGCTGGGCTGTGGCGTGAC
CACCGGTATTGGCGCGGTGCACAACACAGCTAAAGTCCAGCCAGGTGATTCTGTTGCCGTGT
TTGGTCTTGGCGCGATTGGTCTGGCAGTGGTTCAGGGCGCGCGTCAGGCGAAAGCGGGACG
GATTATCGCTATCGATACCAACCCGAAGAAATTCGATCTGGCTCGTCGCTTCGGTGCTACCG
ACTGCATTAACCCGAATGACTACGACAAACCGATTAAAGATGTCCTGCTGGATATCAACAAA
TGGGGTATCGACCATACCTTTGAATGCATCGGTAACGTCAACGTGATGCGTGCGGCGCTGGA
AAGTGCGCACCGCGGCTGGGGTCAGTCGGTGATCATCGGGGTAGCAGGTGCCGGTCAGGAA
ATCTCCACCCGACCATTCCAGTTGGTCACCGGTCGCGTATGGAAAGGTTCCGCGTTTGGCGG
CGTGAAAGGTCGTTCCCAGTTACCGGGTATGGTTGAAGATGCGATGAAAGGTGATATCGATC
TGGAACCGTTTGTCACGCATACCATGAGCCTTGATGAAATTAATGACGCCTTCGACCTGATG
CATGAAGGCAAATCCATTCGAACCGTAATTCGTTACTGATTTCCCGCAGGTATACCCCGTCCAC
TTCAGACGGGGTTCTTAATACTCTCCCTGGGCAGCCGTCCGGGGGATTAACCGTGAGATAATGACTG
*ATGGAACTCATTGAAAAACATGCCAGCTTTGGCGGCTGGCAAAATGTGTATCGGCATTATTCCCAAT
CACTGAAATGTGAAATGAATGTCGGCGTCTATCTCCCACCAAAAGCCGCGAATGAAAAATTGCCGGT
GTTGTACTGGCTTTCAGGCCTGACTTGCAACGAGCAGAATTTCATTACTAAATCGGGGATGCAGCGT
TACGCGGCTGAGCACAACATTATTGTTGTTGCGCCGGACACCAGTCCGCGAGGCAGTCATGTCGCA
GATGCTGACCGTTACGATCTCGGGCAAGGTGCCGGGTTTTACCTGAACGCGACGCAAGCGCCGTGG
AATGAACATTACAAAATGTATGACTATATCCGCAACGAGCTGCCGGATTTAGTGATGCATCATTTTCC
GGCAACGGCCAAAAAGTCTATCTCTGGTCATTCTATGGGCGGGCTGGGCGCGCTGGTGCTGGCGTT
ACGTAACCCAGATGAATATGTCAGCGTCTCGGCGTTTTCGCCCATTGTCTCCCCATCGCAAGTGCCG
TGGGGACAGCAAGCCTTTGCTGCATATCTTGCTGAAAATAAAGATGCCTGGTTGGATTACGACCCGG
TGAGTCTTATTTCACAAGGTCAACGCGTTGCGGAAATCATGGTTGATCAGGGGTTGAGTGATGATTT
TTACGCAGAACAGCTGCGGACTCCAAATCTTGAAAAGATCTGCCAGGAGATGAATATCAAGACGTTA
ATCCGTTATCACGAGGGTTATGATCACAGCTATTATTTTGTCTCCAGTTTTATTGGCGAGCATATTGC
CTACCACGCCAATAAACTGAATATGCGTTGA*TAATAGTGCACGACTGCCGGATGCGGCGTGAAC
GCCTTATCCGGCCTACA*CTTCGCCCGTAAACCGTAGGAAGATCTGATTGGCAAACGCATCGCCGTA
CCGTTTATCTCTACCACCCAC (SEQ ID NO: 3)
```

FIG. 39A

Moorela FDH-A with Ecoli SECIS (2,682 nt, 894aa)

ATGGTTAACCTGACCATTGACGGACAAAGGGTTACGGCTCCAGAGGGCATGACCATCCTGGAGGTG
GCCCGGGAAAATGGTATCCATATCCCCACCCTGTGCCACCATCCAAAGTTGCGGCCCCTGGGGTATT
GCCGTCTGTGCCTGGTCGACATCGAGGGCGCCGCAAAACCCATGACGGCCTGCAATACGCCGGTCG
CCGAGGGTATGGTGATCCGGACCAGCACGCCTGTTATAGAGGAGATGCGCAAGGGTATTATTGAAA
TGCTTTTAAGCCTCCACCCGGAGGACTGCCTGACCTGCGAAAAAGCAGGTAACTGCCAGCTCCAGG
ATTGCGCCTACACTTACGGTGTAAAGCATGGCGAACTGCCAGTAAAACGCGAGGAATTGCCCGTTTT
GAAGGAAAATCCCTTCATTGTGCGGGATTATAATAAATGTATCGTTTGCGGCCGTTGCGTCCGCGCC
TGCCAGGAGGTGCAGGTCCAGAGGGTCGTGGACCTGGTGGGTAAAGGCAGCGCCGCCCGGGTGG
GGGCGACGAAGGCCGGAGCGGAAGTAAGCCTGGAAGAAGGGGGCTGCGTCTTTTGCGGTAACTGT
GTCCAGGTCTGCCCGGTGGGAGCTCTGACGGAGAAGGCCGGCCTGGGCCAGGGCCGCGAGTGGG
AGTTCAAAAAAGTCCGCAGTATTTGTTCTTACTGCGGCGTGGGTTGTAATCTCACCCTTTATGTAAAA
GATGGTAAGGTGGTAAAAGTTAGGGGTTACGAAAACCCTGAGGTAAACAACGGCTGGCTGTGCGTA
AAAGGCCGCTTTGGTTTTGACTATATTCACAATCCTGACAGGATAACCAGGCCGTTGATCCGGGAGG
GAGATAGGGAAAAAGGCTATTTCCGGGAGGCTTCCTGGGAAGAAGCTTTAGCCCTTGTATCCCAGA
AATTAACTCAGATTAAAGGCAGCTACGGCTCTGAAGCTCTGGGCTTTCTTTGTTCAGCTAAATGTACC
AATGAAGAGAATTATCTCTTACAAAAGCTGGCCCGGGGGTACTGGGCACCAATAATGTTGATCACT
GTGCTCGCCTTGACACAGCTCTACCGTAGCAGGTCTGCTCGCTACATTTGGAAGCGGTGCAATG
ACCAATTCTATCGCTGACATCGCCAGCGCAGATTGTATCTTTGTCATTGGCAGCAATACAACCGAGAA
CCATCCTGTTATTGCCCTTAAAGTAAAAGAAGCTGTCCGTCGTGGAGCCAGGCTCATTGTTGCTGAT
CCCCGGCGTATTGAACTGGTGAACTTCAGTTACTTGTGGTTAAGACAAAAACCCGGAACAGATCTTG
CTCTGCTGAATGGACTGCTTCATGTAATCATCAAGGAAGAGCTTTATGACAAAGAATTTATTGCCCAG
AGGACGGAAGGTTTTGAGGCTCTAAAACTTGCCGTAGAGGAGTATACACCAGCAAAGGTGTCAGAA
GTTACAGGTGTTCCGGCAGGCGATATTATCGAGGCAGCAAGGACTTATGCCCGGGGTCCGAGCTCT
ACTATTTTGTACGCAATGGGAATAACCCAGCATATAACTGGTACGGCCAACGTGATGGCCCTGGCCA
ACCTGGCCATGGCCTGTGGTCAGGTCGGTAAAGAAGGTAACGGCGTAAATCCCTGCGGGGGCAG
AGCAATGTCCAGGGTGCCTGCGATATGGGTGGATTACCCAATGTATTACCGGGATACCAACCAGTAA
CAGATCCGGGGGTTCGCCATAAATTTAGCGAAACCTGGGGGGTACCGGACTTACCCGGAGAACCTG
GCCTGACATTAATGGAGATGATGGCGGCAGCCCAAGAAGGCAAATTGAAAGGGATGTATATTTTAG
GAGAAACCCTGTCTTGACTGATCCAGATGTCTCCCATGTAAAAGAGGCGTTAAAGAACCTGGAGTT
TCTGGTGGTACAGGATATTTTTTTGACGGAGACAGCCAGGATGGCGGATGTTGTTTTACCTGGAGCT
TCCTTTGCGGAAAAGGAAGGTACCTTTACCAGTACGGAGCGCCGGGTGCAGCTTTTGCATAAAGCCA
TTGAACCTCCCGGTGAAGCACGGCCGGATTGGCTTATTTTAAACGATTTGTTGCTGTTAATGGGATAT
CCGCGGAAATATTCGTCGCCTGGGGAGATAATGCAGGAGATAGCAGGGTTAACTCCCAGCTATGCG
GGTATAACTTATGAGCGCCTGGAAGATAAAGGGTTACAGTGGCCGGTGCTTTCCCTCGAACATCCGG
GTACACCCGTTCTCCATCGGGAAAAATTTAGCAGAGGTTATGGGCAGTTCCAGGTAGTGCATTACCG
GCCGCCGGCCGAAGAACCTGATGAAGAGTACCCGTTCTTATTTACCACTGGCAGGAATTTGTATCAC
TATCATACTGTTATTTCCCGTAAGTCCAGGGGGCTGGAAGAGATGTGTCCTGCTCCTGTGGTGGAGA
TTAATGATAACGATGCAGCCCGTTTGGGTATACGGGAAGGAGAAATGATTGAGATTGTTTCCCGACG
TGGTAAAGTAAGGGTTAAAGCATTGGTTACGGATCGCATACCCCGGGGCCAGGTATTTATGAATTTC
CATTTCCATGAAGCAGCAGCCAACCTGCTTACAATTGCTGCCCTGGATCCGGTTGCTAAAATACCGA
TTATAAAACCTGTGCTGTAG (SEQ ID NO: 8)

FIG. 39B

Optimized recombinant *M. thermoacetica* FDH-A

ATGCTGATTCGCCGCTTCCGTGCTTGTCCGCGTGATCGTACGCAACGTCGTGATACCGCTCTGGGTG
AAGTCGTCTTTTCAACCTGGGGTGGCAAAGTGGTTGATCATCGCGGCGGTCCGAGTGGCGGTGGCC
CGTCCTGGGCGGGTGAATTTGGTGGCCGTCAGCTGAAAGCCTTCATTGGCTGGGACGGTCTGGTCG
TGACGGATCCGGCAGTGGACCTGCTGGCAGCACTGCAAGCTTATTACCAGGCGGTTCAAGGCGAAA
GCTGCGGTCGCTGTGTGCCGTGCCGTGTTGGCACCCGTGTCATTTATAACGTGCTGGTTCGTATCGC
AGGTGGCGAAGGTCTGCCGAGCGATCTGGACCTGCTGCGTCGCGTGGCGTGGATCGTTCGCGATG
GCTCTCTGTGCGAACTGGGCCAGGCAGGTGCTAAAGCGGTGCTGGATTTTCTGGACTATTACAGCG
AAGCACTGCGCCCGTTCCTGGAAGATTCTGGCCGTGTTGCGGGTGGCCAGCGTCGCCCGGGTCCG
GGTGGCCGTGTCCAAGTGCTGGCATCAGGTCGTGTTCTGGTCGGTAATGATCGTGGTAAAGGTGCA
GCTGCAGCATCGCCGGCAGCTGGTCTGACCTATAAACCGTTTGTGACGGCACCGTGTCTGAAACGTT
GCCCGGCACATCTGGATATTCCGGCCTATATTGATGCAATCAAAGACGGTCGTTACGAAGAATCCCT
GGCGATTATCCGTCAGCGTACCGCACTGGCAGGCGTGCTGGGTCGCGTGTGTGTTCACCCGTGCGA
AGAAAACTGTCGTCGCGGCAATGTTGATGAACCGCTGGCAATCCGCGGTCTGAAACGTTTTGTCGCT
GACTACGAAGTGAAACGTGGTCGTCGCCCGGTCGCAGTGTGTGGTGGCAACCTGTTCACCGGTCCG
TGGCGTCCGGCTGGTCAGGCGGGTGGCGAAGAAACCACGGCTGTTACGTCAGGCAAGAAAGTGGC
GATTATCGGTGCAGGTCCGGCAGGTCTGTCGGCAGCATATCAACTGGCAGGTCGCGGTTACAAAGT
GACCATTTTTGAAGCTCTGCCGGTCGCGGGTGGCATGCTGGCAGTGGGTATTCCGAGTTATCGCCT
GCCGCGTGATATCCTGGCCGGCGAAATTGAAGCTATCAAAGCGCTGGGTGTGACCATCAACCTGAA
TACGCGCGTTGGCGTCGATGTGACCATGGACCAGCTGCAACGTGATTATGACGCCGTTTTCATTGCA
ACGGGTCTGCATGCTAGCTCTCGTATGGGCGTGGCGGGTGAAGATGAAGGCTACGGTGGCTTTATC
CCGGGTGTTAAATTCCTGCGCGATCTGAACCTGGACCGTTGCCCGTCTCTGGAAGGCAAAGTTGTCG
CCGTGGTTGGTGGCGGTAATGTGGCAATGGATTGTGCACGTAGTGCACTGCGTCGCGGTGCCCGTG
AAGTTCATCTGATTTATCGTCGCTCCCGCGCAGAAATGCCGGCTCACGCAACCGAAGTGCGTGATGC
CGAAGCAGAAGGCGTGATTTACCACTTTCTGGTTAACCCGACGGCTCTGGTCGCGGAAAAAGGCAA
TATCAAGGGTATGCAGTGCGTTCGTATGAAACTGGGTGAACCGGATGACAGCGGTCGTCGCCGTCC
GGTTCCGGTCCCGGGTACCGAATTTTTCCTGCCGTGTGATATTGTCGTGCCGGCGATCGGCCAAGCA
GCTGATCTGTCTTTTCTGGACGGTCGCATTGAAGTGGGCAAACGTGGTACCATCTCAGTCGATCCGG
TGACCCTGGCTACGTCGGTTCCGGGCGTCTTCGCGGGCGGTGACATTGTTCTGGGTGCCCGCACGG
TTGTCGAAGCTGTTGCACAGGGTAATCGTGCAGCAGTCAGTATCGATCAGTATCTGCGTCAAGGTAC
CACGTCCCGACCGTGGAAGATGAACTGGACGCCTGGCTGGAAAAAGTGGGCGTTTATGATCCGGA
AGAAGACGTCGGTATTTACGGCGGTCGTCCGCGTCAGGCAGAACGTGTGGCACCGCTGGCAGAAC
GCGTGAAAGATTTTCGTGAAGTTGAAGGCGGTTTTGACTTCTACGCGGGCCGCGCCGAAGCAGAAC
GTTGCCTGCGTTGTTATCGTGTCGGTATGATGGTGCTGGCGGGCGAAGGCGAATCCAATGGCTGA
(SEQ ID NO: 9)

FIG. 39C

Optimized *M. thermoacetica* FDH-B

```
ATGCTGATTCGCCGCTTCCGTGCTTGTCCGCGTGATCGTACGCAACGTCGTGATACCGCTCTGGGTG
AAGTCGTCTTTTCAACCTGGGGTGGCAAAGTGGTTGATCATCGCGGCGGTCCGAGTGGCGGTGGCC
CGTCCTGGGCGGGTGAATTTGGTGGCCGTCAGCTGAAAGCCTTCATTGGCTGGGACGGTCTGGTCG
TGACGGATCCGGCAGTGGACCTGCTGGCAGCACTGCAAGCTTATTACCAGGCGGTTCAAGGCGAAA
GCTGCGGTCGCTGTGTGCCGTGCCGTGTTGGCACCCGTGTCATTTATAACGTGCTGGTTCGTATCGC
AGGTGGCGAAGGTCTGCCGAGCGATCTGGACCTGCTGCGTCGCGTGGCGTGGATCGTTCGCGATG
GCTCTCTGTGCGAACTGGGCCAGGCAGGTGCTAAAGCGGTGCTGGATTTTCTGGACTATTACAGCG
AAGCACTGCGCCCGTTCCTGGAAGATTCTGGCCGTGTTGCGGGTGGCCAGCGTCGCCCGGGTCCG
GGTGGCCGTGTCCAAGTGCTGGCATCAGGTCGTGTTCTGGTCGGTAATGATCGTGGTAAAGGTGCA
GCTGCAGCATCGCCGGCAGCTGGTCTGACCTATAAACCGTTTGTGACGGCACCGTGTCTGAAACGTT
GCCCGGCACATCTGGATATTCCGGCCTATATTGATGCAATCAAAGACGGTCGTTACGAAGAATCCCT
GGCGATTATCCGTCAGCGTACCGCACTGGCAGGCGTGCTGGGTCGCGTGTGTGTTCACCCGTGCGA
AGAAAACTGTCGTCGCGGCAATGTTGATGAACCGCTGGCAATCCGCGGTCTGAAACGTTTTGTCGCT
GACTACGAAGTGAAACGTGGTCGTCGCCCGGTCGCAGTGTGTGGTGGCAACCTGTTCACCGGTCCG
TGGCGTCCGGCTGGTCAGGCGGGTGGCGAAGAAACCACGGCTGTTACGTCAGGCAAGAAAGTGGC
GATTATCGGTGCAGGTCCGGCAGGTCTGTCGGCAGCATATCAACTGGCAGGTCGCGGTTACAAAGT
GACCATTTTTGAAGCTCTGCCGGTCGCGGGTGGCATGCTGGCAGTGGGTATTCCGAGTTATCGCCT
GCCGCGTGATATCCTGGCCGGCGAAATTGAAGCTATCAAAGCGCTGGGTGTGACCATCAACCTGAA
TACGCGCGTTGGCGTCGATGTGACCATGGACCAGCTGCAACGTGATTATGACGCCGTTTTCATTGCA
ACGGGTCTGCATGCTAGCTCTCGTATGGGCGTGGCGGGTGAAGATGAAGGCTACGGTGGCTTTATC
CCGGGTGTTAAATTCCTGCGCGATCTGAACCTGGACCGTTGCCCGTCTCTGGAAGGCAAAGTTGTCG
CCGTGGTTGGTGGCGGTAATGTGGCAATGGATTGTGCACGTAGTGCACTGCGTCGCGGTGCCCGTG
AAGTTCATCTGATTTATCGTCGCTCCCGCGCAGAAATGCCGGCTCACGCAACCGAAGTGCGTGATGC
CGAAGCAGAAGGCGTGATTTACCACTTTCTGGTTAACCCGACGGCTCTGGTCGCGGAAAAAGGCAA
TATCAAGGGTATGCAGTGCGTTCGTATGAAACTGGGTGAACCGGATGACAGCGGTCGTCGCCGTCC
GGTTCCGGTCCCGGGTACCGAATTTTTCCTGCCGTGTGATATTGTCGTGCCGGCGATCGGCCAAGCA
GCTGATCTGTCTTTTCTGGACGGTCGCATTGAAGTGGGCAAACGTGGTACCATCTCAGTCGATCCGG
TGACCCTGGCTACGTCGGTTCCGGGCGTCTTCGCGGGCGGTGACATTGTTCTGGGTGCCCGCACGG
TTGTCGAAGCTGTTGCACAGGGTAATCGTGCAGCAGTCAGTATCGATCAGTATCTGCGTCAAGGTAC
CACGTCCCCGACCGTGGAAGATGAACTGGACGCCTGGCTGGAAAAAGTGGGCGTTTATGATCCGGA
AGAAGACGTCGGTATTTACGGCGGTCGTCCGCGTCAGGCAGAACGTGTGGCACCGCTGGCAGAAC
GCGTGAAAGATTTTCGTGAAGTTGAAGGCGGTTTTGACTTCTACGCGGGCCGCGCCGAAGCAGAAC
GTTGCCTGCGTTGTTATCGTGTCGGTATGATGGTGCTGGCGGGCGAAGGCGAATCCAATGGCTGA
(SEQ ID NO: 10)
```

SYNTHETIC METHYLOTROPHY TO LIQUID FUELS AND CHEMICALS

CROSS-REFERENCE TO RELATED APPLICATION

This application is a continuation application of U.S. application Ser. No. 15/112,364, filed Jul. 18, 2016, which claims the benefit of U.S. national phase application of International Application No. PCT/US2015/010795, filed Jan. 9, 2015, claiming the benefit of U.S. Provisional Application No. 61/928,052, filed Jan. 16, 2014, U.S. Provisional Application No. 61/979,058, filed Apr. 14, 2014, U.S. Provisional Application No. 62/023,208, filed Jul. 11, 2014, U.S. Provisional Application No. 62/061,731, filed Oct. 9, 2014, and U.S. Provisional Application No. 62/091,799, filed Dec. 15, 2014, the contents of each of which are incorporated herein by reference in their entireties for all purposes.

REFERENCE TO U.S. GOVERNMENT SUPPORT

This invention was made with government support under Award No. DE-AR0000432 the U.S. Advanced Research Projects Agency-Energy (ARPA-E) of is Department of Energy (DOE). The United States has certain rights in the invention.

FIELD OF THE INVENTION

The invention relates generally to non-naturally occurring microbes expressing heterologous genes required for growing in a medium comprising methanol, and the uses thereof for producing desirable liquid fuels and chemicals.

BACKGROUND OF THE INVENTION

Natural gas consists primarily of methane ($CH_4$), and includes smaller amounts of higher alkanes, $CO_2$, $N_2$, and $H_2S$. It is used not only for heating and energy generation, but also as a chemical feedstock to produce commodity chemicals that can be then converted to plastics and specialty chemicals. Natural gas constitutes an enormous energy and chemical resource for the US where the recoverable amount is estimated to be 2,000 trillion $ft^3$. Natural gas is however a poor transportation fuel because of its inherently low energy density. Technologies that can convert natural gas into liquid fuels at competitive prices will not only lessen our dependence on imported oil, but also eliminate the needs for retrofitting existing transportation infrastructure. Current chemical routes based on chemical conversion to syngas (CO & $H_2$) through the Fischer-Tropsch process are not competitive for producing liquid fuels, as they suffer from both high capital costs and low conversion efficiencies. Bioconversion is a promising alternative because of its high specificity and high process energy efficiency all under very mild conditions. Thus, $CH_4$ represents an ideal target for conversion to liquid fuels by biological processes or hybrid biological/catalytic processes.

While there has been some progresses made in the catalytic conversion of $CH_4$ to methanol (MeOH), more biological means may be developed for converting methane to methanol, likely by a form of reverse methanogenesis. There remains a need for non-naturally occurring methylotrophic microbes capable of converting methanol efficiently to liquid fuel molecules or other commodity chemicals.

SUMMARY OF THE INVENTION

The present invention relates to non-naturally occurring methylotrophic microbes and methods for use or preparation thereof.

A non-naturally occurring microbe capable of growing in a medium comprising methanol is provided. The methanol contributes to at least 40% of the carbon source for the non-naturally occurring microbe. The non-naturally occurring microbe expresses heterologous methanol dehydrogenase (MDH) and one or more heterologous ribulose monophosphate (RuMP) pathway enzymes. The expression of the one or more RuMP pathway enzymes may be under the control of a formaldehyde responsive promoter. The non-naturally occurring microbe may express heterologous MDH, heterologous 3-hexulose-6-phosphate synthase (HPS), and heterologous 3-hexulose-6-phosphate isomerase (PHI). The non-naturally occurring microbe may contain a deletion of a frmRAB operon.

The non-naturally occurring microbe may further express one or more heterologous pentose-phosphate pathway (PPP) enzymes. The expression of the one or more heterologous PPP enzymes may be under the control of a formaldehyde responsive promoter. The non-naturally occurring microbe may express heterologous phosphofructokinase (PFK), heterologous fructose bisphosphate aldolase (FBA), heterologous transketolase (TKT), heterologous fructose/sedoheptulose biphosphatase (GLPX), heterologous transaldolase (TAL), heterologous ribose-5-phospate (RPI) and heterologous ribulose phosphate epimerase (RPE).

The non-naturally occurring microbe may further express one or more heterologous cyclic formaldehyde dissimilation enzymes. The expression of the one or more heterologous cyclic formaldehyde dissimilation enzymes may be under the control of a formaldehyde responsive promoter. The non-naturally occurring microbe may express heterologous glucose-6-phosphate isomerase (PGI), glucose-6-phosphate-1-dehydrogenase (ZWF), 6-phosphogluconolactonase (PGL), and 6-phosphogluconate dehydrogenase (GND). The non-naturally occurring microbe may contain a deletion of a phosphogluconate dehydratase gene (edd).

The non-naturally occurring microbe may further express one or more heterologous $CO_2$ fixation pathway enzymes. The expression of the one or more heterologous $CO_2$ fixation pathway enzymes may be under the control of a formaldehyde responsive promoter. The non-naturally occurring microbe may express heterologous carbonic anhydrase (CA), heterologous formate dehydrogenase (FDH), and heterologous formaldehyde dehydrogenase (FLD).

The non-naturally occurring microbe may further express heterologous dihydroxyacetone synthase (DHAS) and heterologous dihydroxyacetone kinase (DAK).

The non-naturally occurring microbe may be derived from a microbe selected from the group consisting of facultative aerobic organisms, facultative anaerobic organisms, and anaerobic organisms. The non-naturally occurring microbe may be derived from a microbe selected from the group consisting of phyla Proteobacteria, Firmicutes, Actinobacteria, Cyanobacteria, Chlorobi, and *Deinococcus-Thermus*. The non-naturally occurring microbe may be derived from a microbe selected from the group consisting of *Escherichia, Bacillus, Clostridium, Enterobacter, Klebsiella, Enterobacteria, Mannheimia, Pseudomonas, Acinetobacter, Shewanella, Ralstonia, Geobacter, Zymomonas,*

*Acetobacter, Geobacillus, Lactococcus, Streptococcus, Lactobacillus, Corynebacterium, Streptomyces, Propionibacterium, Synechocystis, Synechococcus, Cyanobacteria, Chlorobi*, and *Deinococcus*. The non-naturally occurring microbe is preferably *E. coli*.

A method for producing a metabolite is also provided. The production method comprises growing a non-naturally occurring microbe of the present invention in a medium comprising methanol. The methanol contributes to at least 40% of the carbon source for the non-naturally occurring microbe.

The metabolite may be selected from the group consisting of 4-carbon chemicals, diacids, 3-carbon chemicals, higher carboxylic acids, alcohols of higher carboxylic acids, and polyhydroxyalkanoates. Preferably, the metabolite is n-butanol. At least 40% of the carbon in the metabolite may be derived from the methanol. The metabolite may be an amino acid or tricarboxylic acid (TCA) intermediate having a carbon at the fourth position derived from the methanol.

The production method may further comprise modifying the heterologous MDH or any one of the one or more heterologous RuMP pathway enzymes such that the production of the metabolite is improved. The production method may further comprise fixing $CO_2$.

According to the production method, the non-naturally occurring microbe may be grown at a temperature higher than 37° C. The non-naturally occurring microbe may be grown anaerobically.

A method for making a non-naturally occurring microbe capable of growing in a medium comprising methanol is further provided. The methanol contributes to at least 40% of the carbon source for the non-naturally occurring microbe. The preparation method comprises expressing heterologous methanol dehydrogenase (MDH) and one or more heterologous ribulose monophosophate (RuMP) pathway enzymes in a non-methylotrophic microbe. The non-naturally occurring microbe may express the heterologous MDH, heterologous 3-hexulose-6-phosphate synthase (HPS), and heterologous 3-hexulose-6-phosphate isomerase (PHI).

The preparation method may further comprise expressing one or more heterologous pentose-phosphate pathway (PPP) enzymes in the non-methylotrophic microbe. The non-methylotrophic microbe may express heterologous phosphofructokinase (PFK), heterologous fructose bisphosphate aldolase (FBA), heterologous transketolase (TKT), transaldolase (TAL), heterologous fructose/sedoheptulose biphosphatase (GLPX), heterologous ribose-5-phosphate (RPI), and heterologous ribulose phosphate epimerase (RPE).

The preparation method may further comprise expressing one or more heterologous cyclic formaldehyde dissimilation enzymes. The non-methylotrophic microbe may express heterologous glucose-6-phosphate isomerase (PGI), glucose-6-phosphate-1-dehydrogenase (ZWF), 6-phosphogluconolactonase (PGL), and 6-phosphogluconate dehydrogenase (GND).

The preparation method may further comprise expressing one or more heterologous $CO_2$ fixation pathway enzymes in the non-methylotrophic microbe. The non-methylotrophic microbe may express heterologous carbonic anhydrase (CA), heterologous formate dehydrogenase (FDH), and heterologous formaldehyde dehydrogenase (FLD).

The preparation method may further comprise expressing heterologous dihydroxyacetone synthase (DHAS) and dihydroxyacetone kinase (DAK).

BRIEF DESCRIPTION OF THE DRAWINGS

FIGS. 32A-C shows A) the final optimized sequence (SEQ ID NO: 1) for higher expression levels of the Moth FDH-A in *E. coli* with the artificially designed SECIS element designed by DNA2.0, including Selenocysteine codon (bold), Moth FDH-A native sequence (underlined) and *E. coli* SECIS optimized sequence (bold and italic), B) optimized sequence designed by Genscript (SEQ ID NO: 2), and C) the frmRAB operon (SEQ ID NO: 3) in *E. coli* BL21 (DE3), including frmR (underlined), frmA (bold), frmB (underlined and italic), upstream gene of frmR (underlined and bold), and the regions adjacent to the frmAB operon (bold and italic) to design primers.

FIGS. 39A-C shows A) *Moorela* FDH-A sequence with *E. coli* SECIS (2,682 nt, 894aa) (SEQ ID NO: 8), including Selenocysteine codon (bold), *Moorela* native sequence (underlined) and *E. coli* sequence for *E. coli* SECIS optimization (bold and italic), B) optimized recombinant *M. thermoacetica* FDH-A (SEQ ID NO: 9), and C) optimized *M. thermoacetica* FDH-B (SEQ ID NO: 10).

DETAILED DESCRIPTION OF THE INVENTION

The present invention relates to engineering *E. coli* or other microbes that do not naturally grow on or metabolize methanol to become methylotrophic, that is, capable of using methanol for growth as a sole substrate or co-substrate together with various carbohydrates or other carbon and energy substrates. The resulting non-naturally occurring microbes are capable of using the reduction energy from methanol utilization to fix $CO_2$, and produce liquid fuel and chemicals. This technology integrates all critical components required for achieving the overall goal of cost-efficient biofuel production starting from methanol (but ultimately $CH_4$) while at the same time minimizing $CO_2$ release.

Figure 1:
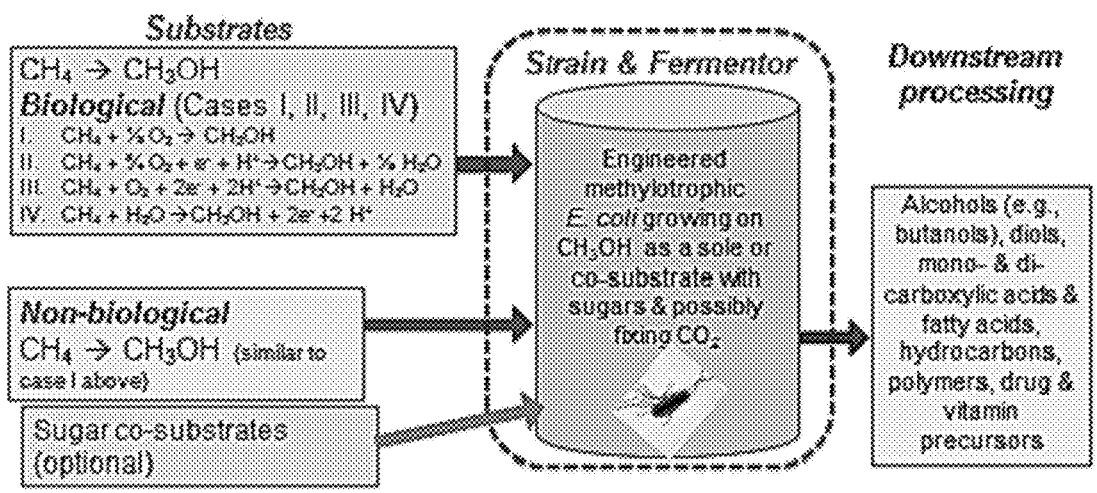
FIG. 1 illustrates an overview of the invention. Engineered and optimized *E. coli* can grow on methanol (MeOH), fix $CO_2$ & produce various chemicals (such as n-butanol (n-BuOH)). We assume MeOH will be generated biologically or non-biologically from $CH_4$ with the shown electrons needs/outputs.
Figure 2:
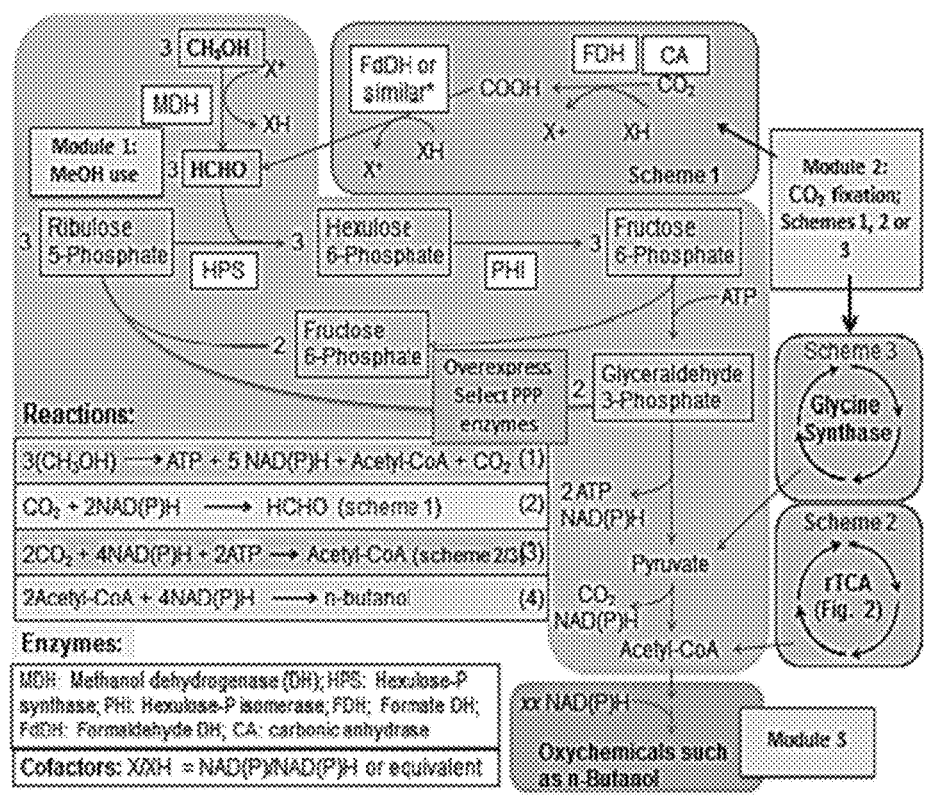
FIG. 2 illustrates pathways in an engineered *E. coli* strain that grows on MeOH, fixes $CO_2$ and produces n-butanol (n-BuOH) or another desirable chemical through a pathway that departs either from pyruvate or acetyl-CoA. Metabolic Engineering modules: 1 for MeOH use; 2 for $CO_2$ fixation; 3 for production of various oxychemicals (such as n-BuOH) from intermediates such as acetyl-CoA or pyruvate, but also others in the core cellular pathways.

Methanol (MeOH) utilization (FIG. 1 and Module 1 in FIG. 2) and $CO_2$ fixation (Module 2 in FIG. 2) may take place simultaneously to produce various chemicals and fuel molecules, for example, n-butanol (n-BuOH; FIGS. 1 & 2) from acetyl co-A or pyruvate or other intermediates of glycolysis, the TCA (tricarboxylic acid) cycle and related core pathways of the cells. The reduction energy contained in MeOH, which is more reduced than certain sugars, e.g., glucose (see reaction 1 of FIG. 2) may be conserved under anaerobic growth conditions and used to produce various oxygenated molecules such as BuOH and at the same time fix $CO_2$. To achieve this, genes/enzymes for the 3 modules, i.e., MeOH utilization, $CO_2$ fixation, and product formation (e.g., n-BuOH formation) (FIG. 2), are assembled in a microbe. Each of these goals may be carried out efficiently, and assessed for effectiveness of outcomes by different methods, for example, in terms of rates of MeOH and $CO_2$ utilization, carbon fluxes to pyruvate or acetyl-CoA, and the engineered pathway to produce the desirable product such as n-BuOH (FIG. 2).

The present invention provides an approach to simultaneously use MeOH and $CO_2$ to produce n-butanol (n-BuOH) (FIG. 2) or other chemicals starting with acetyl-CoA, pyruvate, or other intermediate metabolites (or chemicals) of the glycolysis pathway or pentose phosphate pathway, including but not limited to D-xylulose 5-phosphate, D-glyceraldehyde 3-phosphate and/or glycerone. This may be achieved by leveraging genes from methylotrophs for MeOH utilization (Module 1), and various natural or synthetic pathways for $CO_2$ fixation (Module 2) using genes from acetogens and other organisms. Synthetic methylotrophic strains may be engineered by combining these two modules with natural or synthetic pathways to produce a chemical or biofuel, such as for n-BuOH production (Module 3). Exemplary chemicals include 2, 3, 4, 5 and 6 carbon alcohols, carboxylic acids, ketones, aldehydes and di-acids.

Methanol may be used as a carbon source by conversion to formaldehyde (HCHO) by a MeOH dehydrogenase (MDH). HCHO may then be converted to hexulose-6-phosphate, using ribulose-5-phosphate, by a 3-hexulose-6-phosphate synthase (HPS). 3-Hexulose-6-phosphate isomerase (PHI) may convert the hexulose-6-phosphate to fructose-6-phosphate, which may then be used for generation of pyruvate and subsequently acetyl-CoA that may be the starting chemical to feed carbon skeletons into various synthetic pathways to produce various oxychemicals in, for example, the n-BuOH producing pathway (FIG. 2, module 3).

*E. coli* or the other microbes may be engineered to utilize MeOH as a carbon and energy source by expressing a MeOH dehydrogenase (MDH) and enzymes from the methylotrophic RuMP pathway (e.g., HPS and PHI, FIG. 2). Expression of additional pentose-phosphate pathway (PPP) enzymes as an additional inventive step and strategies including suitable expression promoters may be used to enable or enhance the expression of the corresponding genes in cells when exposed to methanol and/or formaldehyde as substrates.

Significantly, the present invention provides additional steps to make possible the recycling of all or most evolved $CO_2$ from the decarboxylation of pyruvate to acetyl-CoA (FIG. 2) aiming to minimize $CO_2$ formation. This can be executed for other biological systems independent of MeOH utilization as long as the cells use a carbon substrate that generates sufficient electrons available for $CO_2$ fixation and also as long as the cells can incorporate formaldehyde into metabolic intermediates. The engineered methylotrophic *E. coli* or other microbes may be generated for high pathway energy efficiency, yield, and kinetics.

The terms "protein" and "polypeptide" are used herein interchangeably, and refer to a polymer of amino acid residues with no limitation with respect to the minimum length of the polymer. Preferably, the protein or polypeptide has at least 20 amino acids. The definition includes both full-length proteins and fragments thereof, as well as modifications thereof (e.g., glycosylation, phosphorylation, deletions, additions and substitutions). The protein may be an enzyme involved in a biological pathway.

The term "polynucleotide" used herein refers to a polymer of nucleotide residues with no limitation with respect to the minimum length of the polymer. Preferably, the polynucleotide has at least 60 nucleotides. The polynucleotide may be a DNA, cDNA or RNA molecule. A polynucleotide may comprise a gene encoding a desirable protein (e.g., an enzyme), optionally under the control of an inducible promoter.

The term "variant" of a protein or polynucleotide used herein refers to a polypeptide having an amino acid or nucleic acid sequence that is the same as the amino acid or nucleic acid sequence of the protein or polynucleotide except having at least one amino acid or nucleic acid modified, for example, deleted, inserted, or replaced, respectively. A variant of a protein or polynucleotide may have an amino acid or nucleic acid sequence at least about 80%, 90%, 95%, or 99%, preferably at least about 90%, more preferably at least about 95%, identical to the corresponding amino acid sequence or nucleic acid of the protein or polynucleotide.

The term "derived from" used herein refers to the origin or source, and may include naturally occurring and recombinant microorganisms or molecules, or variants thereof. For example, a gene derived from a bacteria may be identical to the corresponding native gene or a variant thereof in the bacteria, i.e., having a nucleic acid sequence at least about 80%, 90%, 95%, or 99%, preferably at least about 90%, more preferably at least about 95%, identical to the corresponding native gene.

The present invention provides a non-naturally occurring microbe capable of growing in a medium comprising methanol. The methanol contributes to a significant percentage of the carbon source for the microbe. The microbe expresses heterologous methanol dehydrogenase (MDH) and one or more heterologous ribulose monophosphate (RuMP) pathway enzymes.

The term "a significant percentage of the carbon source" used herein refers to that the methanol contributes to at least about 40%, 48%, 50%, 60%, 66%, 70%, 80%, 90%, 95%, 99%, or 100% of the carbon source for the non-naturally occurring microbe. Preferably, the methanol may contribute to at least about 40% of the carbon source. Methanol could be also the sole carbon source, i.e., contributing 100% of the carbon source, for the non-naturally occurring microbe.

The non-naturally occurring microbe is not naturally a methylotrophic microbe, but with this invention, it becomes a methylotrophic microbe. The term "methylotrophic microbe" used herein refers a microbe capable of growing in a medium comprising methanol, which contributes to as least about 40%, 48%, 50%, 60%, 66%, 70%, 80%, 90%, 95%, 99%, or 100%, preferably at least about 40%, more preferably 100%, of the carbon source for the methylotrophic microbe.

The term "microbe" used herein refers to a single cell organism. Examples of microbes include bacteria, archaea, and fungi.

The non-naturally occurring microbe of the present invention may be derived from a microbe selected from the group consisting of facultative aerobic organisms, facultative anaerobic organisms, and anaerobic organisms. In particular, the non-naturally occurring microbe may be derived from a microbe in phyla Proteobacteria, Firmicutes, Actinobacteria, Cyanobacteria, Chloribi, and *Deinococcus-Thermus*. For example, the non-naturally occurring microbe may be derived from *Escherichia, Bacillus, Clostridium, Enterobacter, Klebsiella, Enterobacteria, Mannheimia, Pseudomonas, Acinetobacter, Shewanella, Ralstonla, Geobacter, Zymomonas, Acetobacter, Geobacillus, Lactococcus, Streptococcus, Lactobacillus, Corynebacterium, Streptomyces, Propionibacterium, Synechocystis, Synechococcus, Cyanobacteria, Chlorobi,* or *Deinococcus*. Preferably, the non-naturally occurring microbe of the present invention is *E. coli*.

The heterologous methanol dehydrogenase (MDH) is an enzyme capable of converting methanol to formaldehyde (HCHO) in the non-naturally occurring microbe of the present invention. The heterologous MDH may be derived from any other microbe, for example, *Bacillus stearothermophilus* or other naturally facultative methylotrophs such as *B. methanolicus*. The expression of the heterologous MDH may be under the control of a constitutive or an inducible promoter, for example, a formaldehyde responsive promoter, a methanol inducible promoter, a lactose inducible promoter, or a temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically.

The term "ribulose monophosphate (RuMP) pathway" as used herein refers to a formaldehyde assimilation pathway in a microbe, which fixes formaldehyde produced via methanol oxidation to the central metabolite ribulose-5-phosphate. Exemplary RuMP pathway enzymes include 3-hexulose-6-phosphate synthase (HPS), and 3-hexulose-6-phosphate isomerase (PHI). The heterologous RuMP pathway enzymes may be derived from any microbe, for example, *M. gastri, B. brevis, B. subtilis, B. methanolicus, Methylobacillus flagellatus,* or *Methylomonas* str. L3, or other obligate or facultative aerobic or anaerobic methylotrophs. Preferably, the RuMP pathway enzymes may be derived from the same microbe. The RuMP pathway enzymes may be expressed as a fusion protein. For example, the heterologous HPS and the heterologous PHI may be expressed as a fusion protein. The non-naturally occurring microbe of the present invention may have any native formaldehyde detoxification system such as the frmRAB operon. The non-naturally occurring microbe may further contain a deletion of the frmRAB operon or deletion of a similar set of genes that code for enzymes that oxidize formaldehyde to CO formaldehyde typically for formaldehyde detoxification purposes. The expression of any one of the heterologous RuMP pathway enzymes may be under the control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous MDH, heterologous HPS, and heterologous PHI.

The non-naturally occurring microbe of the present invention may further express heterologous pentose-phosphate pathway (PPP) enzymes. The term "pentose-phosphate pathway (PPP)" as used herein refers to a cyclic metabolic pathway which functions to regenerate the ribulose-5-phosphate used by the RuMP pathway. Exemplary PPP enzymes include phosphofructokinase (PFK), fructose bisphosphate aldolase (FBA), transketolase (TKT), fructose/sedoheptulose biphosphatase (GLPX), ribulose phosphate epimerase (RPE), ribose-5-phosphate isomerase (RPI) and transaldolase (TAL). The heterologous PPP enzymes (e.g., PFK, FBA, TKT, GLPX, RPE, RPI, and TAL) may be derived from any microbe, for example, any bacterium, archaeon, fungus or even animal cells as long as the genes have been optimized for expression in the host organism as is now well practiced by those skilled in the art. Preferably, the heterologous PPP enzymes are derived from the same microbe. Some or all of the PPP pathway enzymes may be expressed as a fusion protein. The expression of any one of the heterologous PPP enzymes may be under the control of a constitutive or an inducible promoter, for example, a formaldehyde or methanol responsive promoter, a lactose inducible promoter, or a temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous MDH, heterologous HPS, heterologous PHI, heterologous PFK, heterologous FBA, heterologous TKT, heterologous GLPX, heterologous TAL, heterologous RPI, and heterologous RPE.

The non-naturally occurring microbe of the present invention may further express one or more heterologous cyclic formaldehyde dissimilation enzymes. Exemplary cyclic formaldehyde dissimilation enzymes include glucose-6-phosphate isomerase (PGI), glucose-6-phosphate-1-dehydrogenase (ZWF), 6-phosphogluconolactonase (PGL), and 6-phosphogluconate dehydrogenase (GND). The non-naturally occurring microbe of the present invention may contain a deletion of the phosphogluconate dehydratase gene (EDD). The heterologous cyclic formaldehyde dissimilation enzymes may be derived from any microbe. Some or all of the cyclic formaldehyde dissimilation enzymes may be expressed as a fusion protein. The expression of any one of the heterologous cyclic formaldehyde dissimilation enzymes may be under the control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous MDH, heterologous HPS, heterologous PHI, heterologous PFK, heterologous FBA, heterologous TKT, heterologous GLPX, heterologous TAL, heterologous RPI, heterologous RPE, heterologous PGI, heterologous ZWF, heterologous PGL, and heterologous GND.

The non-naturally occurring microbe of the present invention may further express heterologous $CO_2$ fixation pathway enzymes. The term "$CO_2$ fixation pathway" as used herein refers to the ability of a microbe to utilize $CO_2$ or it salts such as various mono and bicarbonate salts. Exemplary $CO_2$ fixation pathway enzymes include carbonic anhydrase (CA), formate dehydrogenase (FDH), formaldehyde dehydrogenase (FLD); the enzymes of the reductive tricarboxylic acid cycle such as ATP citrate lyase (ACL), 2-oxoglutarate:ferredoxin oxidoreductase (OGOR), isocitrate dehydrogenase (ICDH), and fumarate reductase (FR); the enzymes of the glycine cleavage system such as aminomethyltransferase (AMT), dehydrolipoyl dehydrogenase (LPDH), glycine dehydrogenase (GDH); and the enzymes of the non-oxidative glycolysis pathway including fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase.

The heterologous $CO_2$ fixation pathway enzymes such as carbonic anhydrase (CA) (EC 4.2.1.1), formate dehydrogenase (FDH) (EC 1.2.1.43 or EC1.2.1.2) and formaldehyde dehydrogenase (FLD) (EC 1.1.1.284) may be derived from several microbes (or host cells), for example, *E. coli*, acetogenic bacteria, various yeasts or even animal cells. Some or all of the heterologous $CO_2$ fixation pathway enzymes may be expressed as a fusion protein. The expression of any one of the heterologous $CO_2$ fixation pathway enzymes may be under the control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous MDH, heterologous HPS, heterologous PHI, heterologous PFK, heterologous FBA, heterologous TKT, heterologous GLPX, heterologous TAL, heterologous RPI, heterologous RPE, heterologous PGI, heterologous ZWF, heterologous PGL, heterologous GND, heterologous CA, heterologous FDH, and heterologous FLD.

The non-naturally occurring microbe of the present invention may further express heterologous dihydroxyacetone synthase (DHAS, EC=2.2.1.3), which is also known as formaldehyde transketolase or glycerone synthase. Additionally, the non-naturally occurring microbe may further express heterologous dihydroxyacetone kinase (DAK, EC=2.7.1.29), which is also known as glycerone kinase. The DHAS and DAK may be derived from any microbe, for example, any methylotrophic yeast or from the bacterium *Mycobacterium* sp. JC1. The expression of any one of the heterologous DHAS and heterologous DAK enzymes may be under the control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically In some preferred embodiments, the non-naturally occurring microbe expresses heterologous MDH, heterologous HPS, heterologous PHI, heterologous PFK, heterologous FBA, heterologous TKT, heterologous GLPX, heterologous TAL, heterologous RPI, heterologous RPE, heterologous PGI, heterologous ZWF, heterologous PGL, heterologous GND heterologous CA, heterologous FDH, heterologous FLD, heterologous DHAS, and heterologous DAK.

The present invention also provides a method for producing a metabolite. The method comprises growing a non-naturally occurring microbe of the present invention in a medium comprising methanol. The methanol contributes to a significant percentage of the carbon source for the non-naturally occurring microbe.

The methanol may contribute to at least about 40%, 48%, 50%, 60%, 66%, 70%, 80%, 90%, 95%, 99%, or 100% of the carbon source for the non-naturally occurring microbe. Preferably, the methanol may contribute to at least about 40% of the carbon source. More preferably, the methanol is the sole carbon source, i.e., contributing 100% of the carbon source, for non-naturally occurring microbe.

The medium may further comprise other carbon source, for example, fermentable mono, di, oligo or polysaccharides. Exemplary fermentable monosaccharides include glucose, xylose, mannose, arabinose, rhamnose, and ribose. Fermentable di- or oligosaccharides may be sucrose, lactose, maltose, cellobiose, short polymers of these mono- or disaccharides, or long polymers of saccharides, for example, cellulose and xylan. The other carbon source may contribute to no more than about 40%, preferably no more than about 30%, more preferably no more than about 20%, most preferably no more than about 10% of the carbon source for the non-naturally occurring microbe.

The metabolite may be selected from the group consisting of 4-carbon chemicals, diacids, 3-carbon chemicals, higher carboxylic acids, alcohols of higher carboxylic acids, polyhydroxyalkanoates, and specialty chemicals. The 4-carbon chemicals may be selected from the group consisting of butyrate, n-butanol, i-butanol, 2-butanol, 2,3-butanediol, and 1,4-butanediol. The diacids may be selected from the group consisting of oxalic, malonic, succinic, glutaric, adipic, pimelic, pthalic, isopthalic, and terephtlalic. The 3-carbon chemicals may be selected from the group consisting of propanol, propanediol, lactate, and acrylate. The higher carboxylic acids may be selected from the group consisting of pentanoic acids and hexanoic acids. Preferably, the metabolite is n-butanol. The specialty chemicals may include artemisinin, vanillin, anthocyanins, resveratrol, et cetera.

According to the method of the present invention, at least about 30%, 40%, 50%, 60%, 70%, 80%, 90% or 100%, preferably at least about 80%, of the carbon in the metabolite is derived from the methanol. In some embodiments, the metabolite is an amino acid or tricarboxylic add (TCA) intermediate having at one or multiple carbon positions of the chemical up to the fourth position derived from the methanol. The present method may produce a desirable metabolite at least about 100 mg/L(iter) for specialty, high-value chemicals, and at least 1 g/L or higher for commodity, less expensive chemicals and biofuel molecules.

The growing conditions for the non-naturally occurring microbe may be modified to improve the metabolite production or methanol utilization. For example, the non-naturally occurring microbe may be grown anaerobically, or at a temperature higher than 37° C., for example, 40° C., 45° C. or 50° C.

A gene encoding a heterologous enzyme, for example, MDH, the RuMP pathway enzymes (e.g., HPS and PHI), the PPP pathway enzymes (e.g., PFK, FBA, TKT, TAL, GLPX, RPI, and RPE), the cyclic formaldehyde dissimilation enzymes (e.g., PGI, ZWF, PGL, and GND), the $CO_2$ fixation pathway enzymes (e.g., CA, FDH, FLD, reductive tricarboxylic acid cycle enzymes such as ACL, OGOR, ICDH, and FR, glycine cleavage system enzymes such as AMT, LPDH, GDH, non-oxidative glycolysis pathway enzymes such as fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase, DHAS, and DAK, may be modified to improve metabolite production or methanol utilization. The gene may be engineered to be under the control of an inducible promoter, for example, a formaldehyde or methanol responsive promoter, a lactose inducible promoter, or a temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. The gene may also be engineered to modify the corresponding enzyme (e.g., MDH) to improve the enzyme's substrate specificity and optimal temperature in the non-naturally occurring microbe.

The method for producing a metabolite may further comprise fixing $CO_2$. The medium may be modified by containing higher levels of methanol which is more reduced than a sugar (e.g., glucose) such that more electrons may be generated under the conditions the non-naturally occurring microbe is grown. Other media modifications may also enable an enhanced availability of electrons in the cells. Such additives would be reducing agents or dyes (such as Methyl Viologen (MV) and other viologens). Such electrons may enable the non-naturally occurring microbe to grow on the medium while fixing $CO_2$. According to this method, $CO_2$ release may be reduced by at least about 20%, preferably by at least about 30-50%, more preferably up to about 75%.

For each non-naturally occurring microbe capable of growing in a medium comprising methanol, wherein the methanol contributes to a significant percentage (e.g., at least about 40%, 48%, 50%, 60%, 66%, 70%, 80%, 90%, 95%, 99%, or 100%) of the carbon source for the non-naturally occurring microbe, a method for preparation is provided. The preparation method comprises expressing heterologous methanol dehydrogenase (MDH) and heterologous ribulose monophosphate (RuMP) pathway enzymes in a non-methylotrophic microbe. The RuMP pathway enzymes may include 3-hexulose-6-phosphate synthase (HPS), 3-hexulose-6-phosphate isomerase (PHI). The non-naturally occurring microbe of the present invention may have any native formaldehyde detoxification system such as the frmRAB operon. The non-naturally occurring microbe may further contain a deletion of the frmRAB operon or deletion of a similar set of genes that code for enzymes that oxidize formaldehyde to CO formaldehyde typically for formaldehyde detoxification purposes. Preferably, the method comprises expressing heterologous MDH, heterologous HPS, and heterologous PHI.

The method may further comprise expressing heterologous pentose-phosphate pathway (PPP) enzymes in the non-methylotrophic microbe. The PPP enzymes may include phosphofructokinase (PFK), fructose bisphosphate aldolase (FBA), transketolase (TKT), transaldolase (TAL) fructose/sedoheptulose biphosphatase (GLPX), ribulose phosphate epimerase (RPE), and ribose-5-phosate isomerase (RPI).

The method may further comprise expressing one or more heterologous cyclic formaldehyde dissimilation enzymes in the non-methylotrophic microbe. The enzymes may include glucose-6-phosphate isomerase (PGI), glucose-6-phosphate-1-dehydrogenase (ZWF), 6-phosphogluconolactonase (PGL), and 6-phosphogluconate dehydrogenase (GND). The non-naturally occurring microbe of the present invention may contain a deletion of the phosphogluconate dehydratase gene (edd).

The method may further comprise expressing heterologous $CO_2$ fixation pathway enzymes in the non-methylotrophic microbe. The heterologous $CO_2$ fixation pathway enzymes may include carbonic anhydrase (CA), formate dehydrogenase (FDH), formaldehyde dehydrogenase (FLD; the enzymes of the reductive tricarboxylic acid cycle such as ATP citrate lyase (ACL), 2-oxoglutarate: ferredoxin oxidoreductase (OGOR), isocitrate dehydrogenase (ICDH), and fumarate reductase (FR); the enzymes of the glycine cleavage system such as aminomethyltransferase (AMT), dehydrolipoyl dehydrogenase (LPDH), glycine dehydrogenase (GDH); and the enzymes of the non-oxidative glycolysis pathway including fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase.

The method may further comprise expressing heterologous dihydroxyacetone synthase (DHAS, EC=2.2.1.3) in the non-methylotrophic microbe. DHAS is also known as formaldehyde transketolase or glycerone synthase. The non-methylotrophic microbe may further express heterologous dihydroxyacetone kinase (DAK, EC=2.7.1.29). DAK is also known as glycerone kinase.

The preparation method may further comprise introducing into the non-methylotrophic microbe a gene encoding any of the heterologous enzymes selected from the group consisting of the heterologous MDH, the heterologous RuMP pathway enzymes (e.g., HPS and PHI), the heterologous PPP enzymes (e.g., PFK, FBA, TKT, GLPX, TAL, RPI and RPE), the heterologous cyclic formaldehyde dissimilation pathway (PGI, ZWF, PGL, GND), the heterologous $CO_2$ fixation pathway enzymes (e.g., CA, FDH, FLD, reductive tricarboxylic acid cycle enzymes such as ACL, OGOR, ICDH, and FR, glycine cleavage system enzymes such as AMT, LPDH, GDH, non-oxidative glycolysis pathway enzymes such as fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase), heterologous DHAS, and heterologous DAK. The gene may be expressed transiently in the non-methylotrophic microbe. The gene may be integrated into the genome of the non-methylotrophic microbe. The gene may be under the control of an inducible promoter, for example, a formaldehyde or methanol responsive promoter, a lactose inducible promoter, or temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. The non-naturally occurring microbe may also contain deletions of the fmrRAB operon and the edd gene.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Growth on Methanol and Biomass Labeling from $^{13}C$ Methanol of *E. coli* Strain Carrying Plasmid pETM6PtacBst_MDH/Mg_RuMP Strain We constructed a vector utilizing the pETM6 backbone, the Ptac promoter along with the MDH gene from *B. stearothermophilus* and the HPS-PHI fusion from *M. gastri*. These genes, as currently constructed, are in a monocistronic configuration. Cultures were pre-grown and induced using the following protocol. A single colony was picked from a LB plate and grown at 37° C. for 6 h in LB broth. These cultures were then pelleted and resuspended at an $OD_{600}$ of 0.5 in MOPS media containing 0.4% ribose and 0.1 mM IPTG for 12 h at 37° C. Samples were taken from these overnight grown cultures, lysed and analyzed for expression of both the MDH and RuMP fusion protein. Cultures induced overnight in MOPS ribose were also resuspended in fresh MOPS media containing 500 mM $^{13}C$ methanol at an initial $OD_{600}$ 1.0. Samples were taken at 6 and 18 h for GC-MS analysis of $^{13}C$ methanol incorporation into biomass and intracellular metabolites.

Figure 3:
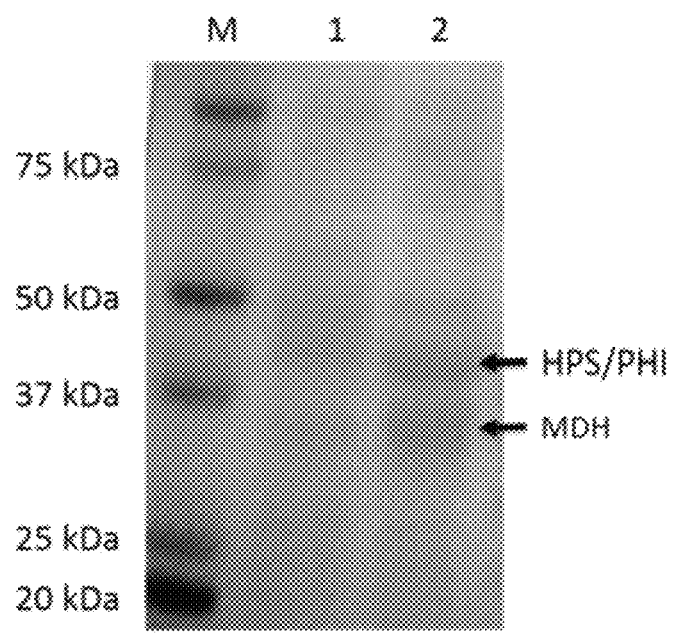
FIG. 3 shows SDS-PAGE of *E. coli* cell lysates expressing *B. stearothermophilus* MDH and *M. gastri* RuMP fusion. Cells were induced overnight with 0.1 mM IPTG in MOPS+ribose. Lane 1: pETM6Ptac Empty. Lane 2: pETM6PtacBst_MDH/Mg_fusion.
Figure 4A:
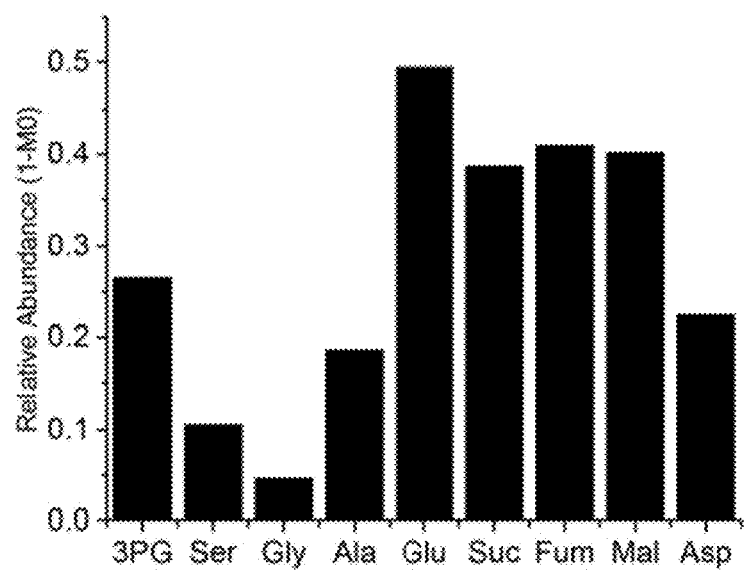
FIGS. 4A-B show A) relative abundance of all labeled fragments and B) relative abundance of each labeled mass isotopomer from labeling experiment with $^{13}C$-Methanol as tracer. Metabolites shown are 3PG—3-phosphoglycerate, Ser—Serine, Gly—Glycine, Ala—Alanine, Glu—Glutamate, Suc—Succinate, Fum—Fumarate, Mal—Malate, Asp—Aspartate.
Figure 4B:
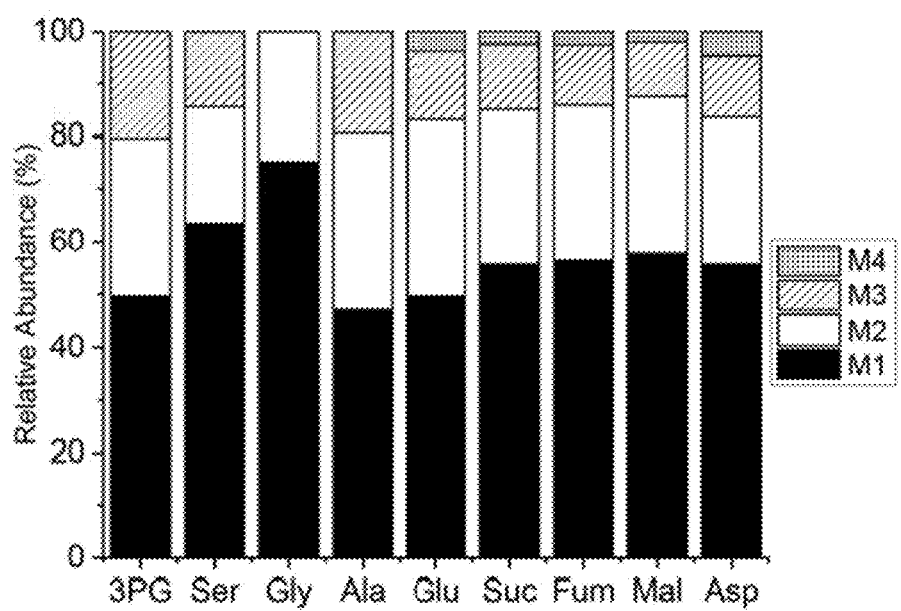

To confirm the newly constructed pETM6Ptac vectors expressed the desired genes, we induced the strain containing the MDH and RuMP fusion overnight in MOPS plus ribose and IPTG and analyzed the cell lysates. We were able to dearly observe the MDH (35 kDa) and the RuMP (41 kDa) (FIG. 3), indicating that both proteins were robustly expressed via the new ptac vectors. To analyze the functionality of these proteins, we transferred the induced ΔfrmA strain expression the MDH and RuMP fusion into MOPS plus 500 mM $^{13}C$ methanol and incubated these cultures were 18 h. We were able to observe incorporation of the methanol into biomass and intracellular metabolites by the recombinant *E. coli* (FIG. 4). Specifically, we detected labeling in amino acids and TCA cycle intermediates (FIG. 4A). Furthermore, we were able to observe multiple carbon labeling on these metabolites (FIG. 4B), which shows that the pathway is cycling back through the pentose phosphate pathway to regenerate ribulose-5-phosphate, which is similar to native methylotrophs. This has never been demonstrated before and unequivocally supports the claims of this invention that methanol can support cell growth of the synthetic methylotroph by giving rise to core metabolites in the cells needed for cell growth.

Figure 5A:
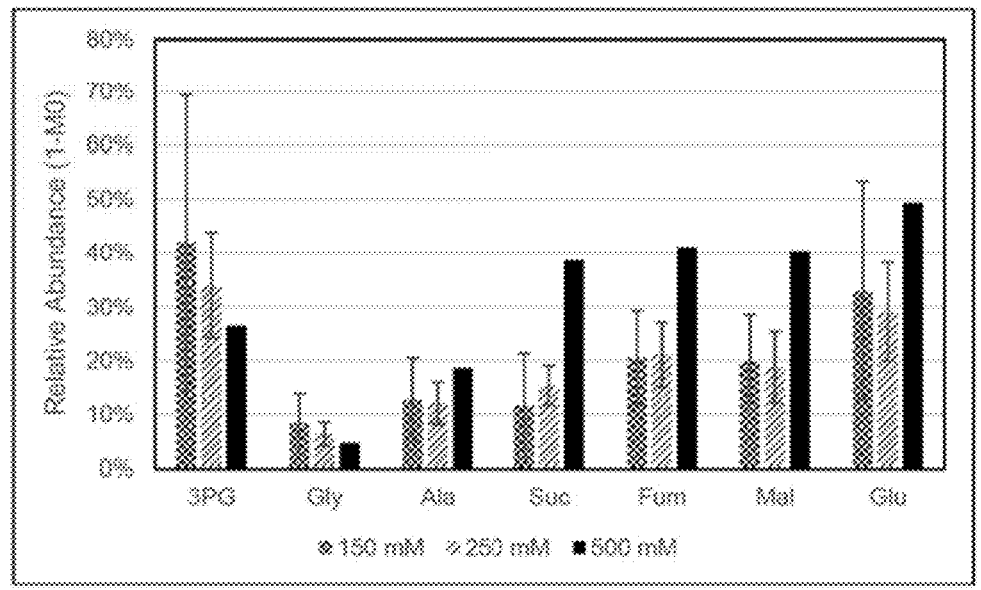
FIGS. 5A-B show A) relative abundance of all labeled fragments from cultures incubated for 18 h in MOPS supplemented with either 150 mM, 250 mM, or 500 mM methanol as the sole carbon source, and B) HPLC analysis. The metabolites shown are 3PG—3-phosphoglycerate, Gly—Glycine, Ala—Alanine, Suc—Succinate, Fum—Fumarate, Mal—Malate, Glu—Glutamate. The HPLC analysis confirmed that methanol was simultaneously being consumed from the media.
Figure 5B:
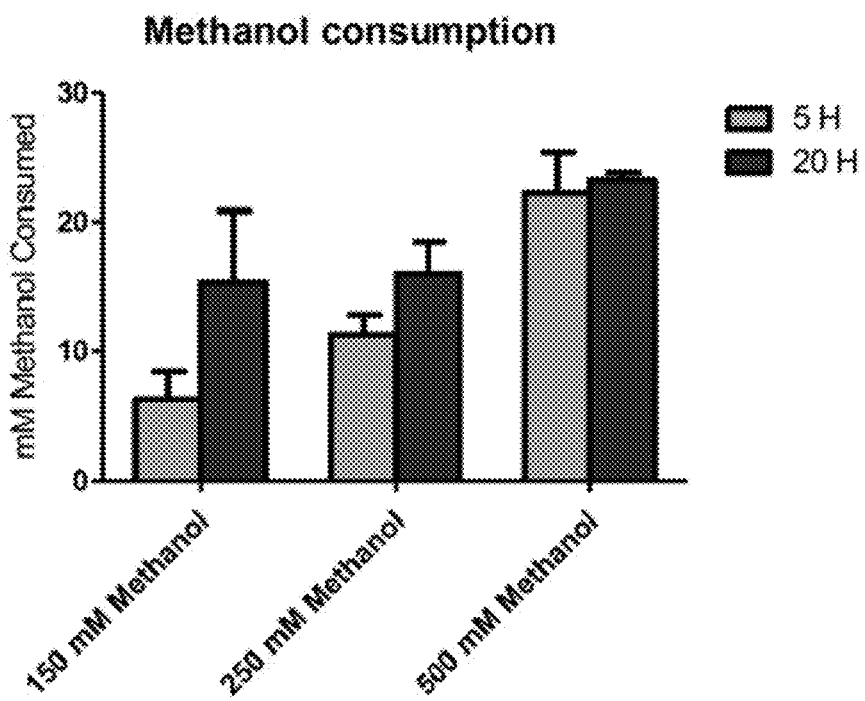

To show that this takes place at various and lower methanol concentrations, we carried out labeling experiments using 150 mM and 250 mM methanol as the sole carbon source. We were, again, able to detect similar levels of metabolite labeling when compared with cultures incubated with 500 mM methanol (FIG. 5A). Methanol consumption coincided with the incorporation of labeled methanol into biomass, with approximately 15 and 18 mM methanol being consumed by the recombinant *E. coli* strain incubated in 150 and 250 mM methanol, respectively (FIG. 5B).

Figure 6A:
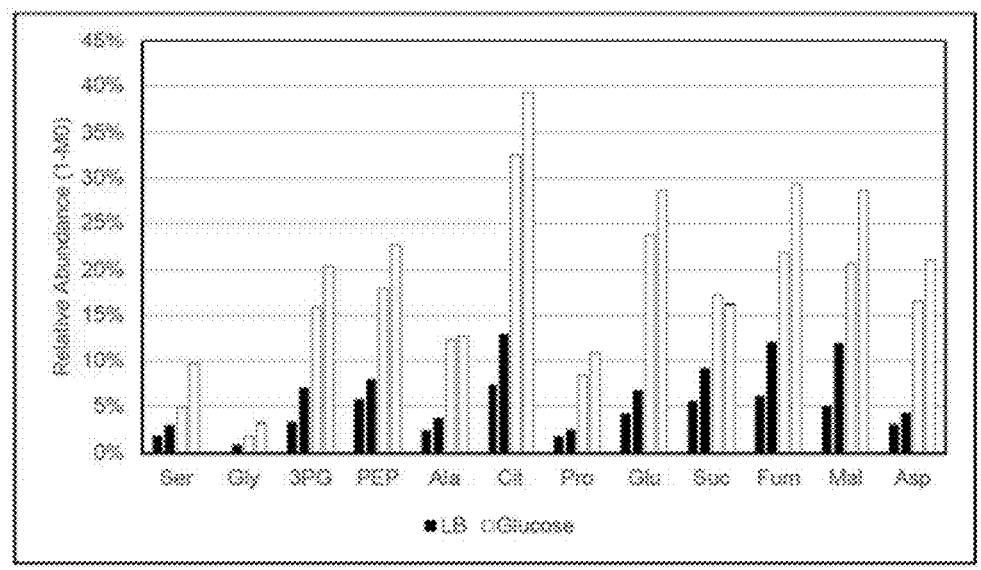
FIGS. 6A-B show *E. coli* containing either the pETM6_BstMDH_MgRuMP or pETM6_Empty where grown either A) MOPS+500 mM methanol+2 mM glucose. B) Methanol incorporation was detected in these cultures and the relative abundance of fragments is shown. The first bar indicates samples taken after 6 h of growth and the second bar indicates samples taken after 18 h of growth.
Figure 6B:
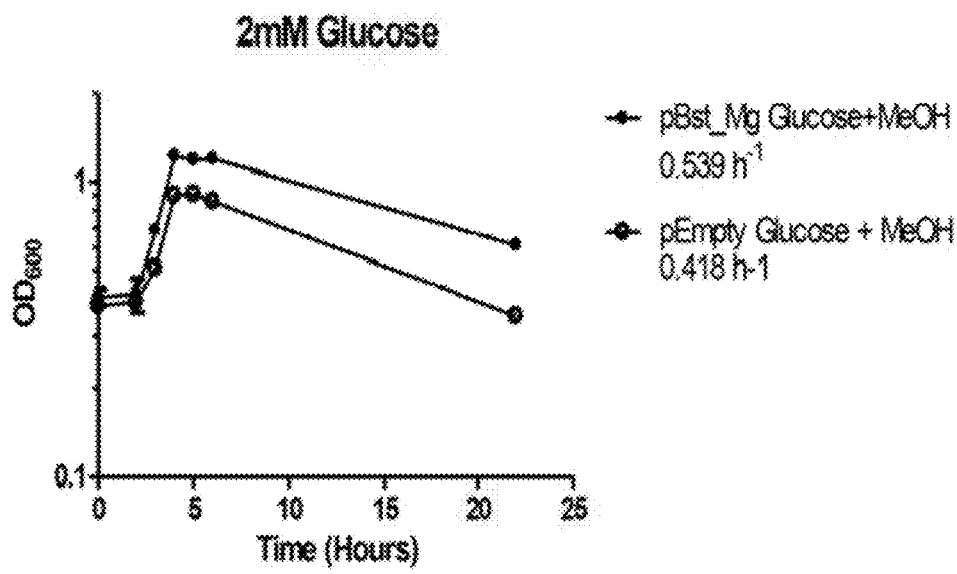

Example 2. Methanol is Incorporated into Biomass and Supports Cell Growth. Methanol as a Co-Substrate to Improve the Capability of Synthetic Methylotrophic *E. coli* to Produce More Reduced Products Such as Alcohols, Carboxylic Acids and Hydrocarbon Molecules Because methanol is more reduced than most sugars typically used as fermentation substrates, use of methanol as a co-substrate will result in the production of more reducing equivalents compared to most sugars and will thus lead to better yields for producing metabolites like alcohols, carboxylic acids and hydrocarbons. We thus hypothesized that methanol could be metabolized by the recombinant *E. coli* strain when grown in the presence of additional carbon sources. After overnight induction in MOPS plus ribose, cultures were transferred to MOPS containing a mixture of methanol (500 mM) and glucose (2 mM). The strain expressing the genes for methanol utilization was able to grow to a higher $OD_{600}$ and with a faster growth rate than the empty vector control (FIG. 6A). Additionally, we were able detect labeling of intracellular metabolites under these culture conditions, indicating that the methanol is still being consumed in the presences of additional nutrient sources (FIG. 6B). Taken together, these data show that methanol is metabolized effectively in the presence of sugars as a carbon and energy source and that it enhances the growth rate and overall yields of the synthetic methylotrophic strain which is able to convert methanol to biomass and metabolites.

Example 3. Methanol Utilization Supports Cell Growth in Growth Media with Typical but Diluted LB Composition Media of industrial fermentations typically contain supplements like yeast extracts and protein hydrolyzates. Heavy use of such supplements have been used in several celebrated new metabolically engineered strains like for the production of i-butanol and the use of reverse beta oxidation to support growth and metabolite production. Here we used a very diluted (1:4) LB broth to show that methanol is utilized without any sugars present and supports cell growth. Standard LB broth contains 10 g/l tryptone and 5 g/l yeast extract to supply carbon and energy for growth. For the growth experiments in methanol, we used MOPS media that supplemented with 2.5 g/l tryptone and 1.25 g/l yeast extract (1:4 LB:MOPS) in addition to 500 mM methanol to assay for growth and methanol incorporation.

Figure 7A:
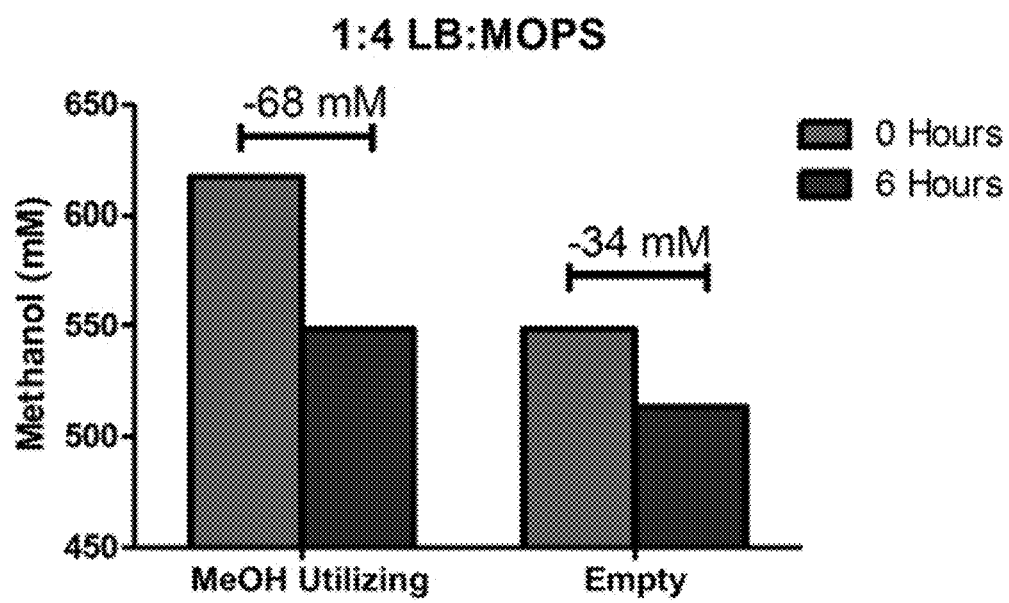
FIGS. 7A-B show growth of MeOH utilizing *E. coli* in mixed methanol and LB media. The MeOH utilizing strain and the empty vector control were pre-cultured and induced overnight in MOPS+ribose. The cells were pelleted and resuspended in 1:4 mixture of LB:MOPS+methanol. This media contains the following nutrient sources: 2.5 g/l tryptone; 1.25 g/l yeast extract; and 500 mM methanol. Change is cell concentration (B) was measured spectrophotometrically and methanol consumption (A) was measured through HPLC analysis.
Figure 7B:
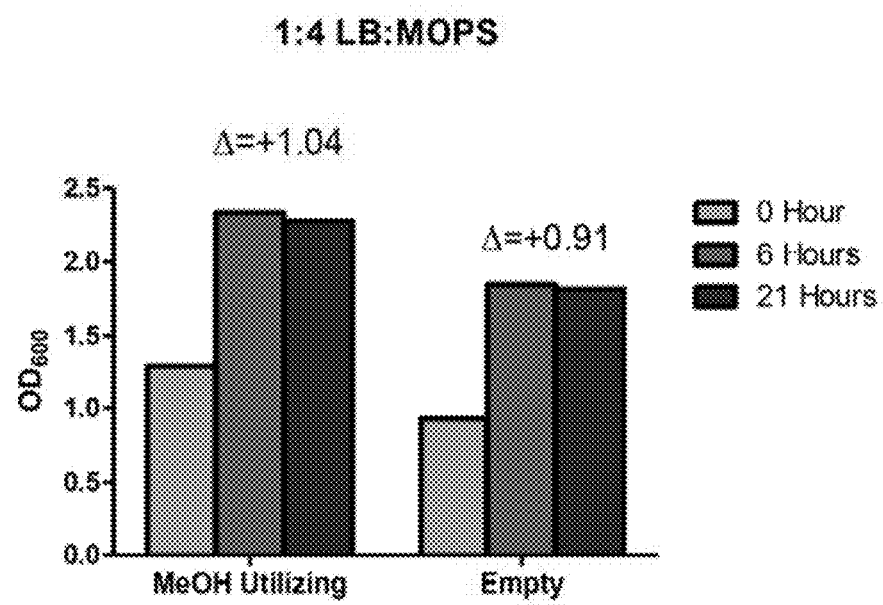

When the MeOH utilizing strain was grown in a 1:4 mixture of LB:MOPS, we were able to observe a 68 mM decrease in methanol concentration, which contrasts to the 34 mM decrease in methanol observed in the empty vector control (FIG. 7). The observation that methanol was decreasing in the negative control was likely due to a combination of high starting OD (~1.0) and non-specific methanol oxidation by the alcohol dehydrogenases present in E. coli (FIG. 7). These data, combined with the data from (FIG. 6B) which shows methanol incorporation in the presence of dilute LB, indicate that methanol is utilized by the cells to support cell growth without the need for added sugars.

Example 4. Methanol Growth Under Anaerobic Conditions

With the ultimate goal of using methanol to be used as a substrate for producing various metabolites such as alcohols (e.g., butanols) or mono- or dicarboxylic acids or other molecules that can be produced by metabolically engineered E. coli and other organisms typically under anaerobic or almost anaerobic conditions, we set out to examine methanol utilization under anaerobic conditions. Cultures were pre-grown and induced as outlined earlier. After overnight induction, cultures were transferred sealed anaerobic bottles containing MOPS+500 mM methanol and 2 mM glucose. We also examined the effect of methyl viologen on anaerobic growth in the presence of methanol. Methyl viologen as previously been demonstrated to consume NADH in E. coli (which should promote methanol oxidation) and induce the pentose phosphate pathway, which should promote regeneration of ribulose-5-phosphate.

Figure 8A:
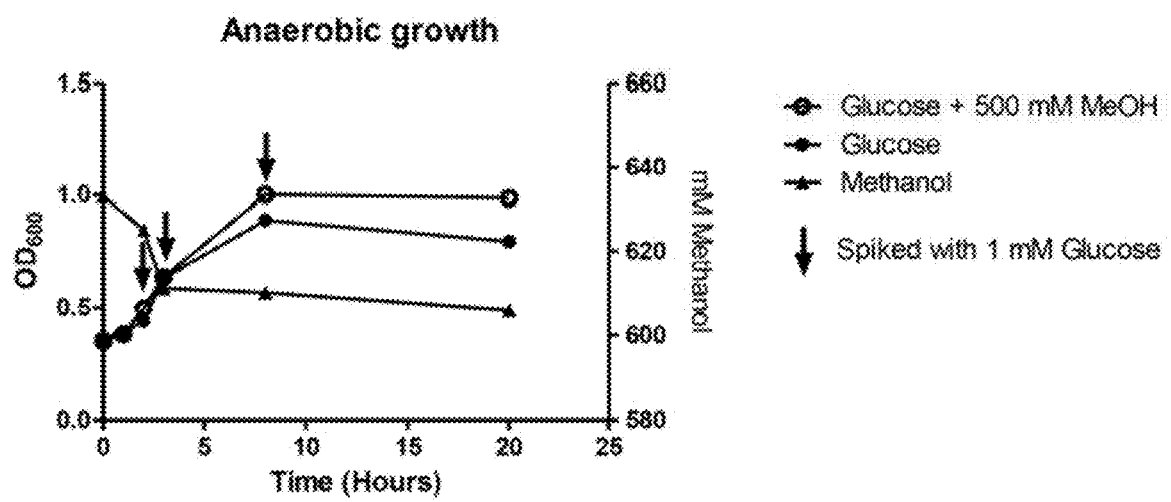
FIGS. 8A-B show growth of cultures under anaerobic conditions in MOPS+glucose or MOPS+glucose+500 mM methanol. Strains were pre-grown aerobically in LB before being induced overnight aerobically in MOPS+ribose. (A) After induction, the cultures were transferred to MOPS+2 mM Glucose+500 mM methanol in sealed anaerobic bottles and grown for the allotted time. (B) Enhanced growth was observed when methanol and 0.15 mM methyl viologen were added to the cultures.
Figure 8B:
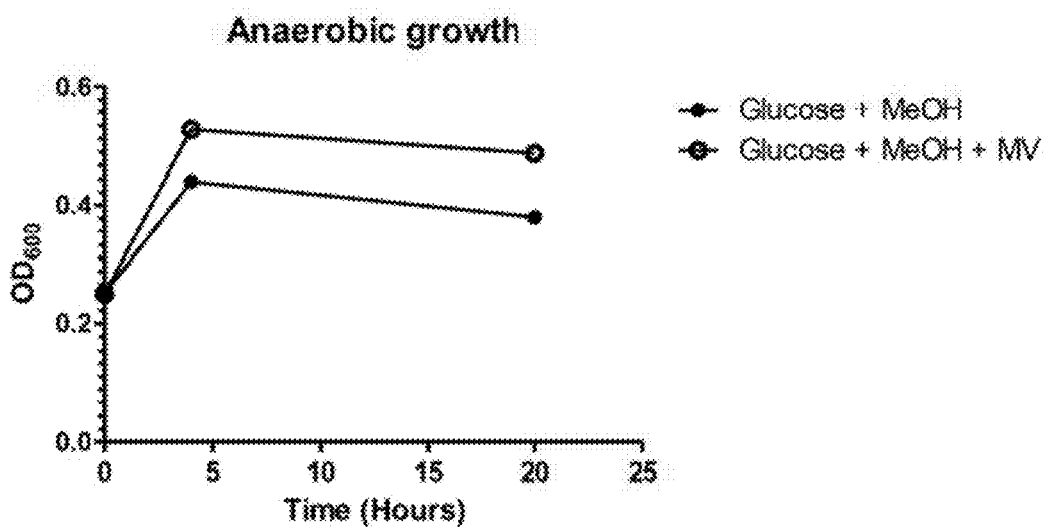

When we compared growth of the methanol utilizing strain anaerobically in either glucose alone or glucose+ methanol, we did not observe a difference in growth. However, supplementation with 0.15 mM methyl viologen lead to higher overall yields when cells were grown in the presence of methanol (FIG. 8). Additionally methyl viologen had no effect on growth in glucose alone. These results show that methyl viologen enhances growth in the presence of methanol and that it is a useful culture supplement to increase the titers of various metabolites that can be produced from E. coli using methanol as carbon and energy and electron source. Anaerobic growth could be reinforced through successive feedings of small quantities of glucose, and again, when the strain was grown in the presence of methanol and glucose, it grew to higher $OD_{600}$ compared when the strain was grown in glucose alone (FIG. 8). This shows that methanol can be utilized anaerobically on batch, fed-batch and continuous mode to support the production of various metabolites from recombinant E. coli and other organisms.

Example 5. Additional, Novel Metabolic Engineering E. coli to Further Enhance Methanol Utilization We devised an additional, novel metabolic engineering strategy to enhance methanol utilization by E. coli. Aside from the main 2 main RuMP genes (PHS and PHI; FIG. 2), it is necessary for methylotrophs to be able to regenerate ribulose-5phosphate, which is the substrate used to fix formaldehyde. Ribulose-5-phoshate is an intermediate of the pentose phosphate pathway, and, in naturally occurring methylotrophs, this pathway is positively regulated by the presence of formaldehyde, which is present during growth on methanol. In E. coli, however, the pentose phosphate pathway is regulated by the ratio of $NAD^+/NADH$ in the cells and by the global regulator SoxS. Therefore, it is possible that the genes needed for ribulose-5-phosphate regeneration are sub-optimally regulated/expressed in E. coli during growth on methanol. Further engineering of this pathway will enhance methanol utilization and drive production of the desired end product.

Figure 9A:
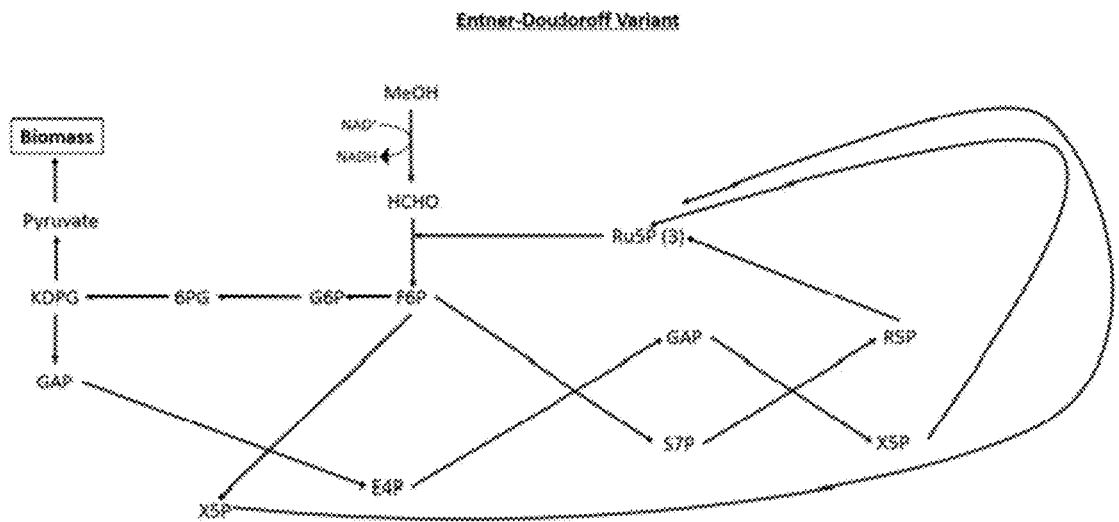
FIGS. 9A-B show variations of the ribulose monophosphate pathway commonly found in methylotrophic bacteria: A) Entner-Doudoroff Variant and B) Fructose Bisphosphate Variant. MeOH, methanol; HCHO, formaldehyde; F6P, fructose-6-phosphate; FBP, fructose 1,6-bisphosphate; G6P, glucose-6-phosphate; 6PG, 6-phosphogluconate; KDPG, 2-keto-3-deoxy-6-phosphogluconate; GAP, glyceraldehyde-3-phosphate; DHAP, dihydroxyacetone phosphate; X5P, xyulose-5-phosphate; E4P, erythrose-4-phosphate; S7P, sedoheptulose-7-phosphate; SBP, sedoheptulose 1,7-bisphosphate; R5P, ribose-5-phosphate; Ru5P, ribulose-5-phosphate.

There are several variants of the RuMP pathway, based upon the route of ribulose-5-phosphate regeneration. The Entner-Doudoroff (ED) variant of the RuMP pathway (FIG. 9A) possess the following stoichiometry:

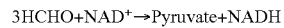

$3HCHO+NAD^+ \rightarrow Pyruvate+NADH$

Figure 9B:
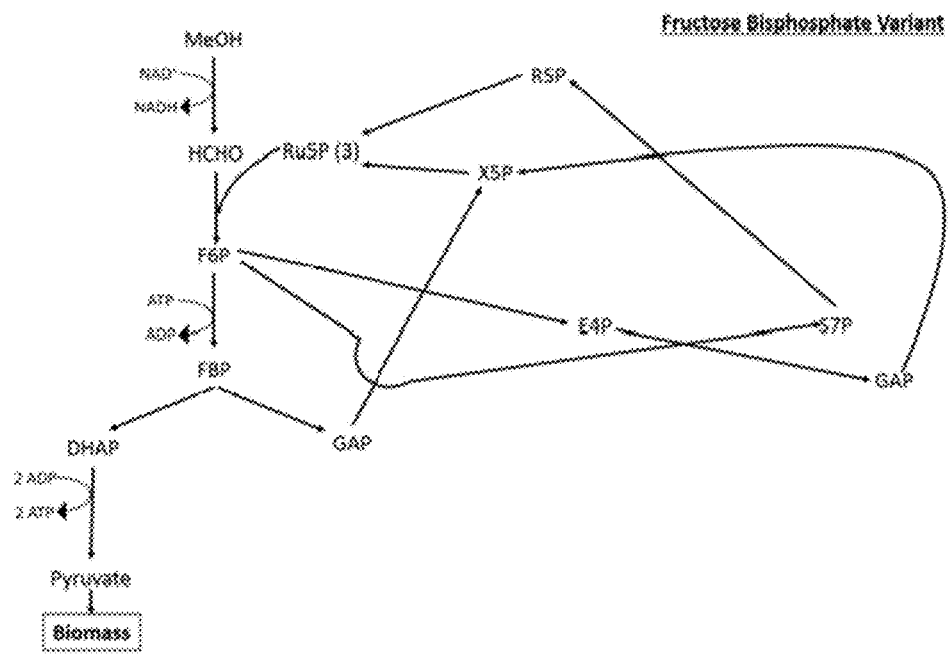

Another version of the RuMP pathway is the fructose 1,6-bisphosphate (FBP) variant (FIG. 9B), which possess the following stoichiometry:

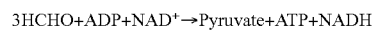

$3HCHO+ADP+NAD^+ \rightarrow Pyruvate+ATP+NADH$

Figure 10:
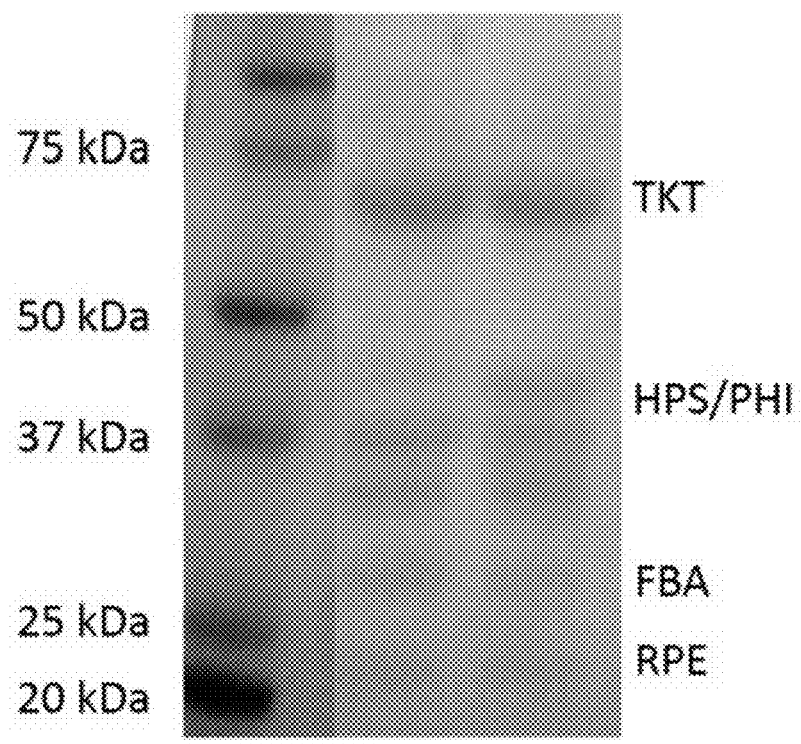
FIG. 10 shows SDS-PAGE of *E. coli* cell lysates expressing RuMP assimilatory pathway genes. Cells were induced overnight with 0.1 mM IPTG in MOPS+ribose. Lane 1: pCDM4_Acessory genes. Lane 2: pETM6PtacBst_MDH/Mg_fusion/pCDM4_Accessory genes.

Thus, directing carbon through the FBP variant will lead to more energy for the recombinant E. coli strain, especially under anaerobic conditions, where ATP is not generated via oxidative phosphorylation. E. coli natively possesses all of the genes required for both the ED and FBP RuMP variants. We have shown above that our recombinant E. coli strain is able to regenerate ribulose-5-phosphate based on our ability to observe multi-carbon labeling of intracellular metabolites. We hypothesize however that the recombinant E. coli is likely using the less energy efficient ED pathway to regenerate ribulose-5-phosphate and generate pyruvate. While the genes for the FBP variant are present in E. coli, these enzymes favor the glycolytic direction (away from ribulose-5-phosphate) compared with the enzymes found in native methylotrophs, which favor the gluconeogenic direction (toward ribulose-5-phosophate). To this end, we have cloned the following genes associated with ribulose-5-phosphate regeneration from the B. methanolicus: fba, fructose 1,6-bisphosphate aldolase; pfk, phosphofructokinase; tkt, transketolase; rpe, ribulose-5-phosphate epimerase; and glpX, fructose 1,6-bisphosphatase. These genes have been cloned and expressed in the pCDM4 vector (FIG. 10). We used repeated growth and labeling experiments with the strain expressing the methanol utilization genes and the ribulose-5-phosphate regenerating genes to show superior methanol utilization and cell growth.

Example 6. Using Methanol to Generate Additional Reducing Equivalents

Many native methylotrophs also possess what is known as a RuMP dissimilation pattern. This pathway uses the fructose-6-phosphate generated by HPS and PHI enzymes and sequentially converts it 6-phosphogluconate, which is then converted to ribulose-5-phosphate. This process yields 2

NADPH and 1 $CO_2$. It is believed that methylotrophs (especially those that use the ED RuMP pathway) use this dissimilation pathway to generate the reducing equivalents used to power the electron transport chain. Again, the genes for this dissimilation pathway are present in *E. coli*, just likely not regulated by methanol as would be the case for native methylotrophs. To this end, we will overexpress the first gene in this pathway, glucose-6-phosphate dehydrogenase, which will force some of the fructose-6-phosphate through the dissimilation pathway. Since 6-phosphogluconate is the branching point in *E. coli* between the pentose phosphate pathway (desired) and the Entner Doudoroff pathway (undesired), we will also delete the first gene in the ED pathway, 6-phosphogluconate dehydrogenase. This will ensure the carbon flux is through the dissimilatory pathway. Engineering of the pentose phosphate pathway to perform the assimilatory and dissimilatory RuMP pathway is novel for *E. coli* and results in a recombinant strain capable of using methanol more efficiently a sole carbon and energy source.

Figure 11:
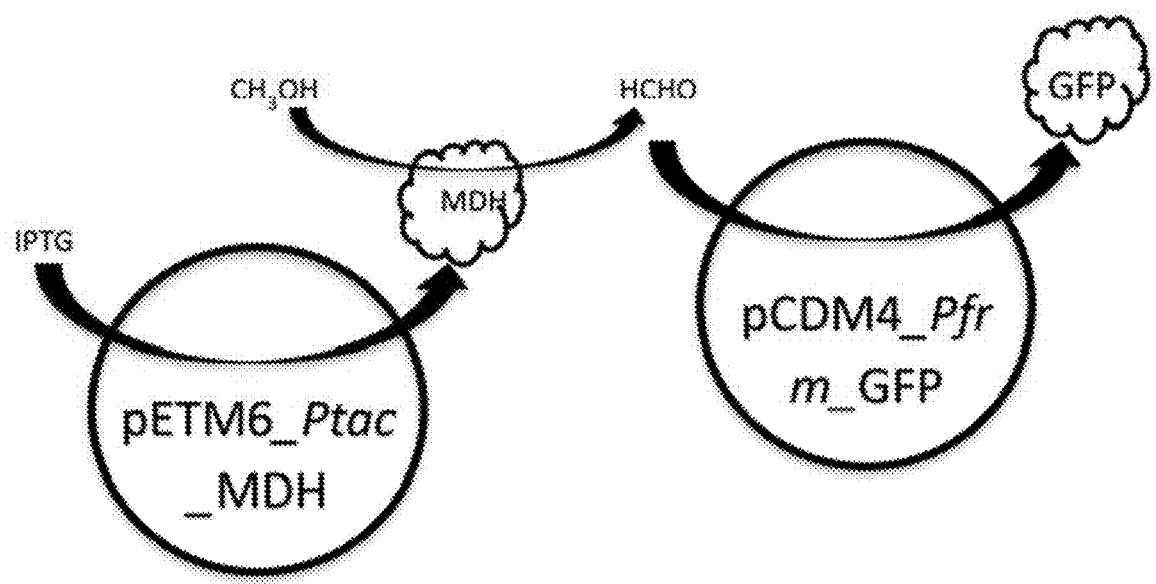
FIG. 11 shows conceptual illustration of a dual plasmid reporter system. A double plasmid containing *E. coli* strain will house the plasmids, pETM6_Ptac_MDHlib and pCDM4_Pfrm_GFP. Upon MDH library expression with IPTG, MeOH will be added and oxidized to HCHO by active MDH mutants. GFP expression will then be utilized to select desirable MDH mutants via FACS.
Figure 12:
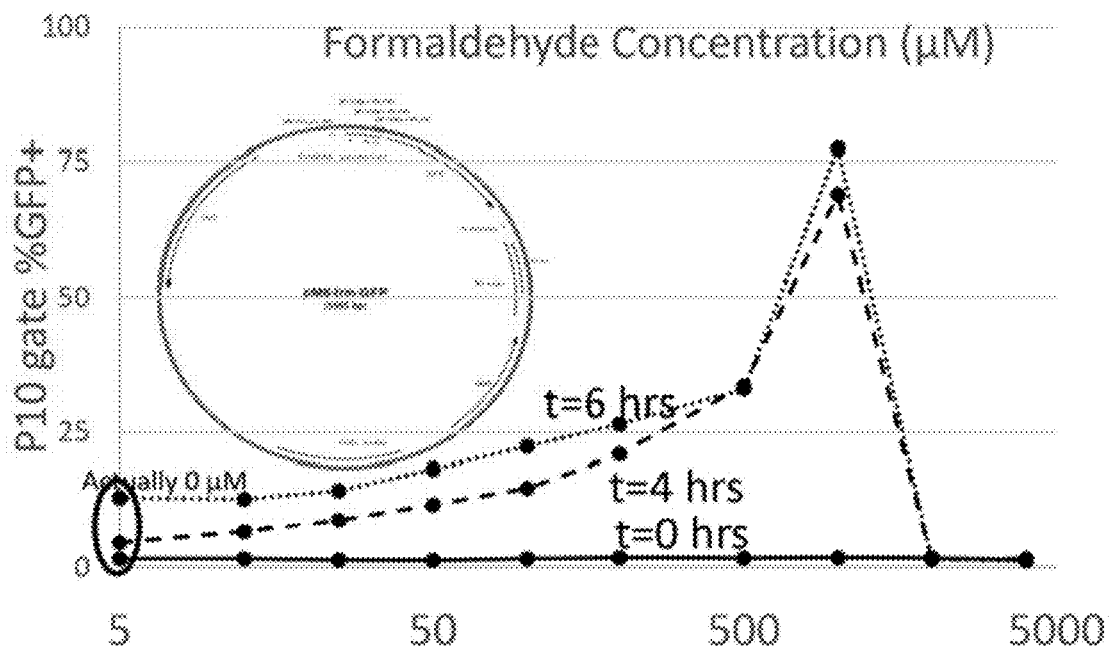
FIG. 12 shows response curve for *E. coli* pETM6_Pfrm_GFP against HCHO. GFP expression correlated with HCHO concentration over time. Overnight LB cultures were transferred to MOPS+0.1% glucose for the experiment. No growth was observed in 2 and 4 mM HCHO cultures, explaining the absence of GFP expression.
Figure 13:
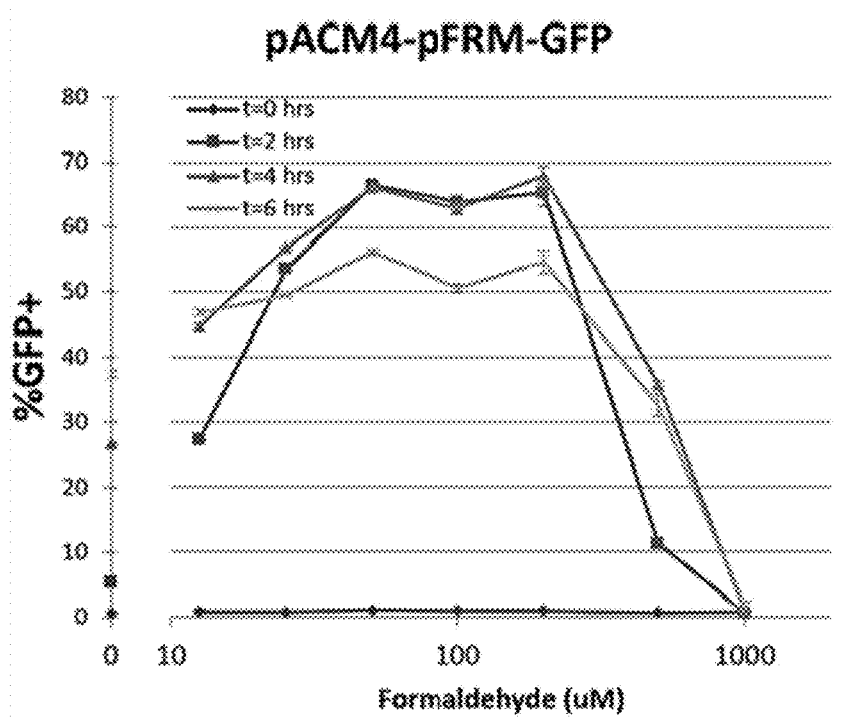
FIG. 13 shows response curve for *E. coli* pACM4_pFRM_GFP against HCHO. GFP expression correlated with HCHO concentration over time. Overnight LB cultures were transferred to MOPS+0.1% glucose for the experiment. Retarded growth was observed in 500 and 1000 µM HCHO cultures, explaining the decreased of GFP expression.
Figure 14:
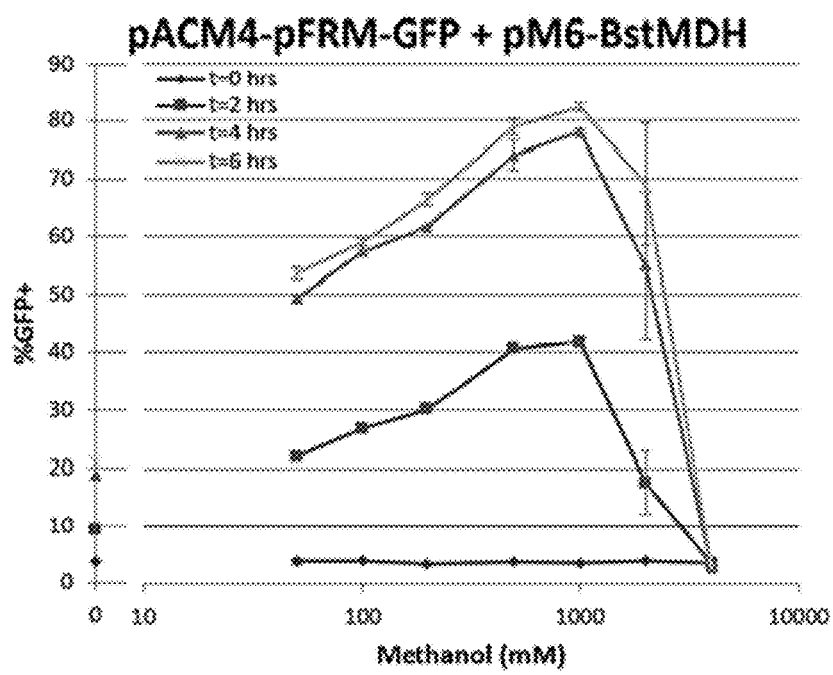
FIG. 14 shows response curve for *E. coli* pACM4_pFRM_GFP+pETM6-BstMDH against methanol. GFP expression correlated with methanol concentration over time. Overnight LB cultures were transferred to MOPS+ 0.1% glucose for the experiment. Retarded growth was observed in 2000 and 4000 mM methanol cultures, explaining the decreased of GFP expression.

Example 7. High-Throughput Assays for Protein Engineering MDH Proteins: Using FACS (Fluorescence-Activated Cell Sorting) for Screening MDH Libraries We hypothesize that one potential limitation for generating a methylotrophic strain of *E. coli* is the ability of the NAD-dependent MDHs to efficiently oxidize methanol at the lower temperatures *E. coli* requires to grow. Thus we use protein engineering of the MDHs either via family shuffling or error prone PCR and generating libraries with these mutagenized copies. This requires a method to easily and in a high throughput manor screen for MDH activity in *E. coli*. We developed a flow cytometry based technique for screening the MDH library for desirable mutants based on formaldehyde production. This strategy utilizes a dual plasmid reporter system: one plasmid, pETM6_Ptac_MDHlib contains the MDH library, and the other plasmid, pCDM4_Pfrm_GFP contain a Green-fluorescent protein (GFP) gene under the control of a formaldehyde responsive promoter. An illustrative example of this concept is presented in FIG. 11. Upon MDH library expression with IPTG, MeOH will be added and oxidized to HCHO by active MDH mutants. The amount of GFP expression, which will correlate to HCHO production (FIGS. 12-13), will then to be utilized to select MDH mutants with higher activity via fluorescence-activated cell sorting (FACS). As seen in FIG. 14, this method can be used to detect a wide range of methanol concentrations.

Example 8. Reversibility of the Formate Dehydrogenase Activity as Tested In Vivo by $^{14}C$ Incorporation Assay As illustrated in FIG. 2, the proposed Scheme 1 for $CO_2$ fixation depends on the reversibility of both the formate dehydrogenase (FDH) and formaldehyde dehydrogenase (FDdH) activity along with the overexpression of a carbonic anhydrase (CA) in order to achieve high intracellular levels of $CO_2$. In the present work we were able to show incorporation of $^{14}C$ from labeled sodium bicarbonate into the cell biomass. The possible path of the $^{14}C$ incorporation is the following:

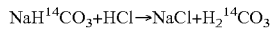

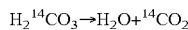

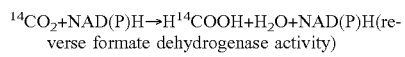
verse formate dehydrogenase activity)

In more detail, the labeling experiment was performed as follows: Single overexpression *E. coli* colonies of *Candida boindini* FDH and *Clostridium carboxidivorans* FDH (selenocysteine codon was substituted with cysteine codon) along with the empty vector control (pACYCDuet-1) were grown overnight at 37° C. in TB broth. The cultures were used the next day to inoculate larger TB broth cultures. When the cultures reached an $OD_{600}$ of 0.5, 0.1 mM IPTG and 5 ul of 1 mCi/ml $^{14}C$ sodium bicarbonate was added and the cultures were transferred to serum bottles in order to grow anaerobically for 4 h. After 4 h the culture was treated with $H_2SO_4$ to release any unincorporated $^{14}C$ with the form of $^{14}CO_2$. Whole cells were then harvested by centrifugation and the cell pellets were treated with 100 mM Na—K phosphate buffer (pH3.0). After centrifugation the cell pellets were resuspended in a solution of 0.1M sodium dodecyl sulfate and 0.2N NaOH. 1 ml of the resuspended solution was heated at 90° C. for 2 h. Incorporation of $^{14}C$ into the cell biomass was analyzed by liquid scintillation.

Figure 15:
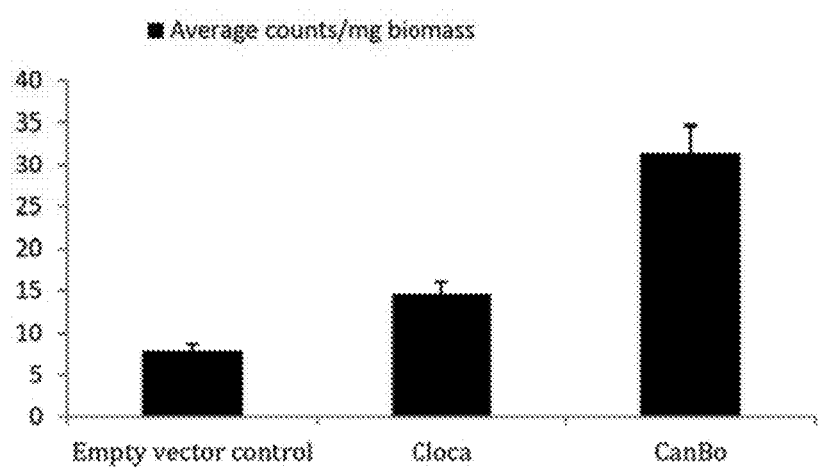
FIG. 15 shows $^{14}C$ incorporation into the cell mass for *Candida boindini* (CanBo) and the *Clostridium carboxidivorans* (Cloca) FDH overexpressing *E. coli* strains.

We were able to detect labeling in the cell mass that was higher for both the *Candida boindini* and the *Clostridium carboxidivorans* FDH compared to the empty vector control (FIG. 15). Background levels of $CO_2$ incorporation were expected because of $CO_2$-pyruvate exchange under the anaerobic conditions.

The above described in vivo labeling experiment showed $^{14}C$ incorporation into the cell biomass suggesting possible reverse formate dehydrogenase activity under anaerobic conditions.

Example 9. Overexpression of Selenocysteine-Containing Formate Dehydrogenases

In most cases, the formate dehydrogenases that act as part of the Wood-Ljungdahl pathway for $CO_2$ fixation in acetogens, are characterized by the presence of selenocysteine in their active site. It has been shown that substitution of the selenocysteine by cysteine in these enzymes reduce their enzymatic activity by 90%. The incorporation of selenocysteine in selenoproteins requires the recruitment of specialized enzymes and t-RNA. In addition the corresponding RNA contains a characteristic structural element, namely SECIS element. The proteins related to this mechanism are encoded by a set of genes, namely selA-D. The codon responsible for the selenocysteine incorporation is UGA, identical with the universal stop codon. This codon when followed by a specific hairpin structure of the RNA, the so-called SECIS element, is not recognized as a STOP codon but instead recruits the necessary machinery for selenocysteine incorporation. The mechanism appears to be highly specific for each organism with SECIS elements of different structure responsible for the recruiting of the appropriate enzymatic machinery in different species.

We explored the heterologous expression of the *Moorella thermoacetica* (Moth) selenocysteine containing FDH-A subunit together with the FDH-B subunit in *E. coli*. The two subunits together when purified were previously shown to have $CO_2$ reductase activity in vitro. To test this activity in vivo we designed a hybrid cDNA sequence that was both codon-optimized for *E. coli* expression, as well as had a substituted Clostridia SECIS element with a potential *E. coli* recognizable one.

Figure 16:
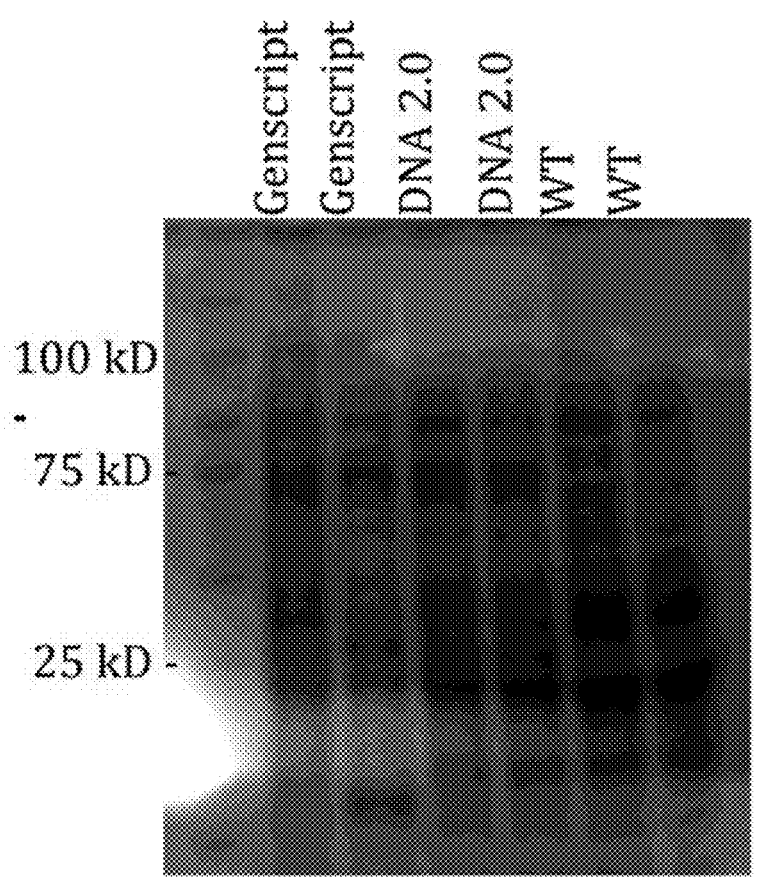
FIG. 16 shows heterologous co-expression of the *Moorella* FDH-A and FDH-B subunit in *E. coli*. The FDH-B overexpression band had the expected size of approximately 75 kDa, FDH-A was expressed only as a truncated protein of 25 kDa for both the Genscript and DNA 2.0 cDNAs.

The recombinant hybrid *Moorella* FDH-A, as designed by two different companies (Genscript and DNA2.0) with the *E. coli* recognizable SECIS element, was expressed in *E. coli* together with FDH-B. While the FDH-B overexpression band had the expected size of approximately 75 kD, FDH-A was expressed only as a truncated protein of 25 kD (FIG. 16) instead of 100 kD that would be the size of the full-length selenoprotein. This finding suggests that the *E. coli* SECIS element itself cannot achieve selenocysteine incorporation.

Considering the above findings, we pursue two alternatives strategies to achieve selenocysteine incorporation into formate dehydrogenases heterologously expressed in *E. coli*. First, we pursue additional mutations at the immediately adjacent sequence of the SECIS element which could help with selenocysteine incorporation. Alternatively, we express the *Moorella* FDH-A with the native *Moorella* SECIS element in parallel with expression of the native *Moorella* selenocysteine-related genes and more specifically selB and selC coding for the selenocysteine-specific elongation factor and the t-RNA(sec).

Example 10. In Vivo MeOH Oxidation and HCHO Reduction Activity of MDHs

Nine $NAD^+$-dependent MDHs (all codon optimized for *E. coli*) from *Bacillus* spp. have been cloned and expressed in *E. coli*. The nine synthesized MDHs are listed in Table 1.

Figure 17A:
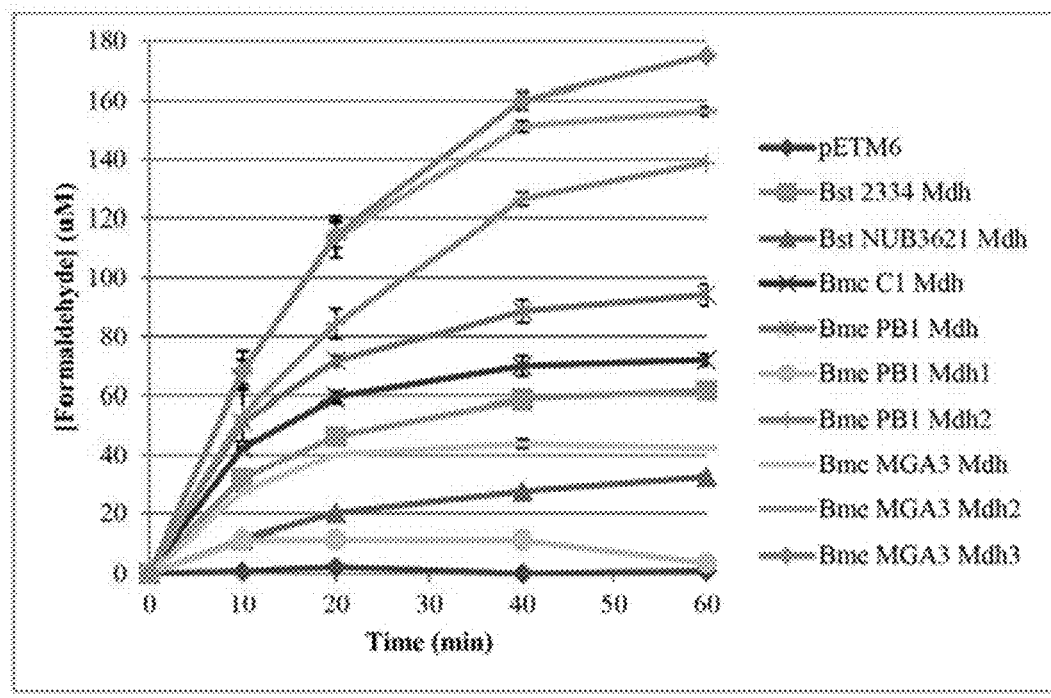
FIGS. 17A-B show A) time course data and B) specific activities (calculated from 10 minute time points) for in vivo assays using *E. coli* BL21(DE3) MDH strains and 1M MeOH. One unit (U) is defined as µmol HCHO produced per minute. Error bars represent averages from two biological replicates.
Figure 17B:
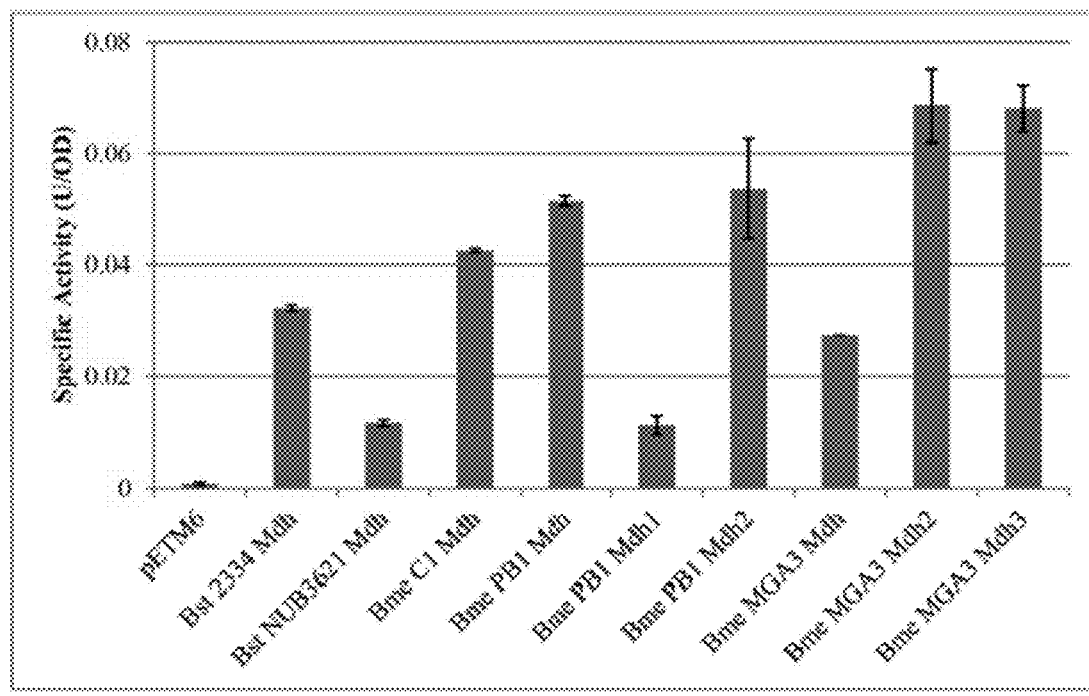
Figure 18A:
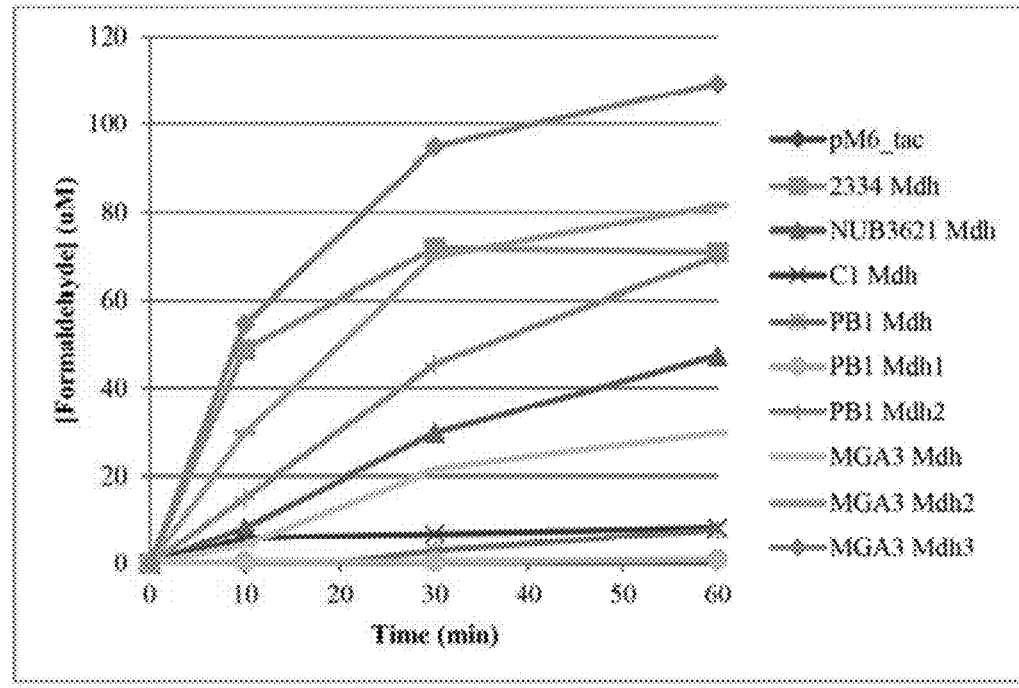
FIGS. 18A-B show A) time course data and B) specific activities (calculated from 10 minute time points) for in vivo assays using *E. coli* ΔfrmA MDH strains and 0.5M MeOH. One unit (U) is defined as µmol HCHO produced per minute.
Figure 18B:
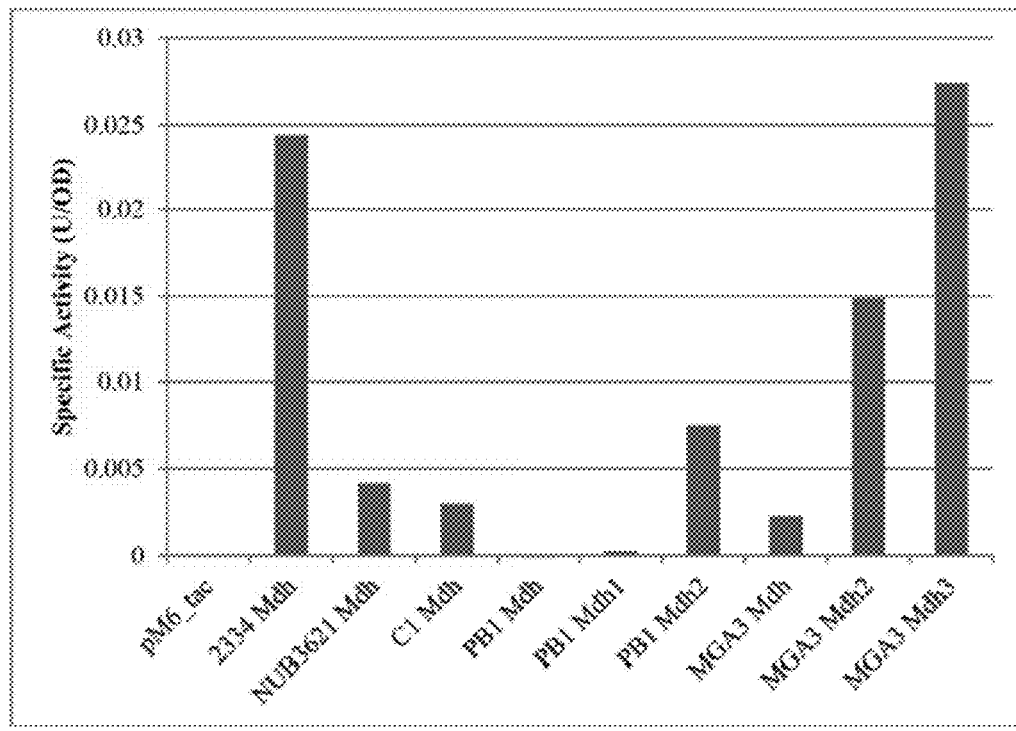

In addition to in vitro activity disclosed earlier, all nine MDHs exhibit in vivo methanol oxidation activity in *E. coli* BL21(DE3) strains (FIG. 17) but only eight possess in vivo activity in the *E. coli* ΔfrmA strain, which lacks the native FrmRAB system for formaldehyde oxidation (FIG. 18). In *E. coli* the enzymes that perform the formaldehyde degradation are encoded by a three gene operon namely, fmrRAB. frmR encodes a transcriptional repressor of the operon, frmA encodes the S-hydroxymethylglutathione dehydrogenase and frmB encodes the S-formylglutathione hydrolase. Note that *E. coli* BL21(DE3) strains contain active formaldehyde dehydrogenase that introduces competition for formaldehyde, suggesting the intracellular formaldehyde is detoxified to $CO_2$ during the course of the experiment. To eliminate formaldehyde competition, all single gene and co-expression constructs were transformed into an *E. coli* ΔfrmA strain using a modified pETM6 vector containing the tac promoter (see Examples 15 and 17 below). While in vivo activity in *E. coli* has been reported previously for five of these MDHs (Bme MGA3 Mdh, Bme MGA3 Mdh2, Bme MGA3 Mdh3, Bme PB1 Mdh, and Bme PB1 Mdh2), the data for in vivo activity in *E. coli* for Bst 2334 Mdh, Bst NUB3621 Mdh, Bme C1 Mdh, and Bme PB1 Mdh1 are new. As presented, Bme MGA3 Mdh2 and Bme MGA3 Mdh3 possess the highest activity in vivo in *E. coli* BL21(DE3) strains while Bst 2334 Mdh and Bme MGA3 Mdh3 possess the highest activity in vivo in *E. coli* ΔfrmA strains. Furthermore, MDH activator proteins do not exhibit a stimulatory effect in vivo when co-expressed with their respective MDHs in *E. coli* BL21(DE3) strains, suggesting the physiological role of these activator proteins within methylotrophic growth remains unknown.

Figure 19:
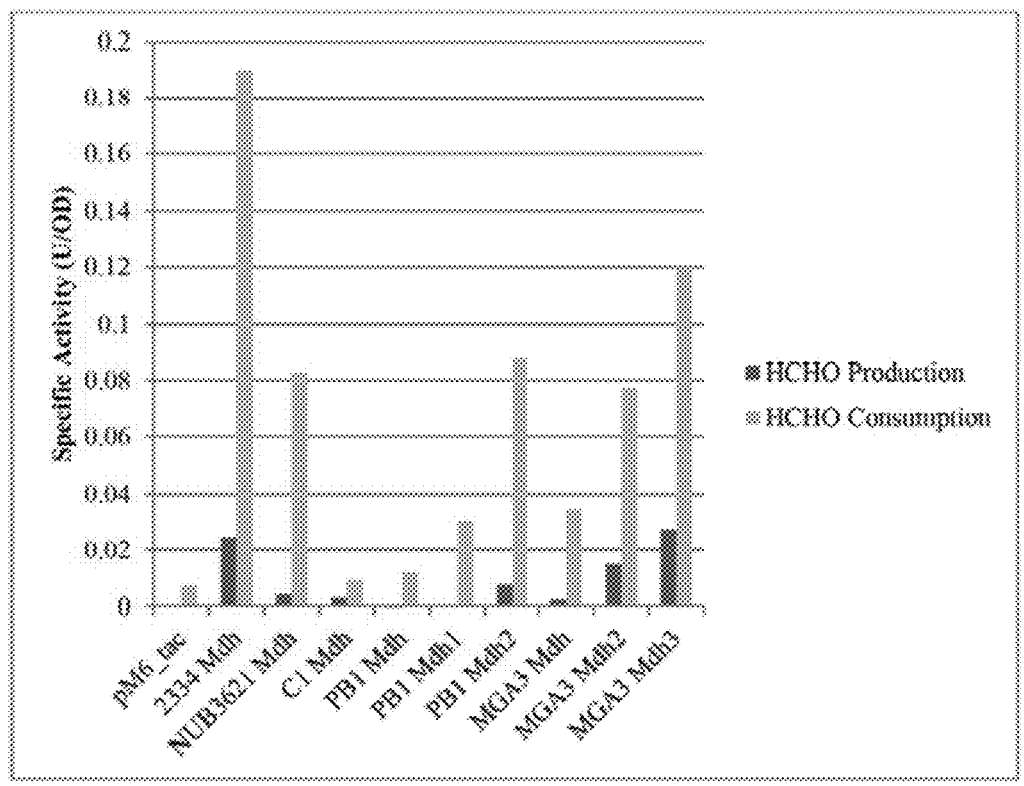
FIG. 19 shows specific activities (calculated from 10 minute time points) for in vivo assays using *E. coli* ΔfrmA MDH strains and either 0.5 M MeOH for MeOH oxidation or 0.5 mM HCHO for HCHO reduction. One unit (U) is defined as µmol HCHO produced or consumed per minute.

In vivo HCHO reductase activity of all MDHs has been examined in addition to methanol oxidation. These data show that the rate of HCHO reduction is greater than that of methanol oxidation (FIG. 19). These results are explained by examining the thermodynamics of the system, which suggests that methanol oxidation is unfavorable under standard conditions ($\Delta_r G=+34.2$ kJ/mol) but becomes slightly favorable under physiological conditions ($\Delta_r G=-1.0$ kJ/mol) as the intracellular HCHO concentration remains at micromolar levels.

Example 11. Optimized Methanol Utilization in One or Sequential Bioreactors with Optimized Temperature for Optimal MDH Activity Thermodynamic calculations show a positive change in reduction potential and negative change in reaction Gibbs free energy when calculated using estimated physiological conditions (Table 2). This suggests that MeOH oxidation via NAD-dependent MDH enzymes becomes more favorable at higher temperatures, i.e., the optimal growth temperature of 45-55° C. of these thermophilic *bacillus* methylotrophs. Specifically, the change in the reaction Gibbs free energy ($\Delta_r G$) decreases from −1.0 to −2.9 kJ/mol as the temperature increases from 37 to 55° C., suggesting a more favorable reaction at higher temperatures. This further demonstrates that MeOH oxidation via NAD-dependent MDH enzymes is plausible under the physiological growth conditions of mesophiles such as *E. coli*. As MeOH oxidation via NAD-dependent MDH enzymes is favorable only to a small extent under physiological conditions compared with the other methanol oxidation systems, the immediate consumption of HCHO via an assimilation pathway will increase the favorability of MeOH oxidation. For example, at 37° C., when the concentration of HCHO is lowered from 0.17 to 0.017 mM, the change in the reaction Gibbs free energy decreases from −1.0 to −7.0 kJ/mol while the equilibrium constant shifts from 0.925 to 8.5, thus becoming much more favorable. Therefore, increased methanol oxidation within synthetic methylotrophic organisms may be achieved by keeping the intracellular HCHO concentration at very low levels, likely through its immediate consumption via a HCHO assimilation pathway.

Figure 20:
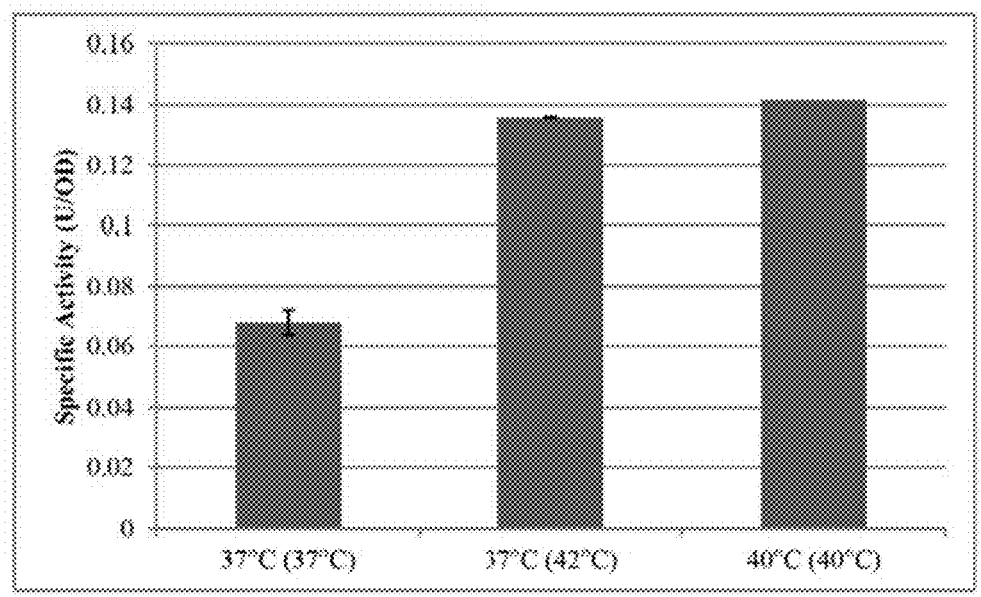
FIG. 20 shows specific activities in an in vivo assay at increased temperatures. Data was obtained from *E. coli* BL21(DE3) pETM6_Bme MGA3 Mdh3 and 1M MeOH. The first temperature represents the growth temperature while the temperature in parentheses represents the temperature at which the assay was performed. One unit (U) is defined as µmol HCHO produced per minute. Error bars represent averages from two biological replicates, except in the case of 40° C. (40° C.), which is from one biological replicate.

For the aforementioned and cloned MDHs, the rate of methanol oxidation increases with increasing temperature. As demonstrated in FIG. 20, the in vivo methanol oxidation rate doubles as the growth temperature is increased from 37 to 40° C. These data support the thermodynamic calculations shown in Table 2 and demonstrate that the rate of methanol oxidation would be increased in an *E. coli* strain adapted for growth at higher temperatures. This is a realistic possibility as has been reported. Thus, we developed cultivation strategies to take advantage of these optimal conditions for MDH activity. *E. coli* strains (WT or mutant strains such as *E. coli* ΔfrmA strains) are developed by evolutionary adaptation to grow at any higher temperature such as 40° C., 45° C. or 50° C. These strains are then used to engineer the methanol utilization pathway described here in combination with any engineered pathway to produce a desirable oxychemical as shown conceptually in FIGS. 1 and 2. The expressed genes are optimized for enzyme expression and activity at the higher temperature. These engineered strains are used either in a single bioreactor operating at a higher temperature (e.g., 40° C., 45° C. or 50° C.), or in reactors in series each operating in a different temperature so that one can separately optimize cell growth and product formation. For example, cells are grown in one reactor at 37° C. and then product is formed in a second bioreactor operating at 40° C., 45° C. or 50° C. One could use three or more bioreactors sequentially or otherwise, each operating at a different temperature.

Example 12. Protein Engineering to Generate Desirable MDH Mutants

Figure 21:
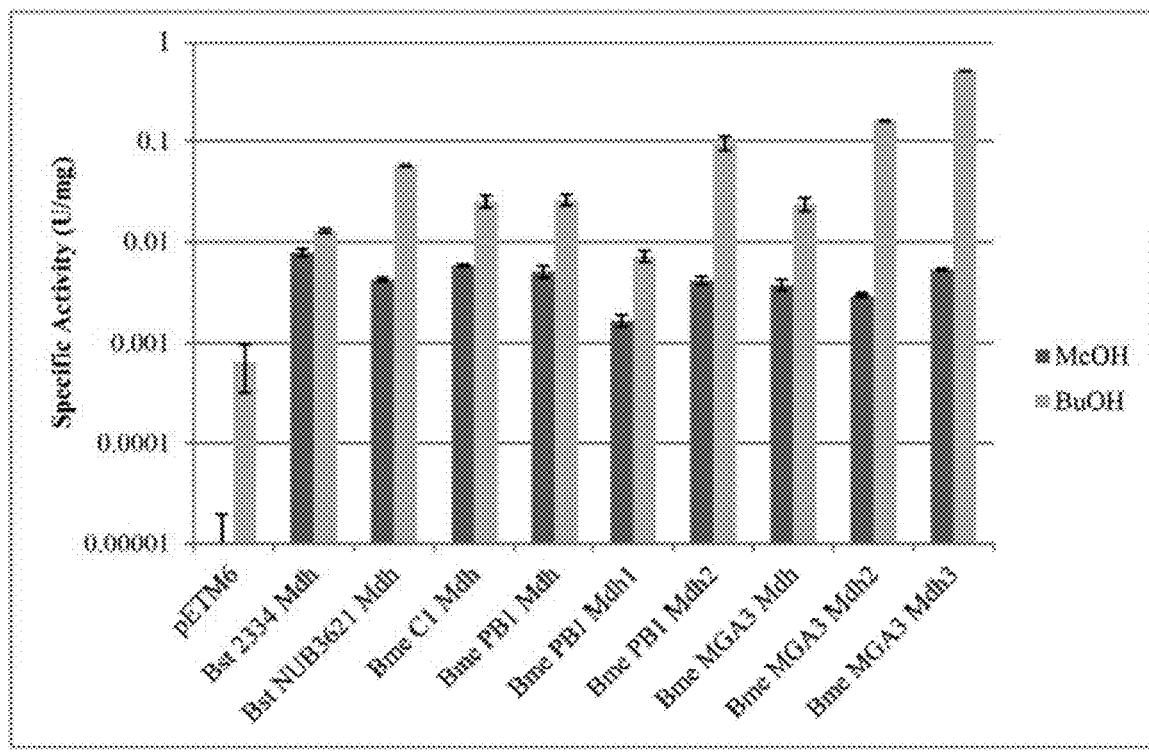
FIG. 21 shows specific activities in an in vitro assay demonstrating that all MDHs possess higher activity towards butanol compared to methanol. As presented, the MDHs exhibit a wide range of alcohol selectivity. 100 mM alcohols were used. One unit (U) is defined as µmol NADH produced per minute. Error bars represent averages from two biological replicates.
Figure 22:
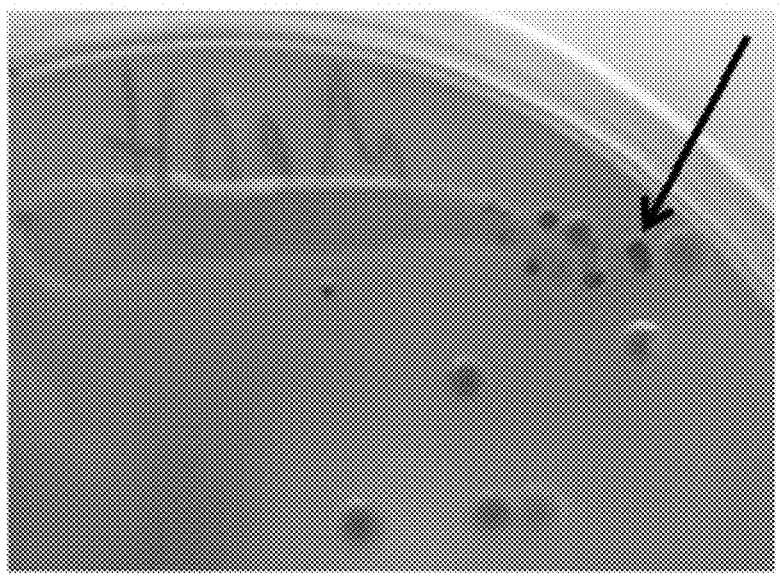
FIG. 22 shows aldehyde indicator plates. *E. coli* BL21 (DE3) containing Bme MGA3 Mdh3 in pETM6 is represented. The arrow indicates a positive colony producing formaldehyde, which appears red via the reaction with pararosaniline and sodium bisulfite.

The chosen MDHs may exhibit a limitation in the context of a desirable product. From our data shown in FIG. 21, all MDHs possess higher activity towards butanol compared with methanol in vitro. So, if the desirable product is butanol this might be a problem. This can be resolved as disclosed here. Our data (FIG. 21) show that the different MDHs exhibit a wide range of alcohol selectivity, suggesting this natural variability could be used in a directed evolutionary protein engineering approach. To eliminate activity and selectivity towards butanol, a protein engineering approach involving successive rounds of DNA shuffling and/or error-prone PCR is performed. Using such protein engineering approaches, for different enzymes (but NOT for MDHs) it has been possible to alter substrate specificity and increase activity towards specific substrates. To accomplish this engineering strategy, an accurate high-throughput screening technique is required. Data for aldehyde indicator plates has yielded positive results to date as illustrated in FIG. 22. These plates contain a mixture of pararosaniline and sodium bisulfite that reacts with aldehydes to form a red color. To date, these plates have only been examined with E. coli BL21(DE3) MDH strains. Better results are to be obtained with E. coli ΔfrmA strains since the formaldehyde generated from methanol oxidation will not have the potential to escape to $CO_2$. As background color presents an issue for these plates, a flow cytometry-based selection approach will be used in place of or in addition to aldehyde indicator plates. Operating of the same principle, i.e., the reaction of aldehydes with pararosaniline and sodium bisulfite, a flow cytometry-based method will select clones having desirable properties. A selection strategy may also be implemented for identifying desirable MDH mutants. For selection, the MDH library would be cloned with formaldehyde assimilation genes, e.g., HPS and PHI, and introduced to a selective pressure such as a minimal media containing only methanol and butanol. Ideally, a mutant with increased methanol oxidation activity that has lost activity towards butanol would be selected for. Furthermore, these MDHs can be used in synthetic methylotrophic strains that are aimed at producing chemical other than higher alcohols, such as fatty acids, biodiesel, organic acids, carboxylic acids, or butanediol.

Figure 23A:
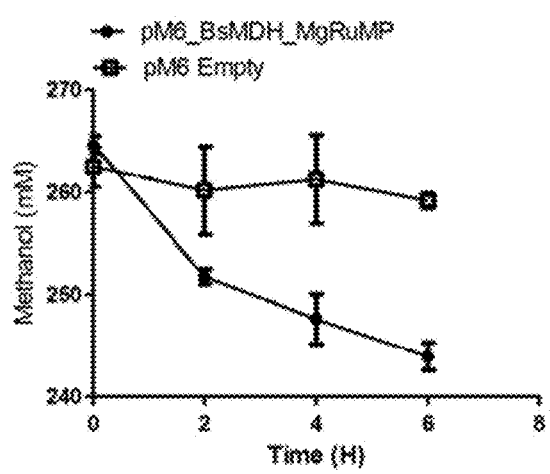
FIGS. 23A-B show growth and methanol consumption by two *E. coli* strains, an empty vector control (pM6 Empty) and a strain expressing the MDH from *B. stearothermophilus* and the RuMP pathway from L3 (pM6_BsMDH_MgRuMP). Both strains were grown to an $OD_{600}$ of 0.4 in LB broth and induced with 1 mM IPTG for 3 hours. The strains were then pelleted, washed, and resuspended in MOPS media containing 1% MeOH and 0.1% glucose and allowed to grow overnight so that the cells could become adapted to the minimal media. The next day the cells were resuspended in MOPS containing 1% MeOH and 0.04% glucose. Glucose was added to the cultures at a concentration of 0.04% every hour and aliquots were taken every two hours for HPLC analysis (A) and changes in $OD_{600}$ (B).
Figure 23B:
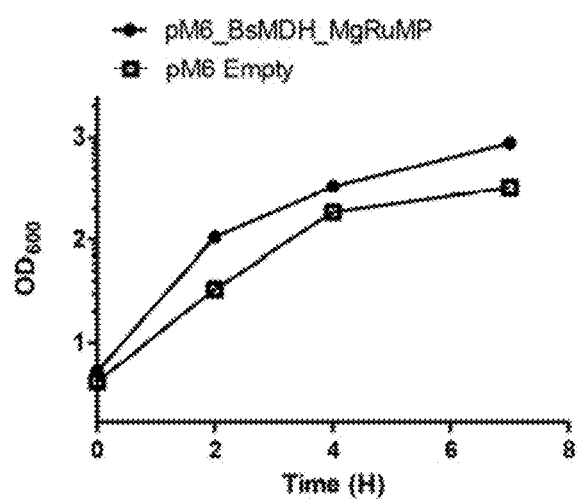

Example 13. Generation of a Methanol Consuming Strain of E. coli with Glucose Present as a Co-Substrate We previously generated a methylotrophic strain of E. coli via expression of a non-native methanol dehydrogenase from B. stearothermophilus in conjunction with the two genes of the ribulose monophosphate (RuMP) pathway: 3-hexulose-6-phosphate synthase (HPS, 2 genes) and 6-phospho-3-hexuloisomerase (PHI) from the methylotroph strain L3 using the pETM6 vector. This strain could grow in media containing methanol and ribose with observed methanol consumption. We have redesigned the vector so that the genes are now in a monocistronic operon configuration as we did not observe robust expression of the MDH protein while in the pseudo-operon configuration. We repeated the growth analysis with this new strain and observed a decrease in MeOH concentration at a rate of approximately 3.5 mM $h^{-1}$, whereas the MeOH concentration in the empty vector control remained fairly unchanged (0.5 mM $h^{-1}$) (FIG. 23A). Both strains exhibited an increase in optical density (OD) at 600 nm in media containing methanol and glucose with the strain expressing MDH and the RuMP pathway reaching a slightly higher OD (FIG. 23B). Because the empty vector control strain was able to grow under these conditions, and because the increase in OD of the strain expressing the recombinant MeOH utilization pathway is just a little greater than the control, we hypothesized that the majority of the MeOH was not going into biomass but was rather dissimilated to $CO_2$ via an endogenous formaldehyde detoxification pathway.

Figure 24:
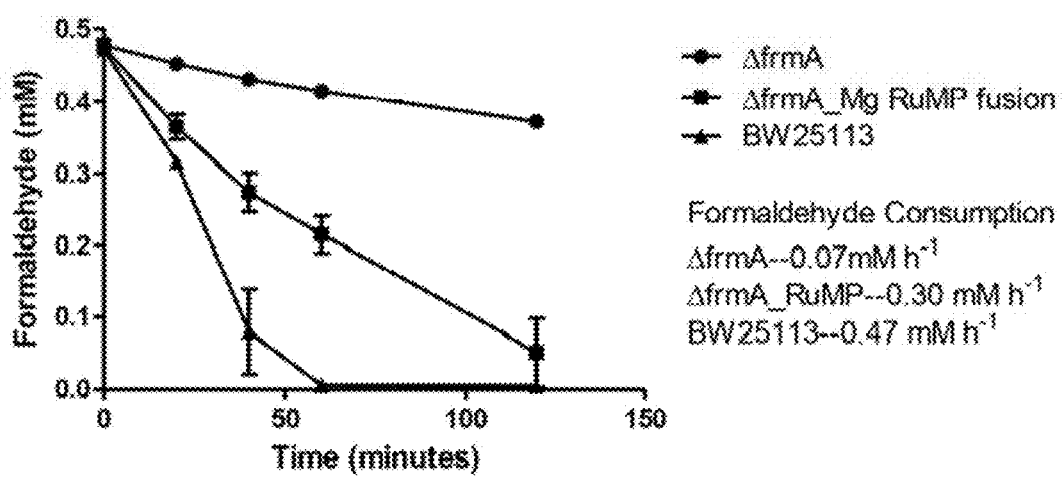
FIG. 24 shows formaldehyde consumption by the native *E. coli* strain BW25113, the ΔfrmA mutant which has a nonfunctional formaldehyde detoxification pathway, and the ΔfrmA mutant expressing the HPS and PHI genes of *M. gastri* (ΔfrmA_MgRUMP fusion). All three strains were grown to mid-log phase ($OD_{600}$ of 0.4). At this time, 1 mM IPTG was added to the cultures and they were allowed to grow for an additional 3 hours. The cultures were then washed with MOPS and resuspended to an $OD_{600}$ of 0.5 In fresh MOPS buffer containing 0.5 mM formaldehyde. Aliquots were taken at 0, 20, 40, 60, and 90 minutes to determine formaldehyde concentration using the NASH reagent.

Example 14. Deletion of the Native System for Formaldehyde Oxidation to Enable Better Strain Engineering In order to achieve a strain capable of consuming methanol as a carbon- and energy-source, we ordered a frmA deletion strain of E. coli from the Keio collection, which disabled the native E. coli formaldehyde detoxification system (FrmRAB). We grew the ΔfrmA strain, the isogenic wild type BW25113, and a ΔfrmA strain expressing the M. gastri HPS-PHI fusion gene on pUC19 (ΔfrmA/pUC_Mgfusion) in medium containing formaldehyde, and followed the disappearance of formaldehyde. We found that the wild-type strain exhibited robust detoxification of formaldehyde at a rate of approximately 0.47 mM $h^{-1}$. In contrast, the ΔfrmA strain was essentially unable to detoxify formaldehyde (0.07 mM $h^{-1}$). The ΔfrmA/pUC_Mgfusion strain was able to consume formaldehyde at a rate of 0.3 mM $h^{-1}$ (FIG. 24). This data confirm the hypothesis that the native E. coli FrmAB genes are very efficient at dissimilating formaldehyde and are likely able to outcompete the recombinant RuMP genes. Thus, we use the ΔfrmA strain as the host strain for the recombinant MeOH pathway for all future experiments and strain developments.

Figure 25:
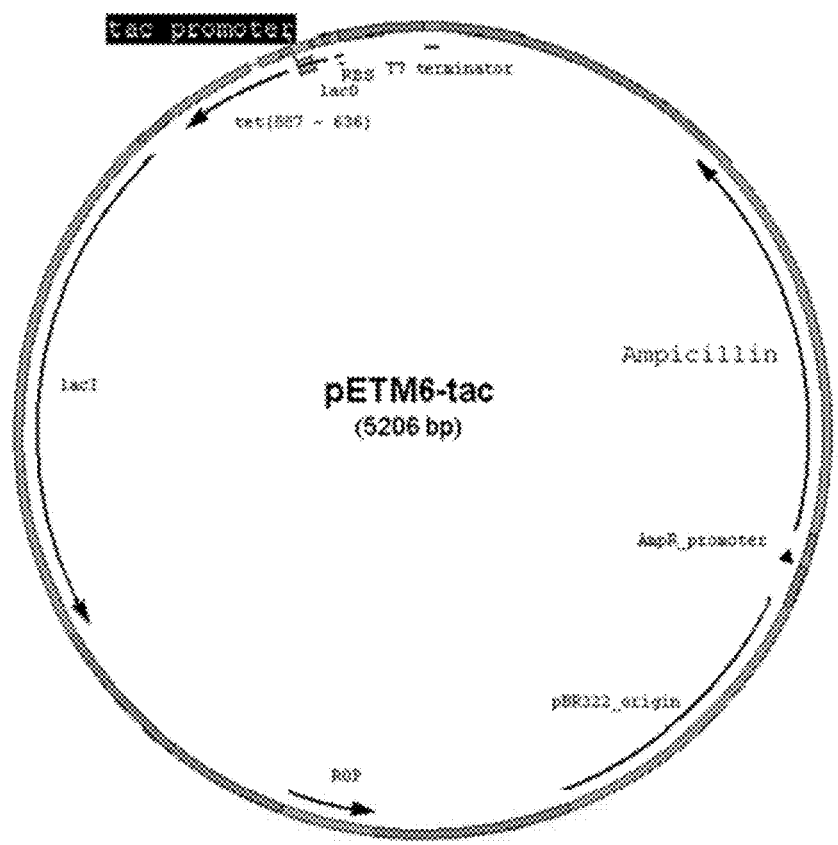
FIG. 25 shows the pETM6-tac vector which will be used in a cloning strategy. The ePathBrick set of vectors (pCDM4, pACM4, pETM6) were modified by replacing the T7 promoter with the inducible tac promoter while keeping all other functional portions of the ePathBrick vectors, including the isocaudamer cloning sites.

Example 15. Expression Based on the Inducible Tac Promoter to Facilitate Regulated Gene Expression for Optimal Pathway Engineering The pETM6 vector is part of the Biobricks family of vectors that relies on isocaudomer pairs to sequentially add genes in a pathway to the vector. In order to continue to make use of this vector for cloning and expressing multiple genes on a single plasmid, we must now account for the fact that the ΔfrmA does not carry the gene for the T7 polymerase and is thus incompatible with the T7 promoter. Therefore, we have redesigned these vectors to contain the tac promoter instead, which would allow for robust IPTG inducible gene expression in the ΔfrmA host strain (FIG. 25).

Example 16. Engineering a Formaldehyde-Inducible Promoter System in E. coli

The RuMP pathway relies on the pentose phosphate pathway for the regeneration of the ribulose-5-phosphate needed to act as the acceptor for formaldehyde fixation. In E. coli, the pentose phosphate pathway is primarily regulated by the availability of reducing equivalents (NAD+/NAHD) whereas in methylotrophic organisms, the pentose phosphate pathway is regulated by the presence of formaldehyde. Therefore, we sought to identify and use a promoter that can respond to formaldehyde to the genes of the E. coli pentose phosphate pathway which will ensure the cells maintain an appropriate ribulose-5-phosphate pool. It has previously been determined that the frmRAB operon responds to increasing formaldehyde concentration indicating that E. coli should contain a native formaldehyde inducible promoter and all the machinery required to transcribe it.

Figure 26:
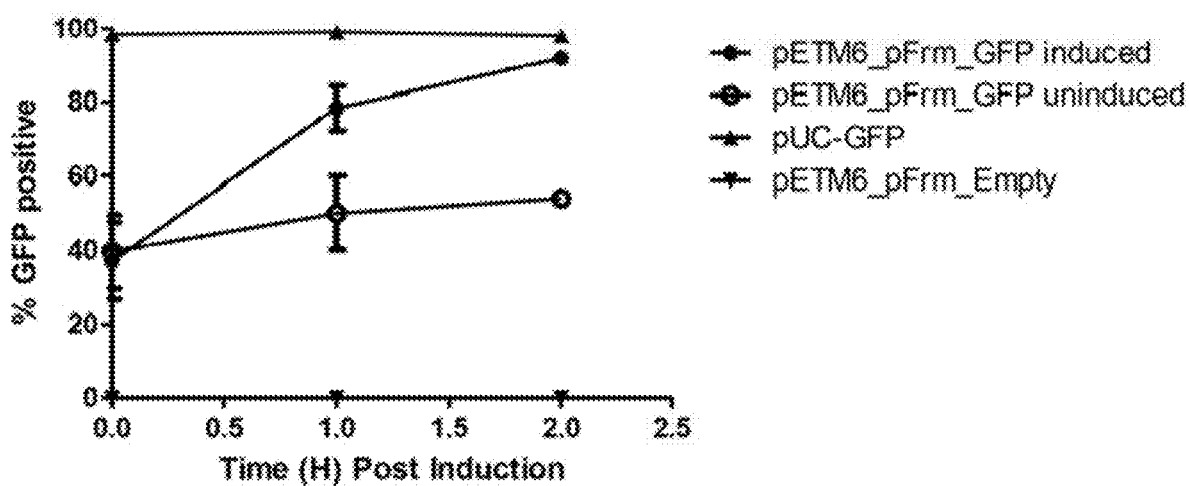
FIG. 26 shows formaldehyde inducible gene expression in *E. coli*. The pETM6 T7 promoter was replaced by the 200-bp region upstream of the frmRAB operon and assayed to see if this region contained a promoter that responds to increasing formaldehyde. GFP was cloned into the multiple cloning site of the vector. Cultures of this strain were grown in LB to mid-log phase ($OD_{600}$ of 0.4) and were either induced with 0.5 mM formaldehyde or left uninduced. Aliquots were taken immediately prior to induction, 1 hour, and 2 hours post-induction with formaldehyde, and analyzed for GFP expression using a flow cytometer. pUC-GFP served as a positive control for GFP expression (induced with 1 mM IPTG) and a strain containing pETM6_pFrm_empty served as a negative control.

To examine this, we removed the T7 promoter from the pETM6 vector and replaced it with the 200 bp region directly upstream of the frmRAB operon. We then cloned GFP into the multiple cloning site of the vector and transformed this new vector (pETM6_pFrm_GFP) into a generic cloning strain of *E. coli*. This strain was induced with formaldehyde or left uninduced and analyzed for GFP expression. GFP could be detected in the induced and uninduced cultures of pETM6_pFrm_GFP at the initial time point. The amount of detectable GFP increased for the cultures that were induced by formaldehyde and remained constant for the uninduced strains (FIG. 26). There are two possibilities for being able to detect GFP in the uninduced cultures: 1) the frmRAB promoter could be leaky, thus leading to GFP expression, or 2) there is a small amount of endogenous formaldehyde present in the cytosol of bacteria which leads to a small amount of expression from the promoter. However, we were able to detect robust expression of GFP after induction with formaldehyde. Therefore, this promoter responds to formaldehyde and can be used to upregulate the pentose phosphate pathway and other genes that might be necessary for growth using C1 carbon sources, since formaldehyde will always be present in the strain oxidizing methanol to formaldehyde.

Example 17. Metabolic Engineering to Enable *E. coli* to Grow Effectively on MeOH as Sole Carbon Source

Figure 27A:
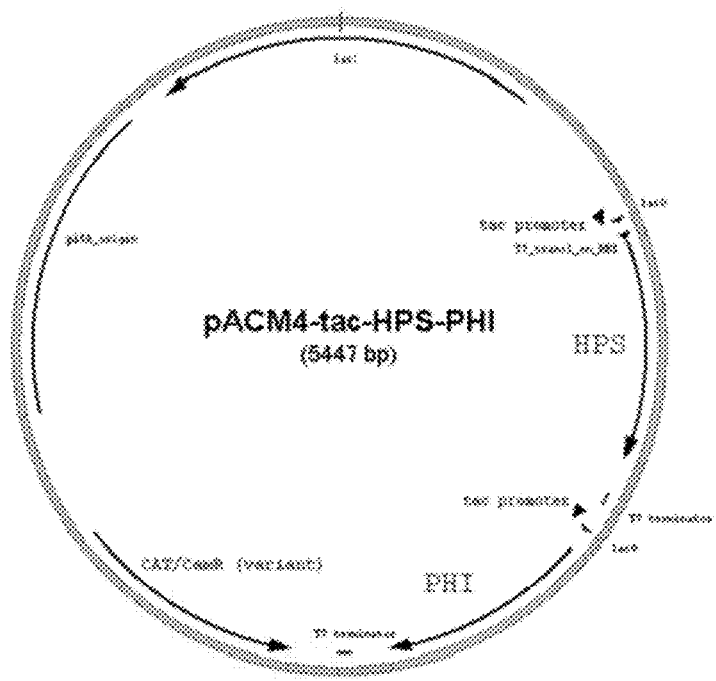
FIGS. 27A-B show A) pACM4 vector and B) pETM6 vector for cloning genes driven by the inducible tac promoter.
Figure 27B:
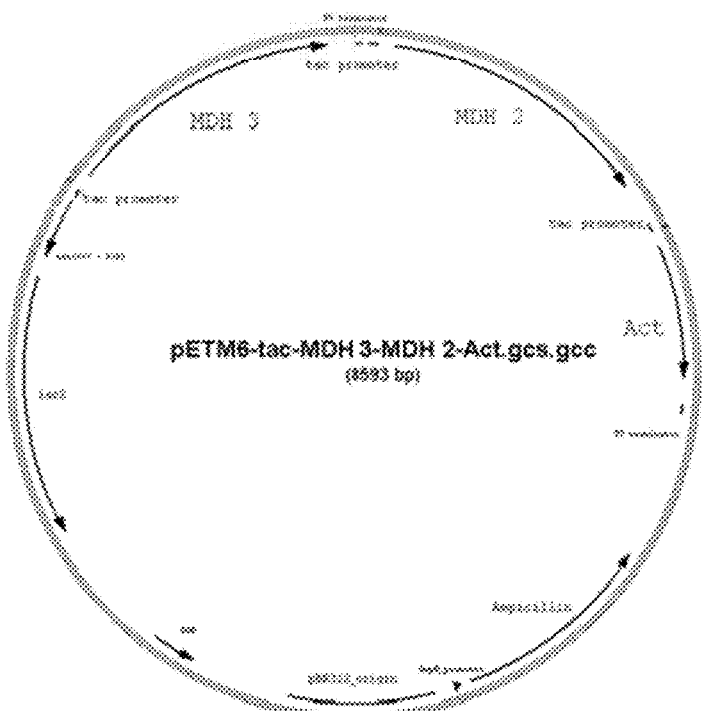

*E. coli* BW25113 and JW0347-1 were grown using methanol as the sole carbon source. Codon-optimized methanol dehydrogenase genes (coding for MDH 2 and MDH 3) from *Bacillus methanolicus* MGA3 were cloned with and without the corresponding activator gene into a modified pETM6 ePathBiobrick vector with the T7 promoter replaced by the tac promoter (pETM6-tac), enabling use in any *E. coli* host strain (FIG. 27). Codon optimized hexulose phosphate synthase gene (coding for HPS) and codon optimized hexulose phosphate isomerase gene (coding for PHI) from *M. gastri* were cloned into a modified pACM4 ePathBiobrick vector with the T7 promoter replaced by the tac promoter (pACM4-tac). The codon optimized HPS and PHI were cloned in a monocistronic orientation (FIG. 27). Two fusion HPS and PHI genes, from *M. gastri* and strain L3, were cloned in pACM4-tac as well (FIG. 27). pETM6-tac and pACM4-tac have compatible origins of replication and different antibiotic resistance markers, enabling co-transformation. These constructs containing an MDH gene and the HPS and PHI genes, when co-transformed, enabled sustained growth on methanol in minimal medium.

Example 18. Employing a Mutation-Directed Evolution Selection Strategy on Methylotrophic *E. coli* Yields Fast Growing Methanol Consumer

*E. coli* BW25113 and JW0347-1 containing plasmids with genes encoding the HPS and PHI genes or a combination of MDH, HPS, and PHI genes were mutated using the chemical NTG (n-methyl-n'-nitro-n-nitrosoguanidine). These populations of mutants were allowed to recover and then transferred to a selection of minimal medium with formaldehyde or methanol as the sole carbon source. Growth was observed over multiple generations and serial transfers. Individual mutants were isolated and screened for improved growth. Multiple mutants were found to have superior growth rates and higher cell densities when grown on methanol or formaldehyde compared to their parent strain.

Example 19. Demonstrating Functionality of the Engineered RuMP-Based Methylotrophic Pathway by Showing Incorporation of Carbon from Formaldehyde into Biomass Components and Alter $CO_2$ Production Using $^{13}C$ Labeling and Flux Analysis Using $^{13}C$-labeled substrates, we can determine how effective these new pathways are by examining the extent of incorporation of these substrates. Experiments were performed with four *E. coli* strains:
  i. an unmodified *E. coli* strain containing an empty vector (pM6; control)
  ii. an unmodified *E. coli* strain containing a pUC19 vector expressing the *M. gastri* RuMP fusion genes.
  iii. The ΔfrmA *E. coli* strain where as described above the native formaldehyde oxidation system has been inactivated.
  iv. The ΔfrmA *E. coli* strain containing a pUC19 vector expressing the *M. gastri* RuMP fusion genes.

Cultures were inoculated at an $OD_{600}$ of 0.500 in minimal MOPS media with 0.5 mM $^{12}C$-formaldehyde, as an unlabeled control, or $^{13}C$-Formaldehyde. After 2 hours, the same amount of formaldehyde was added again to each sample. After 4 hours, the headspace gas was analyzed by mass spectrometry. The formaldehyde concentration in the media was quantified and biomass samples were analyzed for labeling in intracellular metabolites by GC-MS.

Figure 28:
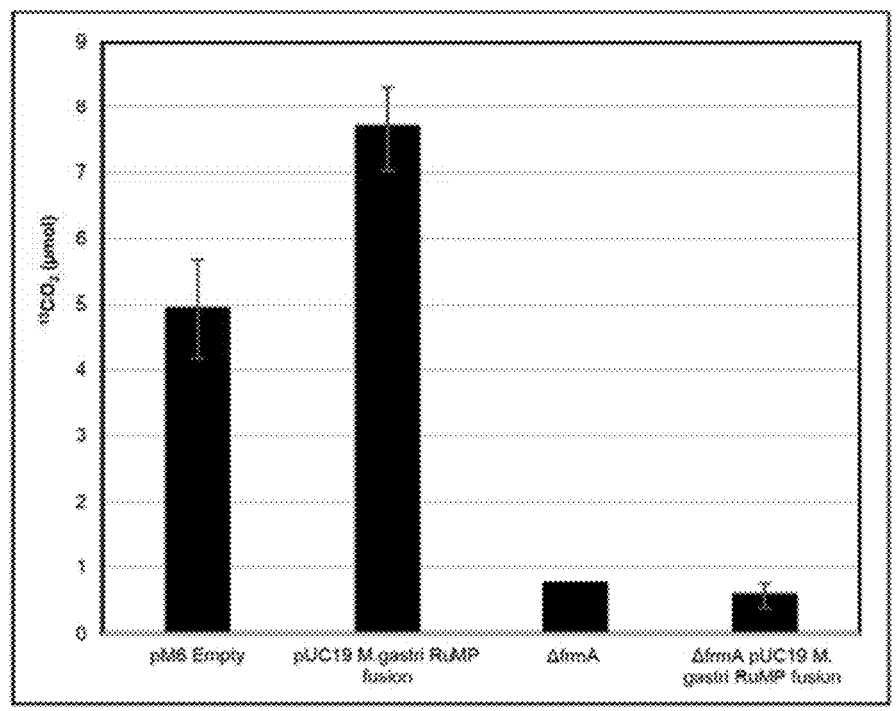
FIG. 28 shows the amount of $^{13}CO_2$ in the headspace after 4 hours of cultures grown with $^{13}$C-Formaldehyde.
Figure 29:
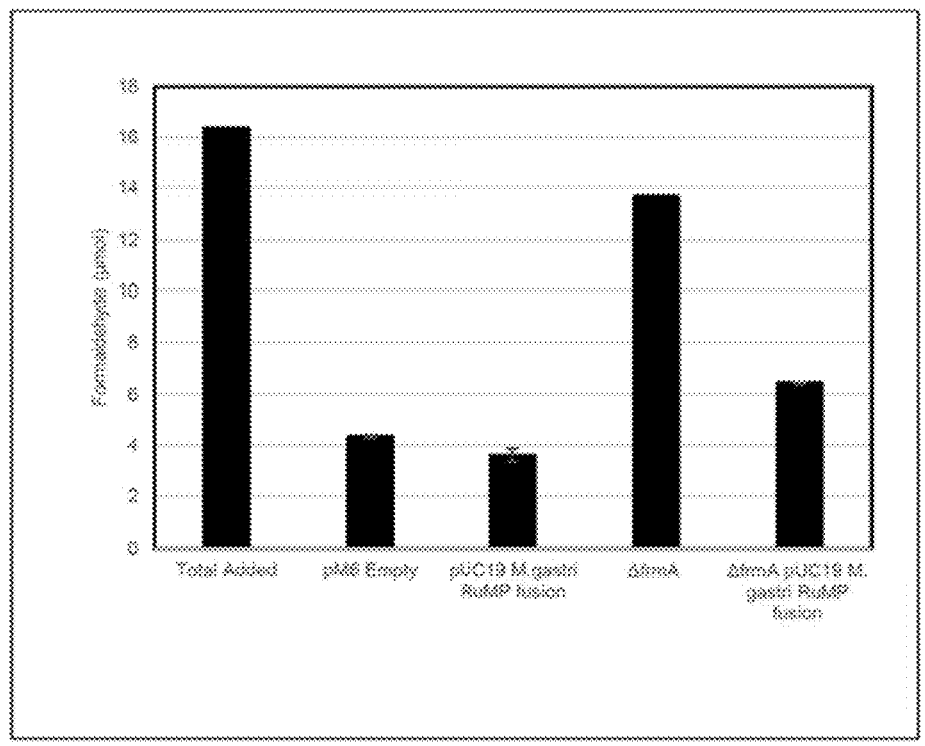
FIG. 29 shows the amount of formaldehyde in media after 4 hours of cultures grown with $^{13}$C-Formaldehyde.
Figure 30:
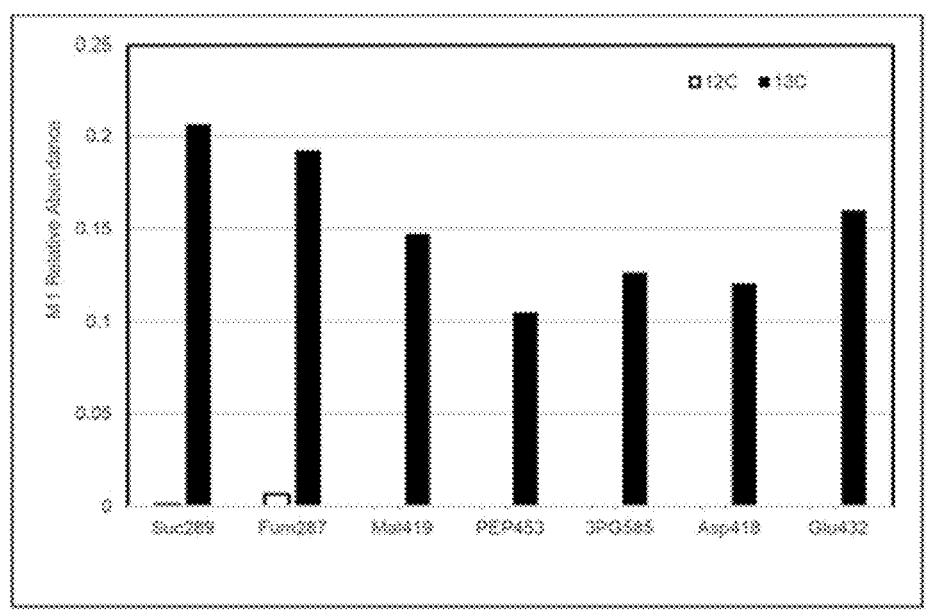
FIG. 30 shows $^{13}$C-labeling of metabolites in central carbon metabolism. Suc289—Succinate. Fum287—Fumarate. Mal419—Malate. PEP453—Phosphoenolpyruvate. 3PG585—3-phosphoglycerate. Asp418—Aspartate. Glu432—Glutamate
Figure 31:
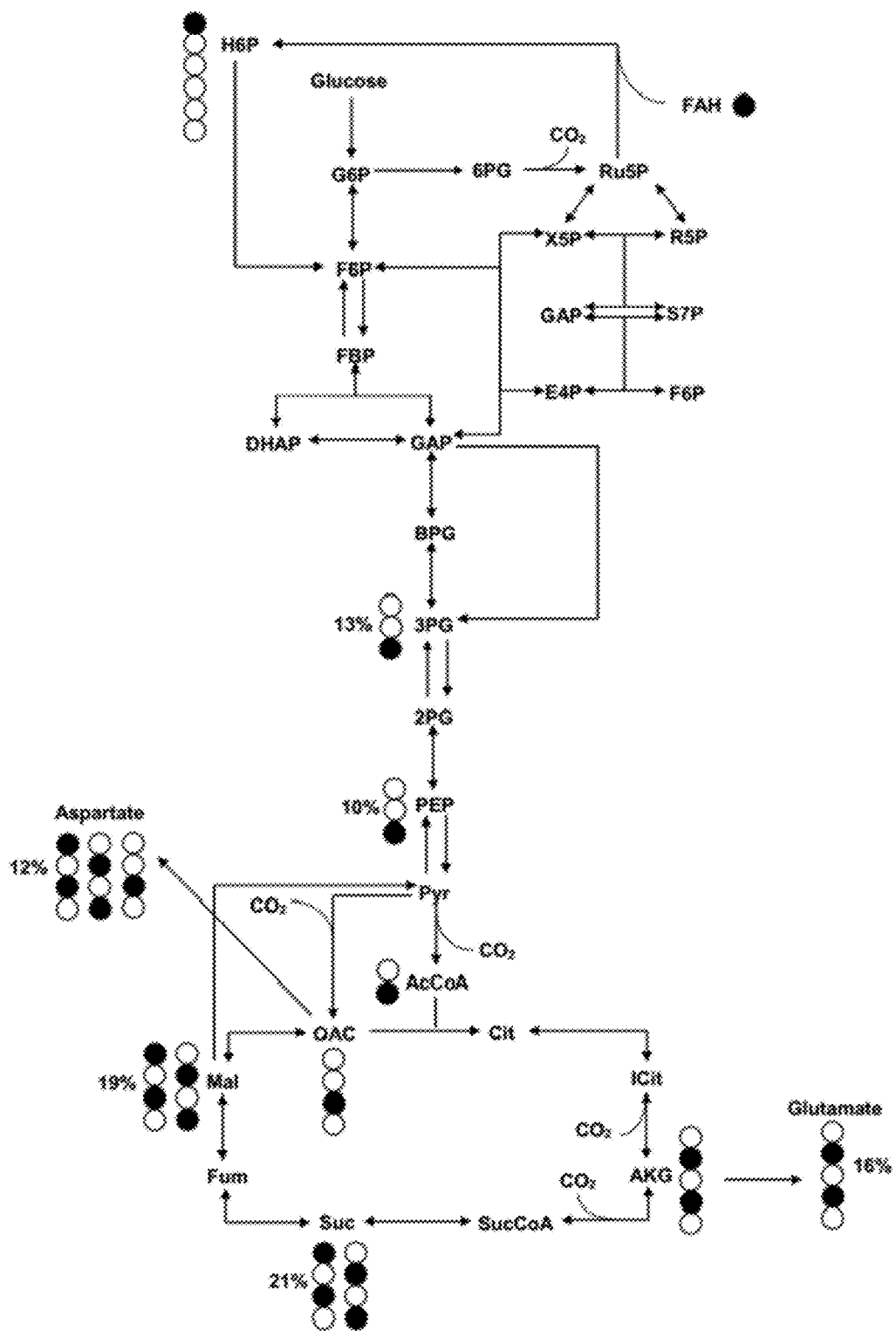
FIG. 31 illustrates the expected labeling patterns using labeled formaldehyde. The black circles are labeled carbons and the white circles are unlabeled carbons. Percentages are the relative abundance of M+1 labeled fragments (FIG. 17). The RuMP pathway is represented by the arrows.

FIG. 28 shows the amount of labeled carbon dioxide in the headspace, while FIG. 29 shows the formaldehyde left in the media. The amount of formaldehyde utilized and $CO_2$ produced from formaldehyde oxidation was high in the unmodified *E. coli* strains. In contrast, in the ΔfrmA *E. coli* strain, very little formaldehyde was utilized and very little $CO_2$ was produced, as would be expected. In the ΔfrmA *E. coli* strain expressing the *M. gastri* RuMP fusion genes, a good amount of formaldehyde was utilized, yet very little $CO_2$ was produced, thus suggesting that formaldehyde utilization did not result in oxidation to $CO_2$ but rather its incorporation into biomass. To support further this conclusion, FIGS. 30 and 31 show the extent of labeling from $^{13}C$-formaldehyde into key metabolites of the central carbon metabolism. Compared to the unlabeled controls, the data show that $^{13}C$-formaldehyde is being highly incorporated into these metabolites, and thus very little formaldehyde is oxidized into $CO_2$. This shows that the engineered RuMP pathway is functional and capable of incorporating carbon from C1 compounds at the oxidation state of formaldehyde.

Example 20. Metabolic Engineering to Make *E. coli* Fix $CO_2$ when Growing on MeOH In order to engineer *E. coli* to fix $CO_2$ when growing on MeOH, we explore the scheme where $CO_2$ is reduced to formate and subsequently to formaldehyde through the reverse activity of a formate dehydrogenase (FDH) and a formaldehyde dehydrogenase (FLD), respectively. The co-expression of a carbonic anhydrase (CA) is also employed to increase the availability of $CO_2$ within the bacterial cells.

A. Formate Dehydrogenase Expression

In our invention the $CO_2$ fixation route starts with the conversion of $CO_2$ to formate through a reversed formate dehydrogenase activity. In this context we explore heterologous expression of the *Moorela thermoacetica* (Moth) FDH-A subunit and FDH-B subunit in *E. coli*. We have designed a hybrid cDNA sequence that is both codon-optimized for *E. coli* expression, as well as has a substituted Clostridia SECIS element with a potential *E. coli* recognizable one.

The final optimized sequence for higher expression levels of the Moth FDH-A in *E. coli* with the artificially designed SECIS element designed by DNA2.0 is shown in FIG. 32A (SEQ ID NO: 1).

The SECIS substitution resulted in a modified ORF with two amino-acid changes (highlighted in bold and underlined letters) in the encoded protein (Table 3).

For the previously mentioned $CO_2$ fixation scheme, we also test a different formate dehydrogenase that does not have a selenocysteine as part of its active site. For that we designed a codon-optimized *Candida boindini* formate dehydrogenase for over-expression in *E. coli*. The optimized sequence designed by Genscript is shown in FIG. 32B (SEQ ID NO: 2).

The *C. boidini* formate dehydrogenase is cloned into pACYC-Duet-1 vector that allows overexpression under the IPTG inducible T7 promoter.

Moth DNA2.0 designed FDH-A is cloned into pCOLA-Duet-1 vector together with FDHB designed from Genscript, in order to achieve co-expression of the two subunits (FDH-A, FDH-B) proteins that constitute the active form of the Moth formate dehydrogenase protein complex.

The reversibility of the enzymatic activity in both cases is checked in vivo according to the assay:

(a) Start culture and incubate at 37° C. overnight in LB media. Inoculate fresh TB media and incubate until $OD_{600}$=1-2. Spin down the bacteria at 4000 g for 10 min at 4° C.;

(b) Resuspend bacterial pellet in minimal media (M9, MOPS) supplemented with glucose or glycerol;

(c) Induce with 0.2-1 mM IPTG and transfer the culture into serum bottles to be cultivated anaerobically;

(d) After 1-2 hours of incubation at 37° C. add 1 mM methyl-viologen to maintain the media reduced;

(e) Addition of sodium bicarbonate to provide the substrate for the in vivo activity; and (f) Let the culture grow at 37° C., sample at 1-18 h and test for protein expression, formate and formaldehyde concentration.

B. *E. coli* Strain BL21 (DE3) by knocking Out the Native Operon Responsible for Formaldehyde Detoxification (frmRAB)

In bacteria the detoxification of the highly toxic formaldehyde is essential for survival. The formaldehyde detoxification pathway has been characterized in *E. coli* and is found to involve a glutathione (GSH)-dependent NAD-linked formaldehyde dehydrogenase (GSH-FDH) and a formyl-GSH hydrolase (FGH). In more detail, formaldehyde spontaneously reacts with GSH to produce S-hydroxymrth-ylglutathione, which is then oxidized to S-formylglutathione by formaldehyde dehydrogenase. In *E. coli* the enzymes that perform the formaldehyde degradation are encoded by a three gene operon namely, fmrRAB. frmR encodes a transcriptional repressor of the operon, frmA encodes the S-hydroxymethylglutathione dehydrogenase and frmB encodes the S-formylglutathione hydrolase.

In order to test the reversibility of formate dehydrogenase and formaldehyde dehydrogenase in vivo, the formaldehyde detoxification pathway has to be eliminated because it dominates the fate of any formaldehyde produced into the engineered bacterial system. For that reason, we designed an experiment to knock-out the frmRAB operon in *E. coli* BL21(DE), the strain we routinely use for T7 promoter driven, IPTG-inducible protein overexpression.

The sequence of frmRAB operon in *E. coli* BL21(DE3) is shown in FIG. 32C (SEQ ID NO: 3).

The PCR-based process used includes a one-step inactivation of the three chromosomal genes as described by Datsenko et al, 2000 (PNAS 97(12): 6640-6645). The primers used that have 40-nt extensions are homologous to the regions adjacent to the frmAB operon (underlined) are the following:

H1P1:
(SEQ ID NO: 6)
<u>ATATAGCATACCCCCCTATAGTATATTGCGTGCAGATAATGAGGTGCGAA</u>
ATTCCGGGGATCCGTCGACC

H2P2:
(SEQ ID NO: 7)
TGTAGGCCGGATAAGGCGTTCACGCCGCATCCGGCAGTCGTGCACTATTA
TGTAGGCTGGAGCTGCTTCG

The rest of the primer sequence will anneal to the pKD46 plasmid to amplify a kanamydn resistant cassette. The resulted PCR amplified fragment is then introduced into the BL21 strain already transformed with the lamda-phage Red recombinase carrying plasmid (pKD13). This allows a recombination event where the frmRAB operon is substituted with the kamamycin cassette and thus eliminated from the strain's chromosomal DNA. Introduction of the PCR20 vector into the kanamycin resistant strain eliminates the kanamycin cassette through a final recombination event. The engineered BL21 strain is expected to have significantly reduced levels of formaldehyde detoxification which will allow more precise in vivo activity measurements for the formate dehydrogenase and formaldehyde dehydrogenase overexpressing strains.

Example 21. Expression of MDHs in *E. coli* and their In Vivo Activity

Figure 33:
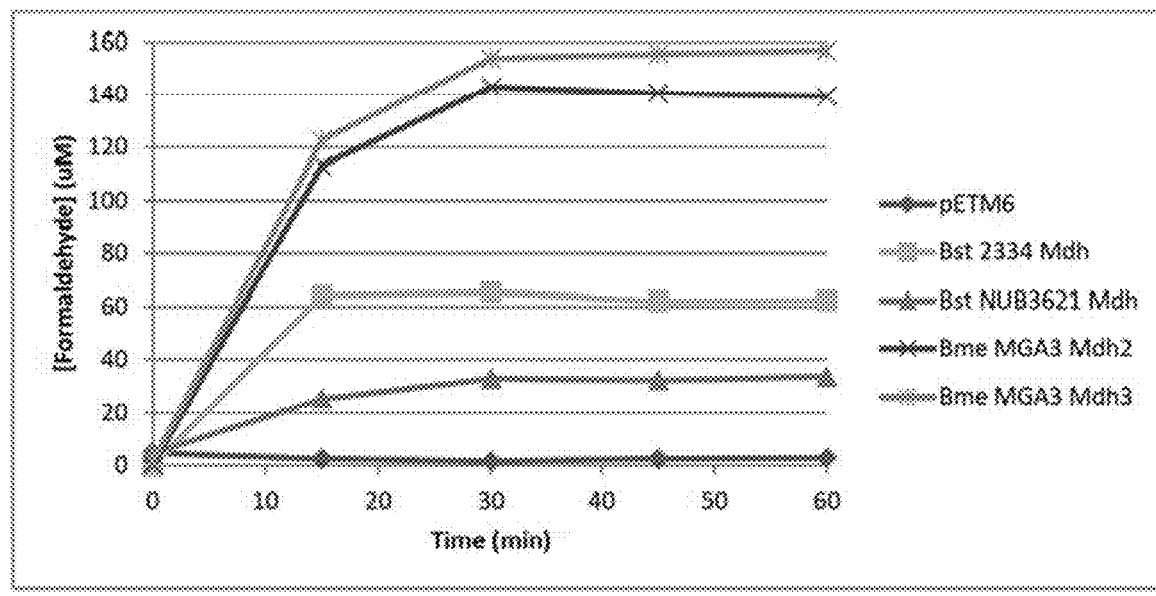
FIG. 33 shows MDH candidates possessing in vivo activity. All nine MDH candidates were assayed in vivo; only those resulting in detectable activity are shown for clarity. pETM6 represents the empty vector control.
Figure 34:
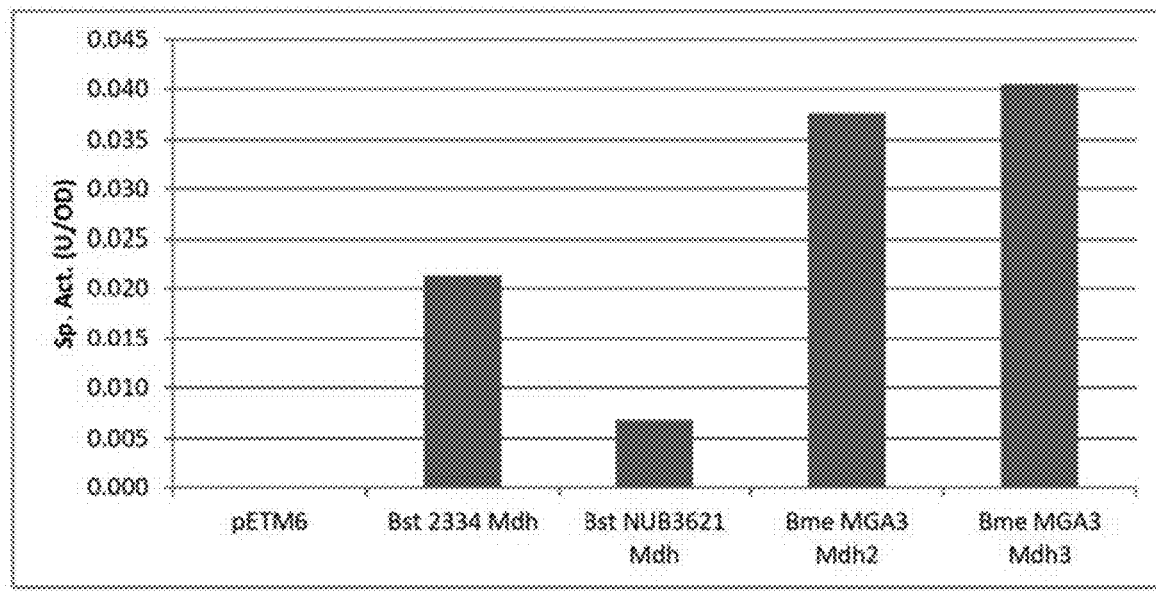
FIG. 34 shows specific activities calculated from initial reaction rates of FIG. 33. One unit (U) is defined as the μmol of formaldehyde produced per minute.
Figure 35:
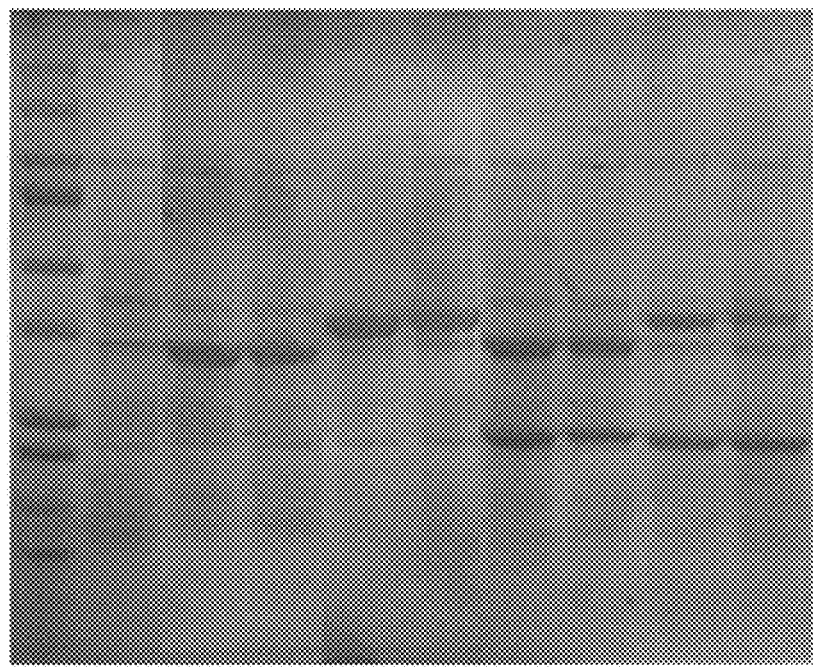
FIG. 35 shows protein expression of MDH and ACT in recombinant *E. coli* strains. Lanes: 1) Marker, 2) pETM6 empty vector, 3) Bst 2334 Mdh, 4) Bst NUB3621 Mdh, 5) Bme MGA3 Mdh2, 6) Bme MGA3 Mdh3, 7) Bst 2334 Mdh+Bst NUB3621 Act, 8) Bst NUB3621 Mdh+Bst NUB3621 Act, 9) Bme MGA3 Mdh2+Bme MGA3 Act, 10) Bme MGA3 Mdh2+Bme MGA3 Act. Bst MDHs are 36.2 kDa, Bme MDHs are 40.7 kDa, and ACTs are 21 kDa.

Nine $NAD^+$-dependent MDH candidates are listed in Table 4. All of the enzymes were codon optimized for *E. coli* except for *Bacillus stearothermophilus* (Bst) 2334 and cloned into the pETM6 expression vector, which were subsequently transformed into *E. coli* Rosetta expression strains. Of the nine enzymes, only Bst 2334 Mdh, Bst NUB3621 Mdh, *Bacillus methanolicus* (Bme) MGA3 Mdh2, and Bme MGA3 Mdh3 possess detectable activity in vivo compared to the pETM6 empty vector control strain as presented in FIG. 33. The in vivo assay was performed as follows: cultures were first grown in LB media at 37° C. to an optical density of 0.4, where protein expression was induced with 0.5 mM IPTG and allowed to proceed for 3 hours at 37° C. After expression was complete, cells were harvested and normalized in M9 media to an optical density of 2. The reaction was initiated with 1M methanol, and formaldehyde accumulation in the supernatant was monitored over a one hour span using the method adopted by Nash (Biochemical Journal 55(3): 416-421). Based on specific activities calculated from initial reaction rates, which is presented in FIG. 34, it appears that the Bme MGA3 MDH enzymes are best. Although co-expression of the respective ACT proteins with each MDH enzyme was achieved (see FIG. 35), the stimulatory effect of ACT was not observed in vivo as specific activities of co-expression cultures were less than those of corresponding single MDH expression strains.

To sum, a total of nine $NAD^+$-dependent MDH enzymes were identified from thermophilic *Bacillus* spp.; of these, only four possess detectable activity in vivo in recombinant *E. coli* strains. These four MDH candidates are Bst 2334

Mdh, Bst NUB3621 Mdh, Bme MGA3 Mdh2, and Bme MGA3 Mdh3. Although ACT stimulates MDH activity in vitro, co-expression of ACT with the MDH enzymes decreased specific activity in vivo rather than stimulating it.

Example 22. Protein Engineering of MDHs to Enhance Substrate Specificity and Optimal Activity Temperature As discussed, NAD$^+$-dependent MDH enzymes possess higher activity and specificity for butanol than methanol. Through protein engineering, this limitation may be alleviated. Along with increasing activity and specificity for methanol, protein engineering can be also used for increasing MDH activity at 37° C. since the thermophilic *Bacillus* spp. from which they are derived have optimal growth temperature above 45° C.

Example 23. Generation of a Methanol Consuming Strain of *E. coli*

We first generated a methylotrophic strain of *E. coli* via expression of a non-native methanol dehydrogenase in conjunction with the two genes of the ribulose monophosphate (RuMP) pathway: 3-hexulose-6-phosphate synthase (HPS) and 6-phospho-3-hexuloisomerase (PHI). To achieve this, we combined the *B. stearothermophilus* MDH with the HPS (2 genes) and PHI from the methylotroph strain L3 (Chu and Papoutsakis, Biotechnol. Bioeng. 29(1): 55-64) using the pETM6 vector. The pETM6 vector is part of the Biobricks family of vectors that relies on isocaudomer pairs to sequentially add genes in a pathway to the vector. Briefly, the *B. stearothermophilus* gene along with the 3 genes comprising the L3 RuMP pathway were amplified by PCR and cloned separately into the pETM6 vector at NdeI and XhoI sites. Single gene-containing vectors were then digested with SalI and AvrII for donor vectors or SalI and SpeI for receiving vectors. The SalI and AvrII fragment contained the T7 promoter along with the gene of interest and was subsequently ligated to the pETM6 linearized by SalI and SpeI. This ultimately culminates in a vector containing all 4 genes, each with their own T7 promoter and a single terminator of the set of genes (pseudo-operon conformation).

Example 24. Growth Analysis Utilizing Methanol as a Carbon and Energy Source

Figure 36:
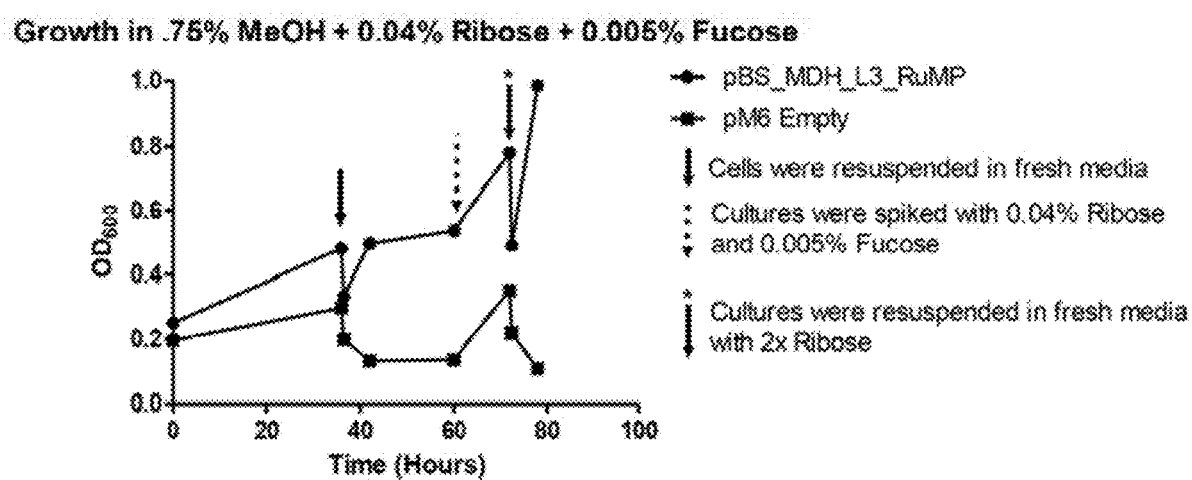
FIG. 36 shows growth of *E. coli* in M9 media plus methanol. Induced cells were resuspended in M9 media supplemented with 0.75% methanol, 0.04% ribose and 0.005% fucose. Growth was monitored by optical density.
Figure 37A:
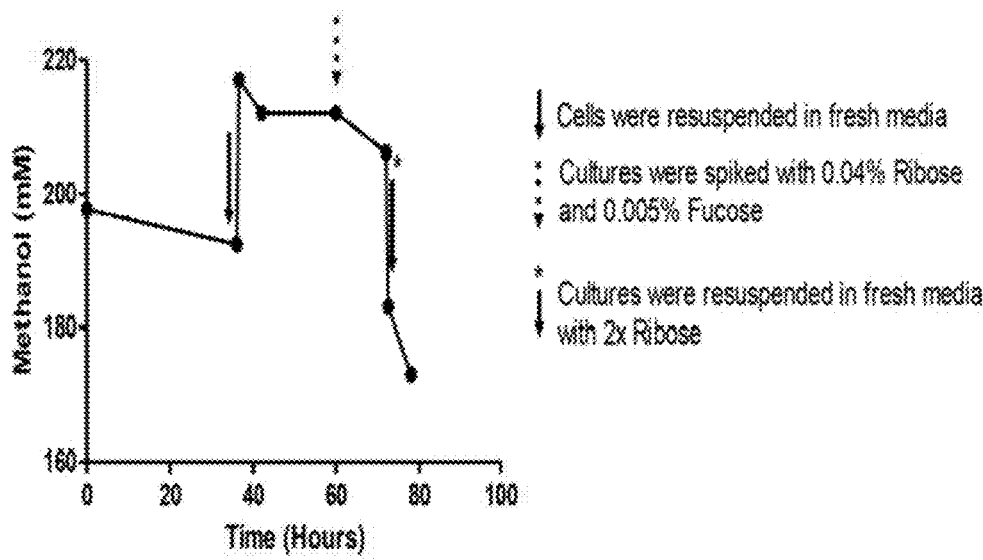
FIGS. 37A-B show methanol consumption by *E. coli* BL21(DE) containing either (A) pETM6_Bs_MDH_L3RuMP or (B) pETM6_Empty. HPLC analysis of culture supernatants was used to monitor methanol consumption.
Figure 37B:
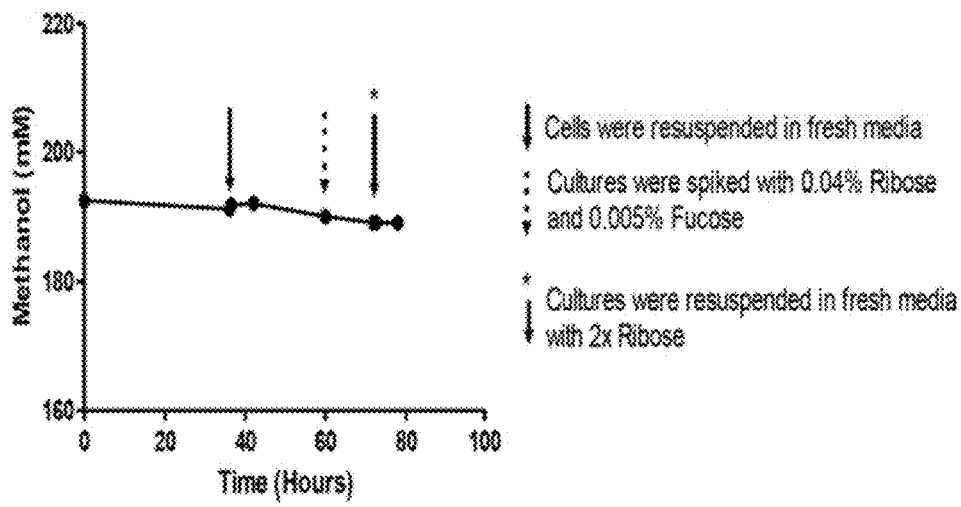

We next wanted to see if *E. coli* expressing MDH and genes of the RuMP pathway would be able to utilize methanol as a carbon and energy source. *E. coli* BL21(DE) containing either pETM6_Bs_MDH_L3RuMP or pETM6_Empty was grown overnight in LB broth plus ampicillin. These cultures were diluted 1/50 into fresh LB and incubated until the culture reached an OD$_{600}$ of approximately 0.4. At such time, the cultures were induced with 0.5 mM IPTG and incubated for a further 3 h. Cultures were grown in 10 ml of media in 50 ml conical tubes throughout the experiment. After IPTG induction, the cultures were pelleted and washed twice with M9 minimal media before being re-suspended at an OD$_{600}$ of 0.2 in M9 media containing ampicillin, IPTG, and 0.75% methanol. However, under these conditions no growth was observed by the strain carrying the genes for methanol utilization. We hypothesized that this was due to the strain's inability to regenerate ribulose-5-phosphate from fructose-6-phosphate (FIG. 1). Even though *E. coli* should possess the genes to natively undergo with pathway (via the pentose phosphate pathway; PPP), it is likely the native genes are not expressed under these conditions at sufficient levels. Therefore, we repeated the aforementioned experiments. This time we supplemented the M9 media with 0.04% ribose and 0.005% fucose (which has been shown previously to enhance ribose catabolism) (Autieri, Lins et al. 2007) in addition to 0.75% methanol. This time we were able to observe an increase in cell density or cell concentration (OD$_{600}$) in the strain carrying the methanol utilization genes compared with no increase in the control strains containing the empty vector (FIG. 36). After 24 h, the cultures were pelleted and re-suspended in fresh media and allowed to continue to grow. After a further 6 h, the OD$_{600}$ nearly doubled for the strain possessing the methanol utilization genes and HPLC analysis revealed that the strain had consumed approximately 5 mM of methanol (FIG. 37A). The OD$_{600}$ remained constant for the control and no methanol consumption was observed (FIG. 37B). After an additional 18 h, the OD$_{600}$ remained constant for both strains and no additional methanol was consumed during this time period. We hypothesized that this to be due to the fact that all of the ribose had been consumed for the strain carrying the methanol utilization genes during the first 6 h of growth. To test this, we added an additional 0.04% ribose and 0.005% fucose to the media to see if a spike with ribose would lead to additional methanol consumption. Indeed, for the strain carrying the methanol genes, the OD$_{600}$ increased from approximately 0.5 to 0.8 12 h after the culture was spiked with ribose (FIG. 36). Similarly, the methanol concentration decreased again, by about 5 mM for these cells as well (FIG. 37A). At this point, the cultures were again pelleted and re-suspended in fresh media with methanol, this time also containing 0.008% ribose and 0.005% fucose, to see if increasing the ribose concentration would affect methanol consumption. Six h after being re-suspended in the 2× ribose, the OD$_{600}$ of the strain containing the methanol utilization genes increased from approximately 0.5 to 1 (FIG. 36) and the amount of methanol consumed was observed to be 10 mM (FIG. 37A), indicating that doubling the ribose concentration lead to double the amount of methanol consumed by the cells. These data demonstrated that our engineered *E. coli* strain expressing MDH and two enzymes of the RuMP pathway (FIG. 1) can grow in minimal media containing methanol. Observed OD$_{600}$ increases are concordant with methanol depletion from the media.

Example 25. Cloning the Complete RuMP Pathway in *E. Coli*

Figure 38:
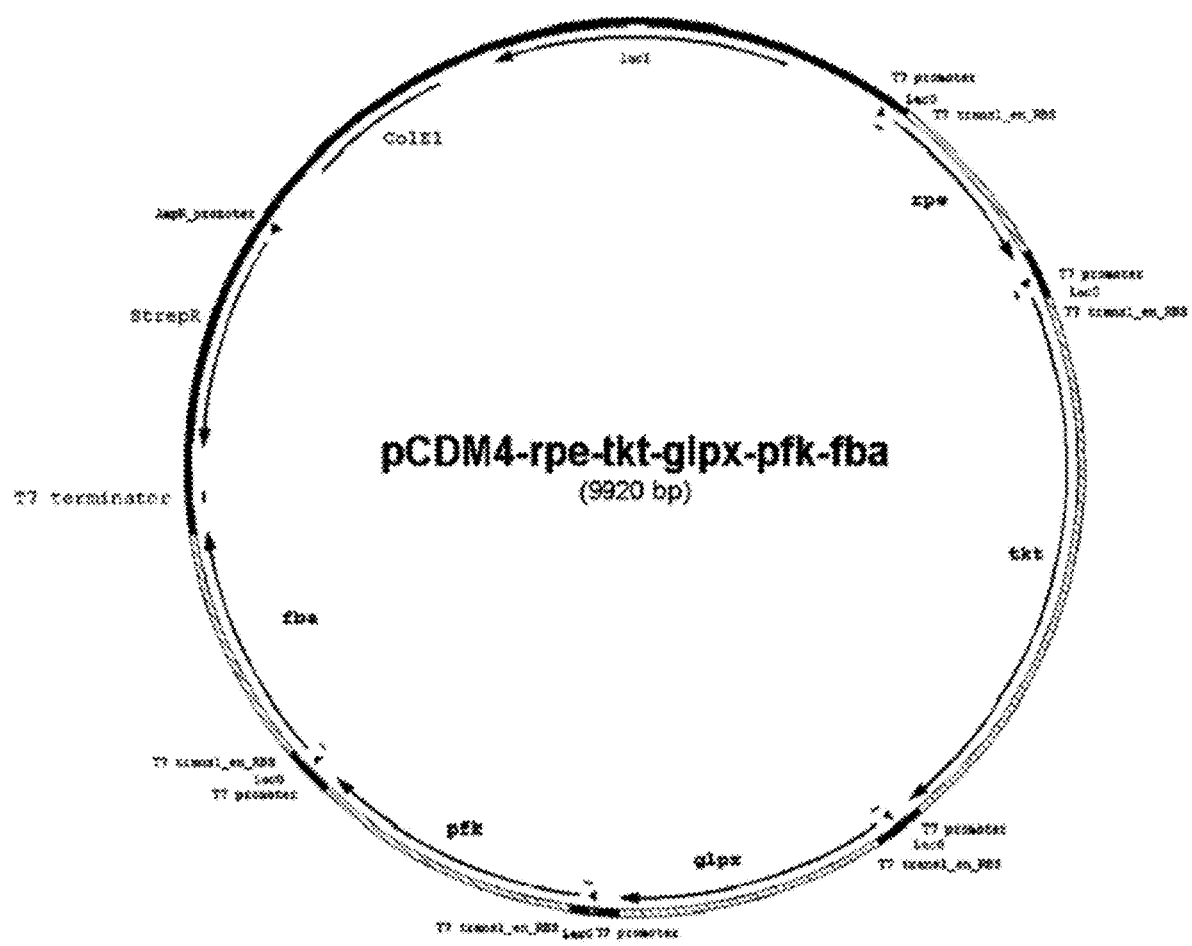
FIG. 38 shows RuMP pathway accessory genes cloned into the pCDM4 vector backbone in the pseudo-operon configuration.

Given the previous data, it appears that in order for *E. coli* to be able to utilize methanol without stimulation with ribose and fucose, it must be able to regenerate ribulose-5-phosphate in order to utilize the RuMP pathway. To achieve this goal, we were inspired by the methylotrophic organism *Bacillus methanolicus*, which utilizes the RuMP pathway for growth on MeOH. In this organism, growth on MeOH is plasmid dependent, as these organisms harbor a plasmid that carries an mdh gene as well as five homologues of the pentose phosphate pathway genes (pfk, phosphofructokinase; fba, fructose bisphosphate aldolase; tkt, transketolase; glpX, fructose/sedoheptulose biphosphatase; rpe, ribulose phosphate epimerase). When the strain is cured of the plasmid, it loses the ability to grow on methanol. This has been shown to be due to the loss of the five PPP homologues vs loss of the MDH. Thus, we hypothesize that expression of the five genes from *B. methanolicus* in *E. coli* along with expression of MDH, HPS, and PHI will allow for the cells to regenerate ribulose-5-phosphate and thus grow utilizing methanol as the sole carbon and energy source. To that end, we have had the five genes from synthesized and optimized for expression in *E. coli*. We used the vector pCDM4, which is a medium copy vector in the Biobrick family compatible with the pETM6 vector to clone all five genes using the pseudo-operon conformation (FIG. 38). We carried out growth analysis of a BL21(DE) strain containing both vectors in MOPS minimal media containing only methanol as the carbon and energy source.

Example 26. Metabolic Engineering to Make *E. coli* Fix $CO_2$ when Growing on MeOH To achieve this, we explore two schemes and possibly a $3^{rd}$ one as a backup (these are shown on FIG. 2): Scheme 1 uses the reduction of $CO_2$ to formate and then to formaldehyde. Scheme 2 is a modified reverse TCA (tri-carboxylic acid) pathway and Scheme 3 is based on glycine synthase. First, for all schemes, we overexpress a carbonic anhydrase (CA) in order to increase the availability of $CO_2$ to the cells and drive the overall reaction to HCHO formation. CA catalyzes the hydration of $CO_2$ to $HCO_3^-$ and plays an important role in increasing the effective $CO_2$ concentration for $CO_2$ fixation in cyanobacteria. CA from a cyanobacterium was shown to enhance $CO_2$ utilization in *E. coli*, and thus we propose to use the same gene in our strains. We note that the physiological role of this CA is to enhance $CO_2$ uptake, unlike the role of the native *E. coli* CA, which is part of an operon induced under cyanate stress and thus has likely an opposite role. Nevertheless, the native CA did not interfere with the beneficial effect of the recombinant CA. For Scheme 1, we co-express CA with formate DH (FDH) and HCHO DH (FdDH) as a first step toward enhancing the overall $CO_2$ fixation. A similar strategy coupling the use of CA with a 3-enzyme pathway improved the formation of MeOH from $CO_2$ by >4-fold.

$CO_2$ fixation starts with $CO_2$ conversion to formate through a reversed formaldehyde dehydrogenase activity.

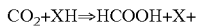

$$CO_2 + XH \Rightarrow HCOOH + X+$$

We heterologously express in *E. coli* a formate dehydrogenase from *Moorella thermoaceticum* that has been shown to act in the reverse direction as a $CO_2$ reductase. *Moorella thermoacetica* has been extensively studied as a model acetogene that uses the Wood-Ljungdahl pathway for CO and $CO_2$ fixation. In 1982, Yamamoto et al. purified and characterized the *Moorella* formate dehydrogenase as a heterotetramer ($\alpha 2\beta 2$) consisting of two each of two different subunits, namely $\alpha$ and $\beta$. The calculated molecular weights for these were 96,000 and 76,000, respectively. The enzyme was also found to contain selenium (in subunit $\alpha$), tungsten, iron and sulfur and to be inactivated even in trace amounts of oxygen. It catalyzed the conversion of $CO_2$ to formate with NADPH as cofactor. The two genes encoding for *Moorella* formate dehydrogenase subunits $\alpha$ and $\beta$, FDH-A and FDH-B were identified in 2008 upon release of the complete genome sequence of the organism with accession numbers AAB18330 and AAB18329, respectively.

The FDH-A gene was found to encode for a selenoprotein (MW=98,000) with the selenocysteine incorporation at position 358. In bacteria the SECIS element is an RNA element around 60 nucleotides long that appears soon after the selenocysteine codon (UGA) and forms a characteristic stem-loop structure. In the lack of the SECIS element the UGA sequence is recognized as a stop codon.

The SECIS element in Clostridia has a different primary and secondary structure compared to the *E. coli* one. Our effort focused in creating a hybrid cDNA sequence exchanging the Clostridia SECIS element with the *E. coli* SECIS element. Since the SECIS element is part of the ORF we tried to minimize the differences in the encoded protein by changing only the nucleotides that have been characterized as essential in recruiting the selenocysteine incorporation machinery in *E. coli*.

In order to design an *E. coli* SECIS element the SECIS design server (http://www.bioinf.uni-freiburg.de/Software/SECISDesign/) was used to design SECIS-elements within the coding sequence. The design was based on the natural SECIS-element FdhF of *E. coli* with all bonds of the stem-loop structure maintained.

The resulted sequence where the native *Moorella* SECIS element was substituted with the FdhF-based *E. coli* FDH is shown in FIG. 39A (SEQ ID NO: 8).

The SECIS element substitution resulted in a modified ORF with two amino-acid changes (underlined) in the encoded protein (Table 5).

The hybrid cDNA was further codon optimized to achieve higher expression levels in *E. coli*, except of the sequence coding for the *E. coli* SECIS element. Codon optimization was done for the *Moorella* FDH-B. Therefore, the final synthesized sequences by Genscript are shown in FIG. 39B (SEQ ID NO: 9) and FIG. 39C (SEQ ID NO: 10).

Both FDH-A and FDH-B optimized were subcloned into the pETDuet-1 vector that facilitates the co-expression of two target genes. We developed in vivo assays to assess the in vivo formaldehyde dehydrogenase and formate dehydrogenase activity in their reverse direction. The in vivo assay designed for this purpose is as follows:

(a) Start culture and incubate at 37° C. overnight in LB media. Inoculate fresh TB media and incubate until $OD_{600}=1-2$;

(b) Spin down the bacteria at 4000 g for 10 min at 4° C.;

(c) Resuspend bacterial pellet in minimal media (M9, MOPS) supplemented with glucose or glycerol;

(d) Induce with 0.2-1 mM IPTG and transfer the culture into serum bottles to be cultivated anaerobically;

(e) After 1-2 hours of incubation at 37° C. add 1 mM methyl-viologen to maintain the media reduced;

(f) Addition of sodium bicarbonate to provide the substrate for the in vivo activity; and (g) Let the culture grow at 37° C., sample at 1-18 h and test for protein expression, formate and formaldehyde concentration.

The formaldehyde dehydrogenase and formate dehydrogenase engineered strains were transformed with an extra plasmid carrying the *Nostoc* sp carbonic anhydrase that is expected to allow conversion of the $HCO_3^-$ to $CO_2$, the substrate for the formate dehydrogenase in the reverse direction.

Scheme 2. The reverse tricarboxylic acid (rTCA) cycle (FIG. 40) is one of 6 autotrophic $CO_2$ fixation cycles found in nature. rTCA is similar to the oxidative TCA cycle in *E. coli*; however, in the cycle reversal, molecules of $CO_2$ are fixed using reducing equivalents and ATP to produce acetyl-CoA. Many steps in the TCA cycle are reversible under standard conditions, including the aconitase, succinyl-CoA synthase, fumarase, and malate DH reactions. In most organisms using the rTCA cycle, there are 4 reactions for which alternative enzymes are needed to drive the reverse reaction towards $CO_2$ fixation: ATP citrate lyase (ACL), 2-oxoglutarate: ferredoxin oxidoreductase (OGOR), isocitrate DH (ICDH), and fumarate reductase (FR).

Scheme 3. The glycine synthase is a reversible mechanism of $CO_2$ fixation used by a number of clostridia when metabolizing reduced substrates. The glycine cleavage system begins by reducing $CO_2$ to formate using FDH. Formate is bound to a tetrahydrofolate (THF) coenzyme by formate-THF ligase in an ATP-dependent reaction. The resulting 10-formyltetrahydrofolate is reduced to 5,10-methylene-THF at which point the methylene-group is condensed with $CO_2$ and $NH_3$ to form glycine. In some bacterial species, the glycine can be converted to acetyl-Pi and then dephosphorylated. An alternate route uses an additional moiety of methylene-THF to produce serine, which can then be deaminated to form pyruvate. A large number of these reactions are native to E. coli. The 4 remaining enzymes that will be needed are aminomethyltransferase (AMT), dehydrolipoyl dehydrogenase (LPDH), glycine dehydrogenase (GDH), plus a $CO_2$-reducing FDH.

Example 27. Metabolic Engineering to Enable E. coli to Grow Effectively on MeOH

Methanol will be used as a carbon source by conversion to HCHO by a MeOH dehydrogenase (MDH). HCHO will then be converted to hexulose-6-phosphate, using ribulose-5-phosphate, by a hexulose phosphate synthase (HPS). Hexulose phosphate isomerase (PHI) will convert the hexulose-6-phosphate to fructose-6-phosphate, which can then be used for pyruvate generation that can be fed into the n-BuOH producing pathway (FIG. 2). There is strong experimental evidence supporting functionality of these genes, individually, in E. coli.

Figure 41A:
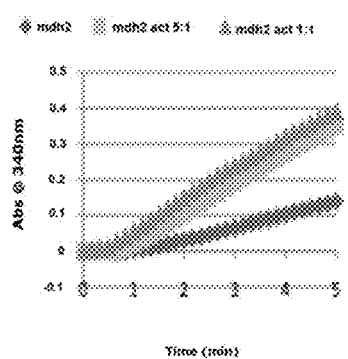
FIGS. 41A-C show measurement of methanol dehydrogenase (MDH) activity in vitro of expressed enzymes of *B. stearothermophilus* and *B methanolicus* PB1 along with the effect of an activator protein from *B. methanolicus* on MDH activity. The assay was adapted from Krog et al. (*PLOS One*. 2013; 8(3):59188) with the reduction of NAD+ measured at 340 nm. All assays were performed using crude *E. coli* cell extracts from strains containing the respective genes cloned into pETM6. *B. stearothermophilus* MDH is not stimulated by *B. methanolicus* PB1 ACT in any ratio (A). *B. methanolicus* PB1 MDH2 is stimulated by *B. methanolicus* PB1 ACT (B). Michaelis-Menten characterization of methanol dehydrogenases (C), where EXP represents experimental data and MM represents corresponding Michaelis-Menten fit.
Figure 41B:
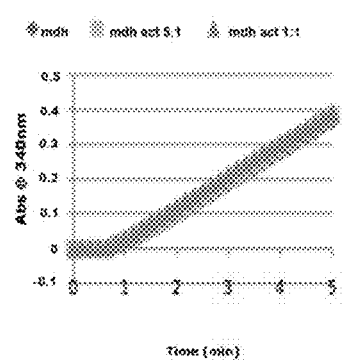
Figure 41C:
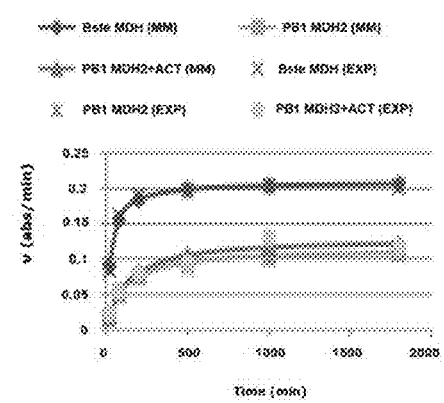

The methanol dehydrogenase (mdh) enzymes from Bacillus stearothermophilus (mdh1) and Bacillus methanolicus PB1 (mdh2) as well as an activator protein (act) from B. methanolicus PB1 were cloned into the pETM6 expression vector. MDH allows the cells to use methanol as a growth substrate, and the activator protein stimulates activity of the MDH of B. methanolicus PB1. The enzyme activity assay protocol of Krog et al. (PLOS One. 2013; 8(3):59188) was adapted to measure the $K_m$ and specific activity for each enzyme. Specific activities and $K_m$ values for MDH1 (from B. stearothermophilus), MDH2 (from B. methanolicus PB1), and MDH2 with ACT (the activator protein from B. methanolicus), were determined in crude lysates (FIG. 41). $K_m$ values for methanol were determined as 27 mM for MDH and 101 mM for MDH2, similar to those reported previously. Specific activities for MDH and MDH2 were determined as 0.014 and 0.008 µmol/min/mg, respectively, in crude cell extracts. The ACT of B. methanolicus PB1 also stimulated MDH2 activity in vitro, yielding a $K_m$ of 119 mM and a specific activity of 0.009 µmol/min/mg. Cloning of several other reported methanol dehydrogenases is in progress to identify the best candidates to move forward with.

Figure 42A:
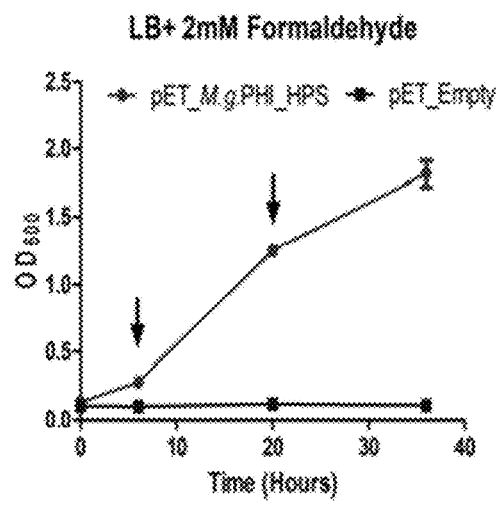
FIGS. 42A-B show growth of *E. coli* expressing HPS and PHI genes from *M. gastri*. The ability of *E. coli* to grow in A) LB or B) mixed M9:LB (3:1) spiked with formaldehyde was assessed. Log phase cultures of *E. coli* harboring pET_M.g.PHI_HPS (circles) or pET21_Empty (squares) were induced with 0.5 mM IPTG for 3 h before being diluted into test media containing 2 mM formaldehyde (LB) or 1.5 mM formaldehyde (M9:LB). Aliquots were taken from the cultures at the indicated time points to determine the optical density ($OD_{600}$). Arrows indicate times in which the cultures were spiked with (A) 2 mM or (B) 1.5 mM formaldehyde.
Figure 42B:
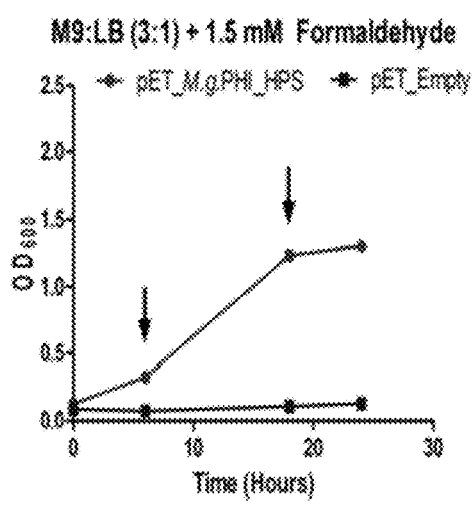
Figure 43:
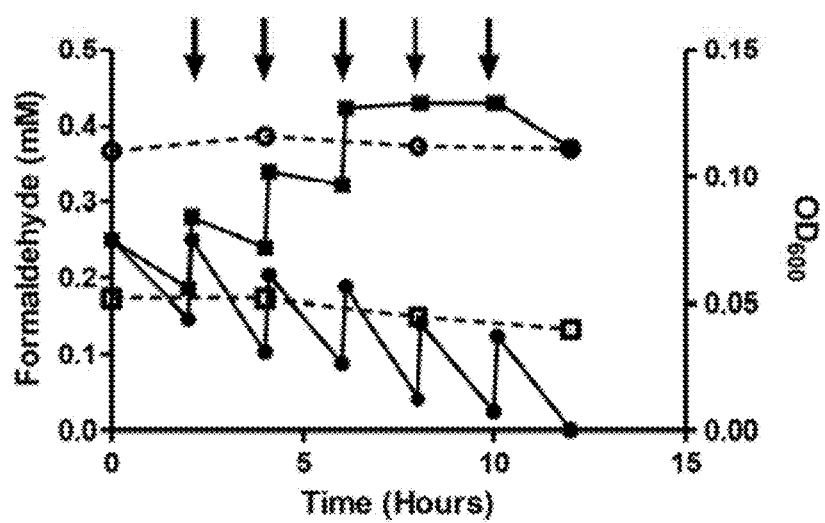
FIG. 43 shows consumption of formaldehyde by *E. coli* cells expressing the *M. gastri* phi and hps genes in M9 minimal Media+0.25 mM formaldehyde. Log phase cultures of *E. coli* harboring pET_M.g.PHI_HPS (circles) or pET21_Empty (squares) were induced with 0.5 mM IPTG for 3 h before being diluted into M9 minimal media containing 0.25 mM formaldehyde as the sole carbon source. Aliquots were taken from the cultures at the indicated time points to determine the optical density ($OD_{600}$). Culture formaldehyde concentrations for pET_M.g.PHI_HPS (open circles; dashed line) and pET_Empty (open squares; dashed line) were determined via the Hantzch reaction. Arrows indicate times in which the cultures were spiked with 0.25 mM formaldehyde.

Primers were designed to amplify the Mycobacterium gastri phi-hps operon, which encodes the genes necessary to fix formaldehyde to ribulose-5-phosphate yielding hexulose-6-phosphate, and then convert ribulose-5-phosphate to fructose-6-phosphate. Genes were amplified and initially cloned into the expression vector pET21a (Novagen). This vector utilizes the T7 promoter, and was transformed into the Rosetta strain of E. coli. E. coli Rosetta expressing the M. gastri PHI-HPS operon was compared with an empty vector control for growth in LB with 2 mM formaldehyde (FIG. 42A-B). E. coli cells expressing the phi and hps genes from M. gastri were able to grow in LB plus formaldehyde (FIG. 42A) or a mixture of M9 and LB plus formaldehyde (FIG. 42B), whereas cells containing only an empty vector control were unable to grow under either of the conditions tested. When the same strains were tested in M9 minimal media containing only formaldehyde (0.25 mM) as the sole carbon source, no increase in $OD_{600}$ was observed (FIG. 43). However, the strain expressing the phi and hps genes was able to consume the formaldehyde at a faster rate than the empty vector control strain, indicating that the genes were functional but there was most likely not enough of the carbon source to support meaningful growth of the culture.

We were able to incorporate the B. stearothermophilus_mdh gene into the vector containing the M. gastri phi-hps operon (pET_M.g._PHI_HPS) and successfully transform E. coli with the resulting three gene plasmid. However, we failed to detect MDH activity in culture lysates. As such, we have abandoned the use of the pET21 vector (Novagen) given its limitations in incorporating multiple gene pathways and have begun working with the pETM6 vector. This vector is designed for the sequential addition of genes in a multi-gene pathway and allows for each gene to be under the control of its own promoter. Therefore, we have decided to use this expression system henceforth for cloning and expressing the mdh and RuMP genes as this will allow us to combine different genes from different organisms and determine which combination gives the best growth rates.

Additionally, the genome of the methylophic bacteria strain L3 has been sequenced to provide for additional candidate genes for methanol utilization. We found that the L3 strain contains two putative hps genes and one putative phi gene, all of which are currently being cloned into the pETM6 vector in order to compare their abilities for formaldehyde consumption with the genes from M. gastri.

Example 28. Metabolic Engineering to Enable E. coli to Fix $CO_2$ when Growing on MeOH To achieve this, we will explore two schemes and possibly a third one as a backup. First, for all schemes, we will overexpress a carbonic anhydrase (CA) in order to increase the availability of $CO_2$ to the cells and drive the overall reaction to HCHO formation. CA catalyzes the hydration of $CO_2$ to $HCO_3^-$ and plays an important role in increasing the effective $CO_2$ concentration for $CO_2$ fixation in cyanobacteria. CA from a cyanobacterium (Anabaena sp. 7120) was shown to enhance $CO_2$ utilization in E. coli, and thus we propose to use the same gene in our strains. We note that the physiological role of this CA is to enhance $CO_2$ uptake, unlike the role of the native E. coli CA, which is part of an operon induced under cyanate stress and thus has likely an opposite role. Nevertheless, the native CA did not interfere with the beneficial effect of the recombinant CA. Based on this discussion, we will co-express CA with formate DH (FDH) and HCHO DH (FdDH) as a first step toward enhancing the overall $CO_2$ fixation. A similar strategy coupling the use of CA with a 3-enzyme pathway improved the formation of MeOH from $CO_2$ by >4-fold. $CO_2$ fixation is best and most easily assessed by following the fate of $^{13}CO_2$ or $^{13}C$-bicarbonate by GC-MS.

SCHEME 1: $CO_2$ reduction to formate and HCHO will use a FDH and a FdDH (or a HCHO dismutase (FdDM)), respectively (FIG. 2 & Table 6). One may be concerned with the thermodynamic feasibility of using FDH and FdDH to enable $CO_2$ capture. Indeed, under most circumstances the preferred reaction direction oxidizes $CH_2O$ to $CO_2$. Yet, there are a number of conditions both in vivo and in vitro, in which the reduction of $CO_2$ to HCHO is possible, despite the computed positive $\Delta_r G'$ numbers [calculations used the eQuilibrator with 0.1 M ionic strength, pH=7, and reactants/products at 1 mM]:

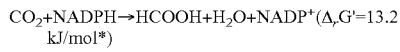
$CO_2$+NADPH→HCOOH+$H_2O$+NADP$^+$($\Delta_r G'$=13.2 kJ/mol*)

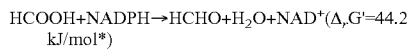
HCOOH+NADPH→HCHO+$H_2O$+NAD$^+$($\Delta_r G'$=44.2 kJ/mol*)

Indeed, in vivo, reduction of $CO_2$ to formate (some at very high rates) using an NADPH-dependent FDH is widespread in the $CO_2$-fixing acetogens, which use the Wood-Ljungdahl pathway (WLP). Acetogen FDHs favor the reduction of $CO_2$ to formate due to the tight binding of NADPH to the enzyme, and this was recently shown to be the case in vitro as well for the enzyme we plan to use. Substrate binding and other micro-environmental conditions dramatically change the local concentrations in the gel-like cellular milieu (as compared to the standard solution environments used for calculations) to make this reaction possible. Biological reduction of formate to HCHO has also been demonstrated, both in vivo and in vitro. Enzyme studies have shown the use of an FdDH to produce HCHO from formate using NADH or reduced viologen. In vitro, this reaction was also clearly demonstrated using a yeast FdDH, which requires glutathione (GSH; a tripeptide produced natively at good rates in E. coli). An alternate route to produce HCHO from formate is the reverse HCHO dismutase reaction [HCOOH+MeOH↔2(HCHO)+$H_2O$] using MeOH as an electron source, rather than NAD(P)H. This reaction is observed in methylotrophs that lack a dedicated MDH, which necessitates the presence of both HCOOH and MeOH for growth.

Figure 44A:
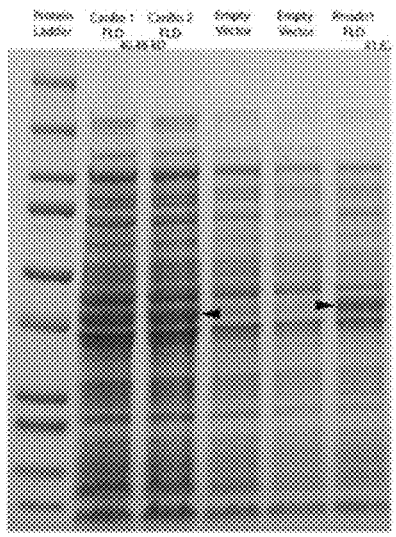
FIGS. 44A-D show heterologous-expression and enzymatic activity assays for formaldehyde dehydrogenases from *C. boindini* (CanBo), *R. sphaeroides* (Rhodo) and *M. flagellatus* (M8). (A) SDS-PAGE protein gel showing expression levels for GenCanBo (CanBo 1), DNA2.0 (CanBo 2) and Rhodo 1. (B) *C. boindini* formaldehyde dehydrogenase activity monitoring NADH synthesis at OD340. Assay buffer and PET21A empty vector lysate were tested as negative controls. (C) *R. sphaeroides* and *M. flagellatus* formaldehyde dehydrogenase activity monitoring NADH synthesis at OD340. PET21A empty vector lysate was tested as negative control. (D) *C. boindini* (CanBo) and *R. sphaeroides* (Rhodo) formaldehyde dehydrogenase activity in reverse direction (NADH consumption for reduction of formate to formaldehyde).
Figure 44B:
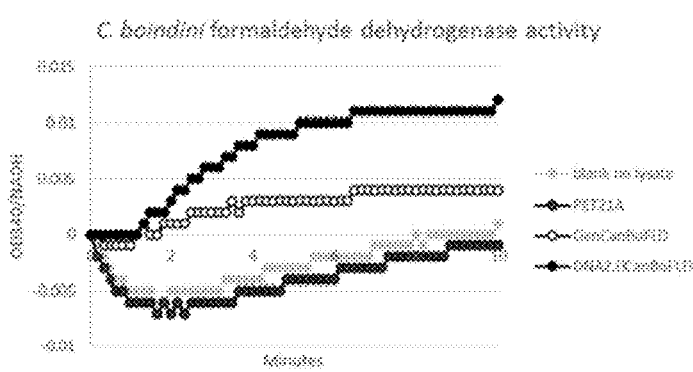
Figure 44C:
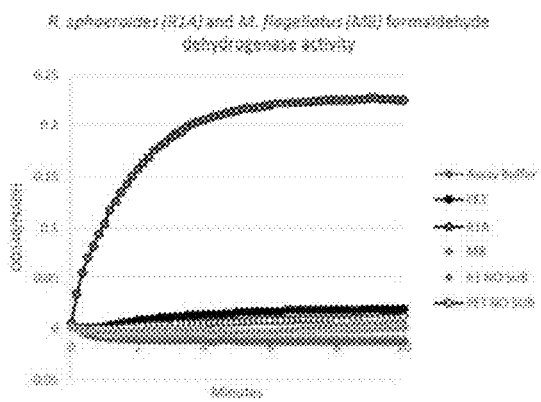
Figure 44D:
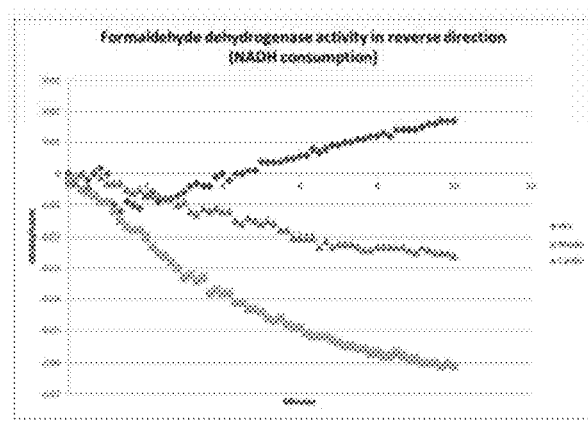

The open reading frames of two FDH genes, three FdDH genes and one CA gene were codon optimized for E. coli expression and cloned into pET (Novagen) expression vectors (Table 7). The fdh genes are from Clostridium carboxidivorans and Eubacterium acidaminophilum, and the ca is from a Nostoc species. The fld genes originate from Rhodobacter sphaeroides, Methylobacillus flagellatus, and Candida boindini. Crude protein lysates of over-expressing E. coli strains expressing C. boindini FLD and R. sphaeroides FLD (FIG. 44A) were tested for activity in vitro by monitoring NADH production in the reaction: formaldehyde+$H_2O$+NAD$^+$↔formate+NADH. The C. boindini and the R. sphaeroides were found active in both directions (FIG. 44B-D). M. flagellatus enzyme was not expressed at visible levels and when tested the clear lysate was found inactive (FIG. 44D).

Example 29. Engineering E. coli to Grow Well on MeOH and Fix $CO_2$

We desire to engineer E. coli to grow well on MeOH and fix $CO_2$ driven by the excess reduction energy derived from MeOH use under anaerobic conditions. To achieve this, we must assemble the best possible genes/enzymes for the 3 modules (MeOH use; $CO_2$ fixation; n-BuOH formation; FIG. 2). Each of these goals must be carried out efficiently and assessed for effectiveness of outcomes in terms of rates of MeOH and $CO_2$ utilization and carbon fluxes to pyruvate, acetyl-CoA and n-BuOH (FIG. 2).

1. Strain Engineering

The proposed approach is to simultaneously use MeOH and $CO_2$ to produce n-butanol (n-BuOH) (FIG. 2). This will be achieved by leveraging genes from methylotrophs for MeOH utilization (Module 1); various genes from acetogens and other organisms for $CO_2$ fixation (Module 2), and these two modules will be combined with the n-BuOH Module 3 that has already been constructed and demonstrated for efficiency.

2.a. Genes for Metabolic Engineering to Enable E. coli to Grow Effectively on MeOH.

Methanol will be used as a carbon source by conversion to HCHO by a MeOH dehydrogenase (MDH). HCHO will then be converted to hexulose-6-phosphate, using ribulose-5-phosphate, by a hexulose phosphate synthase (HPS). Hexulose phosphate isomerase (PHI) will convert the hexulose-6-phosphate to fructose-6-phosphate, which is can then be used for pyruvate generation that can be fed into the n-BuOH producing pathway (FIG. 2). There is strong experimental evidence supporting functionality of these genes, individually, in E. coli.

The mdh gene of Bacillus methanolicus C1 was cloned in E. coli and used for protein purification. While we will first use the B. methanolicus C1 mdh, in case this gene is not effective, we have compiled a list of alternative genes (Table 8) that we can use including the MDH from Methylobacterium extorquens AM1. The recent genome sequences of B. methanolicus strains MGA3 and PB1 revealed that there are three different mdh genes in each of the two strains. The 3 B. methanolicus MGA3 mdh genes are quite different, with mdh1 sharing 22% and 60% homology with mdh2 and mdh3. The mdh2 and mdh3 genes share only 22% homology. However, on the protein level, Mdh2 and Mdh3 are 96% identical, and share 61% and 62% sequence homology with Mdh. We will initially clone mdh and investigate whether the resulting protein is functional in E. coli. If the activity is low, we will done the additional proteins on a single plasmid. Another option is the alcohol DH (ADH) from B. stearothermophilus, which was cloned into E. coli and whereby oxidation of methanol was demonstrated. NAD+ was used as a cofactor for methanol oxidation. NAD/NADH is the most desirable coenzyme for this reaction as NADH produced from this reaction will be used to drive $CO_2$ fixation and BuOH production.

The next two enzymes, HPS and HPI, have also been successfully cloned into E. coli. Cell extracts of E. coli containing an expression plasmid with the Bacillus subtilis hps and phi genes were used to show good activity for these enzymes. Furthermore, $^{13}C$ NMR demonstrated that HCHO was incorporated into hexulose-6-phosphate and fructose-6-phosphate. In addition, the hps and phi cluster from B. brevis S1 was cloned into E. coli to demonstrate good HPS and PHI activities. More recently, a gene coding for an HPS-PHI fusion from Mycobacterium gastri MB19 was expressed in E. coli and cells were able to metabolize HCHO added to the culture and continue growing. We have also included the Methylococcus capsulatus MCA2738 gene that is annotated to have HPS and PHI activities, as another option to investigate. Combined, these data strongly suggest that expression of MDH, HPS and PHI expression in E. coli is feasible and can facilitate the formation of F6P from MeOH through HCHO via the RuMP pathway. We will first express these genes alone, test in vitro activities, choose the genes that lead to the two highest activities and then express these genes combinatorially aiming to identify at least 2 combinations of the 3 genes that give the best growth on MeOH prior to pursuing Tasks 3 and 4. Effectiveness is assessed by the rate of growth on MeOH and final densities (by $OD_{600}$ measurements), as well as rates of MeOH utilization (by GC and/or HPLC). We will also examine metabolites (acetate, ethanol, higher carboxylic acids; by HPLC) that will likely be produced anaerobically until we engineer this module into the n-BuOH producing strain. Strategies for expressing these genes are discussed below. The Gibson assembly method enables quick plasmid construction for screening to identify the best genes and the best combinations.

2.b. Metabolic Engineering to Enable E. coli to Fix $CO_2$ when Growing on MeOH

To achieve this, we will explore two schemes and possibly a third one as a backup. First, for all schemes, we will overexpress a carbonic anhydrase (CA) in order to increase the availability of $CO_2$ to the cells and drive the overall reaction to HCHO formation. CA catalyzes the hydration of $CO_2$ to $HCO_3^-$ and plays an important role in increasing the effective $CO_2$ concentration for $CO_2$ fixation in cyanobacteria. CA from a cyanobacterium (*Anabaena* sp. 7120) was shown to enhance $CO_2$ utilization in *E. coli*, and thus we propose to use the same gene in our strains. We note that the physiological role of this CA is to enhance $CO_2$ uptake, unlike the role of the native *E. coli* CA, which is part of an operon induced under cyanate stress and thus has likely an opposite role. Nevertheless, the native CA did not interfere with the beneficial effect of the recombinant CA. Based on this discussion, we will co-express CA with formate DH (FDH) and HCHO DH (FdDH) as a first step toward enhancing the overall $CO_2$ fixation. A similar strategy coupling the use of CA with a 3-enzyme pathway improved the formation of MeOH from $CO_2$ by >4-fold. $CO_2$ fixation is best and most easily assessed by following the fate of $^{13}CO_2$ or $^{13}C$-bicarbonate by GC-MS.

SCHEME 1: $CO_2$ reduction to formate and HCHO will use a FDH and a FdDH (or a HCHO dismutase (FdDM)), respectively (FIG. 2 & Table 9). One may be concerned with the thermodynamic feasibility of using FDH and FdDH to enable $CO_2$ capture. Indeed, under most circumstances the preferred reaction direction oxidizes $CH_2O$ to $CO_2$. Yet, there are a number of conditions both in vivo and in vitro, in which the reduction of $CO_2$ to HCHO is possible, despite the computed positive $\Delta_rG'$ numbers [calculations used the eQuilibrator with 0.1 M ionic strength, pH=7, and reactants/products at 1 mM]:

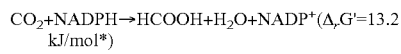

$CO_2$+NADPH→HCOOH+$H_2O$+NADP$^+$($\Delta_rG'$=13.2 kJ/mol*)

HCOOH+NADPH→HCHO+$H_2O$+NAD$^+$($\Delta_rG'$=44.2 kJ/mol*)

Indeed, in vivo, reduction of $CO_2$ to formate (some at very high rates) using an NADPH-dependent FDH is widespread in the $CO_2$-fixing acetogens, which use the Wood-Ljungdahl pathway (WLP). Acetogen FDHs favor the reduction of $CO_2$ to formate due to the tight binding of NADPH to the enzyme, and this was recently shown to be the case in vitro as well for the enzyme we plan to use. Substrate binding and other micro-environmental conditions dramatically change the local concentrations in the gel-like cellular milieu (as compared to the standard solution environments used for calculations) to make this reaction possible. Biological reduction of formate to HCHO has also been demonstrated, both in vivo and in vitro. Enzyme studies have shown the use of an FdDH to produce HCHO from formate using NADH or reduced viologen. In vitro, this reaction was also clearly demonstrated using a yeast FdDH, which requires glutathione (GSH; a tripeptide produced natively at good rates in *E. coli*). An alternate route to produce HCHO from formate is the reverse HCHO dismutase reaction [HCOOH+MeOH↔2 (HCHO)+$H_2O$] using MeOH as an electron source, rather than NAD(P)H. This reaction is observed in methylotrophs that lack a dedicated MDH, which necessitates the presence of both HCOOH and MeOH for growth.

SCHEME 2: The reverse tricarboxylic acid (rTCA) cycle (FIG. 40) is one of 6 autotrophic $CO_2$ fixation cycles found in nature. rTCA is similar to the oxidative TCA cycle in *E. coli*; however, in the cycle reversal, molecules of $CO_2$ are fixed using reducing equivalents and ATP to produce acetyl-CoA. Many steps in the TCA cycle are reversible under standard conditions, including the aconitase, succinyl-CoA synthase, fumarase, and malate DH reactions. In most organisms using the rTCA cycle, there are 4 reactions for which alternative enzymes are needed to drive the reverse reaction towards $CO_2$ fixation: ATP citrate lyase (ACL), 2-oxoglutarate: ferredoxin oxidoreductase (OGOR), isodtrate DH (ICDH), and fumarate reductase (FR) (Table 10)

ACL uses ATP hydrolysis to drive the unfavorable thermodynamics towards the formation of oxaloacetate and acetyl-CoA. The aclBA genes from *Chlorobium tepidum* and *C. limicola* have been functionally expressed in *E. coli*, and either set of genes would be suitable for the goal here. OGOR catalyzes the carboxylation of succinyl-CoA to form α-ketoglutarate. Two distinct enzymes have been identified in autotrophs with the rTCA cycle: For and Kor. These enzymes have been best studied in the $H_2$-oxidizing bacterium *Hydrogenobacter thermophilus*, which grows quickly on $H_2$, $CO_2$, and $O_2$ with a doubling time of ~1 h. For consists of 5 subunits that are encoded in the forDABGE gene cluster and is necessary for aerobic growth. Kor has 2 subunits coded on the korAB gene cluster and is essential for anaerobic growth; this will be used here. Both enzymes use reduced ferredoxin, which has a greater reduction potential than NADH, to drive the endergonic carboxylation of succinyl-CoA. Organisms that use the rTCA cycle have specialized ICDH enzymes that preferentially operate in the carboxylating direction. ICDH from *C. limicola*, for instance, has the same affinity for carboxylation as for decarboxylation at physiological pH, as compared to ICDH from other organisms, in which decarboxylation is favored 4:1. ICDH activity in *H. termophilus* operates through an entirely different mechanism than that of *C. limicola* or the oxidative TCA cycle. *H. thermophilus* has 2 enzymes—2-oxoglutarate carboxylase (OGC) and oxalosuccinate reductase (OSR)—that carboxylate α-ketoglutarate in two steps. First, OGC uses ATP to carboxylate α-ketoglutarate to oxalosuccinate, and OSR then converts oxalosuccinate to isocitrate. FR catalyzes the reduction of fumarate to succinate. Since *E. coli* already makes use of fumarate reductase for anaerobic respiration, overexpression of heterologous genes may not be necessary.

SCHEME 3: The glycine synthase is a reversible mechanism of $CO_2$ fixation used by a number of clostridia when metabolizing reduced substrates. The glycine cleavage system begins by reducing $CO_2$ to formate using FDH. Formate is bound to a tetrahydrofolate (THF) coenzyme by formate-THF ligase in an ATP-dependent reaction. The resulting 10-formyltetrahydrofolate is reduced to 5,10-methylene-THF at which point the methylene-group is condensed with $CO_2$ and $NH_3$ to form glycine. In some bacterial species, the glycine can be converted to acetyl-P$^i$ and then dephosphorylated[53]. An alternate route uses an additional moiety of methylene-THF to produce serine, which can then be deaminated to form pyruvate. A large number of these reactions are native to *E. coli*. The 4 remaining enzymes that will be needed are aminomethyltransferase (AMT), dehydrolipoyl dehydrogenase (LPDH), glycine dehydrogenase (GDH), plus a $CO_2$-reducing FDH.

2.c. Expression Details. Protein and Enzymatic Assays

Expression vectors and promoters. The genes listed in Tables 7-9 are to be cloned in two compatible plasmids. The genes associated with MeOH consumption, mdh, hps and phi, totaling approximately 2700 bp, will be cloned on a plasmid with the p15A origin of replication. The genes enabling $CO_2$ utilization (ecaA, fdh, and fddh, or alternates as above) will be cloned on a high copy pBR322 origin of replication plasmid. All genes will be first cloned under the strong tac promoter, with rho independent terminators between each gene. The genes will be codon optimized for *E. coli*, and cloning will be done via Gibson assembly. After cloning, genes will be evaluated for good expression by qRT-PCR.

Enzyme assays and Western blots to ensure that functional proteins are produced. We will first employ functional enzymes assays as detailed below. Once we settle on a smaller set of genes, we will generate antibodies against the corresponding proteins. We will use a commercial vendor that has successfully generated many antibodies for a large variety of proteins for other projects. The antibodies will be used to carry out Western blots in order to quickly assess the impact of optimized expression and culture conditions on the protein levels of these recombinant proteins. Enzyme assays will be carried out for the reactions to enable MeOH utilization and $CO_2$ fixation. The main focus of this effort is on the MeOH utilization pathway and the $CO_2$ fixation through formate and $CH_2O$. The presence of the native TCA cycle enzymes would complicate in vitro assays of the rTCA cycle SCHEME 2. For that and the backup SCHEME 3, we will rely on mRNA levels of expression by Q-RT-PCR. MDH, FdDH and FDH activity can be also monitored using alternate assays. PHI activity will be also assayed.

2.d. Integrate Optimized Modules 1, 2 and 3 (FIG. 2) to Achieve Effective MeOH Utilization, $CO_2$ Fixation and n-BuOH Formation.

The assembled Modules 1 and 2 (FIG. 2) will be optimized to achieve high rates of MeOH and $CO_2$ utilization and n-BuOH formation. The goal is to integrate and further optimize these pathways by combing the best of these into a single strain that does not produce BuOH and later after some testing, into a BuOH producing strain. We will then employ chemical mutagenesis and strain evolution to achieve better growth on MeOH, $CO_2$ fixation and n-BuOH production. BuOH producing strain contains several gene deletions aiming to enhance the electron availability for BuOH production under anaerobic conditions. The strain then expresses a clostridial pathway for n-BuOH, with the genes expressed from co-existing plasmids. With the additional genes (FIG. 2) that will be needed here, we will need to integrate several of the genes from Modules 1 and 3 (FIG. 2) and possibly from the BuOH-formation pathway into the chromosome. What will be integrated will be based on mRNA expression levels that we will measure by qRT-PCR. We have employed chromosomal integrations of multiple genes into the *E. coli* genome using the lambda-red system, so we will use these methods for chromosomal integration of genes. Strains that combine all 3 modules (FIG. 2) will be tested for growth on MeOH, $CO_2$ fixation and BuOH production. A few of the best performing strains will be evolved through chemical mutagenesis and fast transfer for faster growth on MeOH anaerobically under a $CO_2$ and also $H_2$ atmosphere (3 atm) is serum vials used to grow acetogens on gas mixtures of $CO_2/CO/H_2$. The $CO_2$ and Hz pressure is to stimulate $CO_2$ uptake under a reducing environment and is meant to simulate the large-scale process where a large $CO_2$ pressure will be built during the anaerobic fermentation. A few of the best performing strains with gene integrations and accumulated mutations will be sequenced by the new PacBio technology. The goal will be to examine the mutations that improve the phenotype.

Example 30. Bioenergetic and Pathway Analysis

1. Conversion of Methanol to Acetyl-CoA and Butanol

Figure 40:
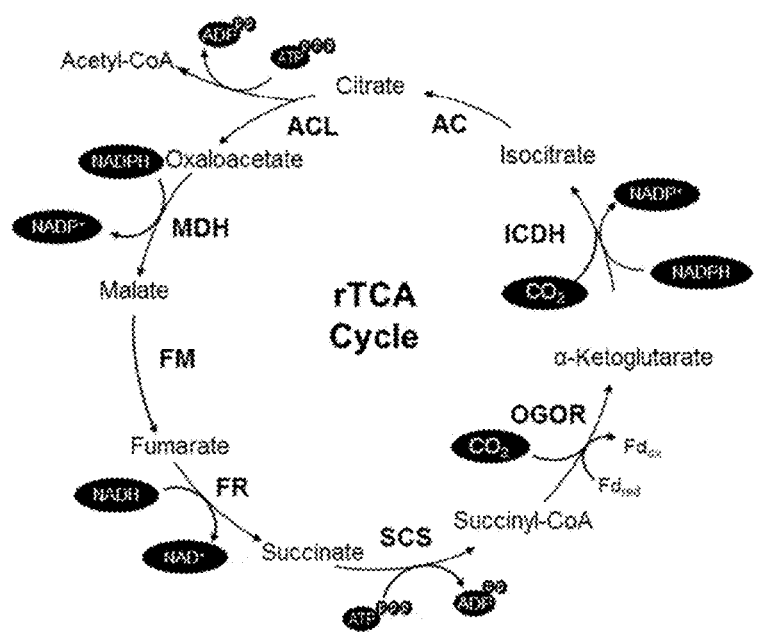
FIG. 40 illustrates the reverse tricarboxylic acid (rTCA) cycle.

We will engineer *E. coli* cells to utilize MeOH as a carbon and energy source in an engineered RuMP pathway. To meet ARPA-E yield and energy efficiency we will use $CO_2$ recycling by Schemes 1 or 2 (or 3 if necessary) (FIG. 2). In Scheme 1, $CO_2$ is reduced to formate and then HCHO (rxn 2 of FIG. 2) that can be assimilated through the RuMP pathway. Scheme 2 utilizes the rTCA cycle (FIG. 40). Backup Scheme 3 uses the glycine cleavage pathway via the glycine synthase. While Schemes 2 and 3 are not as ATP efficient (see rxn 3 of FIG. 2) as Scheme 1, ATP hydrolysis improves the overall thermodynamic outlook of $CO_2$ fixation. Maximum theoretical yields were calculated per ARPA-E instructions for the engineered RuMP pathway with $CO_2$ recycling through either Scheme 1, 2 or 3 (Table 11). In both cases (Scheme 1; Scheme 2 or 3), the calculated yields outperform the energy efficiency and carbon yield metrics of >64% and >67%, respectively, even if we assume that 80% (our target) of theoretically possible $CO_2$ is fixed (in fact ca. 67% of the theoretically possible $CO_2$ fixation would suffice).

2. The Rate of Product Formation

For producing n-BuOH, we will employ the recently reported system, which produces ca. 30 g/L n-BuOH, but at a rate <1 g/gCDW/h. To meet the latter rate, we will need to optimize all 3 modules (FIG. 2). We will first aim to achieve fluxes to acetyl-CoA that supports high fluxes of product formation for products synthesized through Acetyl-CoA. Then, we will assess the bottlenecks in Module 3 (BuOH synthesis) by relating flux data to mRNA levels of key genes to examine if gene expression of certain genes is limiting the flux. Based on flux data, mRNA data and enzyme assays, we will identify the steps that limit the overall rate, and will use an iterative optimization process to achieve the most efficient strain and process.

3. Technological Scenarios for Conversion of $CH_4$ to BuOH

The four possible outcomes $CH_4$ activation are shown in FIG. 1, with case III representing the status quo with two electrons lost, case IV representing all electrons conserved for $CH_4$ to MeOH conversion, and cases II and III representing intermediate levels of electron loss. The conservation of electrons in the $CH_4$ activation has a dramatic Impact on product yields as shown in Table 12. The status quo of $CH_4$ activation (Case III), results in the lowest calculated BuOH yield which will not likely find industrial applications. In contrast, if all electrons are conserved (Case IV), an abundance of reducing energy allows for net $CO_2$ fixation using Scheme 1 for $CO_2$ recycling and 100% carbon efficiency with respect to $CH_4$ under Schemes 2 or 3.

TABLE 1

NAD$^+$-dependent MDHs.

| Source | MDH |
|---|---|
| *Bacillus stearothermophilus* 2334 | Mdh |
| *Bacillus stearothermophilus* NUB3621 | Mdh |
| *Bacillus methanolicus* C1 | Mdh |
| *Bacillus methanolicus* PB1 | Mdh |
| | Mdh1 |
| | Mdh2 |
| *Bacillus methanolicus* MGA3 | Mdh |
| | Mdh2 |
| | Mdh3 |

TABLE 2

| Methanol Redox Reaction | Standard Conditions | | | Physiological Conditions | | | |
|---|---|---|---|---|---|---|---|
| | $\Delta\epsilon'$ (mV) | $\Delta_rG'$ (kJ/mol) | $K'_{eq}$ | T (° C.) | $\Delta\epsilon$ (mV) | $\Delta_rG$ (kJ/mol) | $K_{eq}$ |
| CH$_3$OH + NAD $\Leftrightarrow$ HCHO + NADH + H$^+$ | −177 | +34.2 | 1.0 × 10$^{-6}$ | 37 | +5.3 (+36.1)$^a$ | −1.0 (−7.0)$^a$ | 0.925 (8.5)$^a$ |
| | | | | 45 | +9.6 (+41.1)$^a$ | −1.8 (−7.9)$^a$ | 0.927 (8)$^a$ |
| | | | | 55 | +14.9 (+47.4)$^a$ | −2.9 (−9.2)$^a$ | 0.929 (7.5)$^a$ |

Reaction Gibbs energies ($\Delta_rG$), equilibrium constants ($K_{eq}$), and change in reduction potential ($\Delta\epsilon$) for MeOH redox reactions calculated through eQuilibrator software. Standard conditions were 25° C., 1 bar, pH 7.0, 0.1M ionic strength, and 1 mM species concentrations. Physiological conditions were the indicated temperatures, 1 bar, pH 7.6, 0.1M ionic strength, 1250 mM MeOH, 0.17 mM HCHO, 2.6 mM NAD, 0.083 mM NADH. Data were calculated from the following equations: $\Delta_rG = -n(23,064) \Delta\epsilon$, where n represents the number of electrons transferred, $K_{eq} = 10^{-\Delta_rG/2.3RT}$, and $$\Delta_rG = \Delta_rG + RT\ln\frac{[P]}{[R]},$$

where P and R indicate products and reactants, respectively.
$^a$Values in parentheses under physiological conditions were calculated with a 10-fold decrease in HCHO concentration, i.e., 0.017 mM. The discrepancy between some of the $\Delta_rG$ and $K_{eq}$ values for NAD-dependent oxidation is likely a result of the 95% confidence interval for $\Delta_rG$, which is ± 6.5 kJ/mol.

TABLE 3

Peptide encoded by the artificial SECIS element compared to the peptide encoded by the original sequence that follows the selenocysteine.

| | |
|---|---|
| Original sequence (starting at position 359) | HSSTVAGLATTFGS (SEQ ID NO: 4) |
| Optimized amino-acid sequence | HSSTVAGLHQTFGS (SEQ ID NO: 5) |

TABLE 4

NAD$^+$-dependent MDH candidates

| MDH | Codon Optimized | in vivo Activity |
|---|---|---|
| Bst 2334 Mdh | No | Yes |
| Bst NUB3621 Mdh | Yes | Yes |
| Bme C1 Mdh | Yes | No |
| Bme PB1 Mdh | Yes | No |
| Bme PB1 Mdh1 | Yes | No |
| Bme PB1 Mdh2 | Yes | No |
| Bme MGA3 Mdh | Yes | No |
| Bme MGA3 Mdh2 | Yes | Yes |
| Bme MGA3 Mdh3 | Yes | Yes |

TABLE 5

Peptide encoded by the artificial SECIS element compared to the peptide encoded by the original sequence that follows the selenocysteine.

| | |
|---|---|
| Original sequence (starting at pos. 359): | HSSTVAGLATTFGS (SEQ ID NO: 4) |
| Amino Acid Sequence | HSSTVAGLLATFGS (SEQ ID NO: 11) |

TABLE 6

CO$_2$ fixation genes via SCHEME 1

| Gene | Source Organism | Size (bp) | Kinetics |
|---|---|---|---|
| CA (ecaA) | Nostoc sp. PCC 7120 (Anabaena sp. PCC7120) | 795 | Activity: 21.8 U/mg protein |
| FDH (fdh) | Clostridium carboxidivorans P7$^T$ | 2142 | Km = 0.05 mM (for NADH) |
| FdDH (fddh1) | Candida boidinii Fld1 | 2490 | N/A |
| HCHO DM | Pseudomonas putida 9816 | 1197 | N/A |

TABLE 7

List of protein-expression constructs to be used in SCHEME 1 of the CO$_2$ fixation module.

| | Construct name | Vector (antibiotic resistance) | Insert | Codon optimization for E. coli | His-tag | Sequenced |
|---|---|---|---|---|---|---|
| 1 | PET21a:optRhodo_FLD | pET21a(+) (amp) | Rhodobacter sphaeroides FLD | YES (Genscript) | NO | YES |
| 2 | PET21a:optMethylo_FLD | pET21a(+) (amp) | Methylobacillus flagellatus FLD | YES (Genscript) | NO | YES |

TABLE 7-continued

List of protein-expression constructs to be used in SCHEME 1 of the CO₂ fixation module.

| Construct name | Vector (antibiotic resistance) | Insert | Codon optimization for E. coli | His-tag | Sequenced |
|---|---|---|---|---|---|
| 3 PET21a:DNA2CanBo_FLD | pET21a(+) (amp) | Candida boindini FLD | YES (DNA2.0) | NO | YES |
| 4 PET21a:GenCanBo_FLD | pET21a(+) (amp) | Candida boindini FLD | YES (Genscript) | NO | YES |
| 5 PDUET1:optRhodo_FLD | pETDuet-1 (amp) | Rhodobacter sphaeroides FLD | YES (Genscript) | YES N-terminal | In progress |
| 6 PDUET1:optMethylo_FLD | pETDuet-1 (amp) | Methylobacillus flagellatus FLD | YES (Genscript) | YES N-terminal | In progress |
| 7 PET21a:optCloCa_FDH | pET21a(+) (amp) | Clostridium carboxidivorans FDH² | YES (IDT) | YES C-terminal | YES |
| 8 PACYC:optCloCa_FDH | pACYCDuet-1 | Clostridium carboxidivorans FDH | YES (IDT) | NO | YES |
| 9 PACYC:optEuacid_FDH | pACYCDuet-1 | Eubacterium acidaminophilum FDH-II | YES (Genscript) | NO | In progress |
| 10 PET28A:optCloCa_FDH | pET28a(+) | Clostridium carboxidivorans FDH | YES (IDT) | YES N-terminal | YES |
| 11 PET28A:optEuacid_FDH | pET28a(+) | Eubacterium acidaminophilum FDH-II | YES (Genscript) | YES N-terminal | In progress |
| 12 PET21a:CA | pET21a(+) (amp) | Nostoc sp carbonic anhydrase | YES (Genscript) | NO | YES |
| 13 PET21a:CA | pET21a(+) (amp) | Nostoc sp carbonic anhydrase | YES (DNA2.0) | NO | YES |

TABLE 8

Genes to enable growth of E. coli on MeOH with enzyme characteristics when known

| Gene | Organisms source | Gene size (bp) | Kinetics (BRENDA): $K_m$ (mM) Spec. act. [µmol/min/mg] |
|---|---|---|---|
| mdh | Bacillus methanolicus C1 | 1149 | 0.02, 1.2 |
| | Bacillus stearothermophilus | 1471 | |
| | Bacillus methanolicus MGA3 mdh, mdh2, mdh3 | 1149, 1158, 1158 | |
| | Methylobacterium extorquens AM1 | 1845 | |
| | mxaF (MDH subunit alpha) | 291 | |
| | mxaI (MDH subunit beta) | | |
| hps | Bacillus subtilis | 633 | 0.007 |
| | Bacillus brevis S1 | 633 | (Bacillus sp.), 3.5 |
| | Methylococcus capsulatus | 1170 | N/A, 7.4 |
| | MCA2738 (HPS and PHI activity) | | |
| | Mycobacterium gastri MB19 | 624 | |
| phi | Bacillus subtilis | 558 | N/A, 11 |
| | Bacillus brevis S1 | 552 | |
| | Methylococcus capsulatus | 1170 | |
| | MCA2738 (HPS and PHI activity) | | |
| | Mycobacterium gastri MB19 | 600 | |

TABLE 9

CO₂ fixation genes via SCHEME 1

| Gene | Source Organism | Size (bp) | Kinetics |
|---|---|---|---|
| CA (ecaA) | Nostoc sp. PCC 7120 (Anabaena sp. PCC7120) | 795 | Activity: 21.8 U/mg protein |
| FDH (fdh) | Clostridium carboxidivorans P7$^T$ | 2142 | Km = 0.05 mM (for NADH) |
| FdDH (fddh1) | Candida boidinii Fld1 | 2490 | N/A |
| HCHO DM | Pseudomonas putida 9816 | 1197 | N/A |

TABLE 10

Enzymes and genes for the rTCA cycle

| Enzymes | Source Organism | Genes |
|---|---|---|
| ATP Citrate Lyase (ACL) | C. tepidum or C. limicola | aclA, aclB |
| OGOR (For and Kor) | H. thermophilus | korAB |
| ICDH | C. limicola or H. thermophilus | idh |
| Fumarate Reductase (FR) | E. coli or H. thermophilus | frdABCDE |

TABLE 11 n-BuOH from MeOH (mol/100 mol MeOH)

| CO₂ fixation | Scheme 1 | Scheme 2 or 3 |
|---|---|---|
| Methanol | −100.0 | −100.0 |
| CO₂ | 0.0 | 0.0 |
| NAD(P)H | 0.0 | 0.0 |
| ATP | 50.0 | 0.0 |
| Butanol | 25.0 | 25.0 |
| Energy Efficiency | 96% | 96% |
| Carbon Yield | 100% | 100% |

TABLE 12 n-BuOH from $CH_4$ (mol/100 mol $CH_4$).

| | \multicolumn{8}{c}{$CO_2$ fixation} |
|---|---|---|---|---|---|---|---|---|
| | Scheme 1 | | | | Scheme 2 or 3 | | | |
| | \multicolumn{8}{c}{$CH_4$ Act. Scheme*} |
| | I | II | III# | IV | I | II | III# | IV |
| Methane | −100.0 | −100.0 | −100.0 | −100.0 | −100.0 | −100.0 | −100.0 | −100.0 |
| $CO_2$ | 0.0 | 16.7 | 33.3 | −33.3 | 0.0 | 16.7 | 33.3 | 0.0 |
| NAD(P)H | 0.0 | 0.0 | 0.0 | 0.0 | 0.0 | 0.0 | 0.0 | 100.0 |
| ATP | 50.0 | 41.7 | 33.3 | 66.7 | 0.0 | 16.7 | 33.3 | 0.0 |
| Butanol | 25.0 | 20.8 | 16.7 | 33.3 | 25.0 | 20.8 | 16.7 | 25.0 |
| Energy Efficiency | 77% | 64% | 51% | 102% | 77% | 64% | 51% | 77% |
| Carbon Yield | 100% | 83% | 67% | 133% | 100% | 83% | 67% | 100% |

*See FIG. 1 and text for $CH_4$ activation schemes.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method for producing a metabolite, comprising growing a non-naturally occurring microbe in a medium comprising methanol, wherein the non-naturally occurring microbe expresses heterologous methanol dehydrogenase (MDH) and one or more heterologous ribulose monophosphate (RuMP) pathway enzymes, wherein the heterologous MDH is *Bacillus stearothermophilus* MDH, wherein the one or more heterologous RuMP pathway enzymes comprise *Bacillus methanolicus* 3-hexulose-6-phosphate synthase (HPS) and *Bacillus methanolicus* 3-hexulose-6-phosphate isomerase (PHI), wherein the non-naturally occurring microbe is derived from *Escherichia* or *Corynebacterium*, and wherein the methanol contributes to at least 40% of the carbon source for the non-naturally occurring microbe, whereby the metabolite is produced.

2. The method of claim 1, wherein the metabolite is selected from the group consisting of 4-carbon chemicals, diacids, 3-carbon chemicals, higher carboxylic acids, alcohols of higher carboxylic acids, and polyhydroxyalkanoates.

3. The method of claim 1, wherein the metabolite is n-butanol.

4. The method of claim 1, further comprising modifying the gene of heterologous MDH or any one of the one or more heterologous RuMP pathway enzymes, whereby the yield of the metabolite is improved.

5. The method of claim 1, further comprising fixing $CO_2$.

6. The method of claim 1, wherein the non-naturally occurring microbe is grown at a temperature higher than 37° C.

7. The method of claim 1, wherein the non-naturally occurring microbe is grown anaerobically.

8. The method of claim 1, whereby at least 40% of the carbon in the metabolite is derived from the methanol.

9. The method of claim 1, wherein the metabolite is an amino acid or tricarboxylic acid (TCA) intermediate having a carbon at the fourth position derived from the methanol, wherein the TCA intermediates are selected from the group consisting of succinate, succinyl-CoA, alpha-ketoglutarate, isocitrate, citrate, oxaloacetate, malate and fumarate.

10. The method of claim 1, further comprising producing a metabolite by the non-naturally occurring microbe, and incorporating carbon from methanol into the metabolite, wherein at least 40% of the carbon in the metabolite is derived from the methanol.

11. The method of claim 1, wherein the non-naturally occurring microbe is derived from *Escherichia*.

12. The method of claim 1, wherein the non-naturally occurring microbe contains a deletion of an frmRAB operon.

13. The method of claim 1, wherein the non-naturally occurring microbe expresses one or more heterologous pentose-phosphate pathway (PPP) enzymes.

14. The method of claim 13, wherein the one or more heterologous PPP enzymes consist of heterologous phosphofructokinase (PFK), heterologous fructose bisphosphate aldolase (FBA), heterologous transketolase (TKT), heterologous fructose/sedoheptulose biphosphatase (GLPX), heterologous transaldolase (TAL), heterologous ribose-5-phospate isomerase (RPI) and heterologous ribulose phosphate epimerase (RPE).

15. The method of claim 1, wherein the non-naturally occurring microbe expresses one or more heterologous cyclic formaldehyde dissimilation enzymes.

16. The method of claim 15, wherein the one or more heterologous cyclic formaldehyde dissimilation enzymes consist of heterologous glucose-6-phosphate isomerase (PGI), glucose-6-phosphate-1-dehydrogenase (ZWF), 6-phosphogluconolactonase (PGL), and 6-phosphogluconate dehydrogenase (GND).

17. The method of claim 1, wherein the non-naturally occurring microbe expresses one or more heterologous $CO_2$ fixation pathway enzymes.

18. The method of claim 1, wherein the non-naturally occurring microbe is derived from *Corynebacterium*.

19. The method of claim 1, wherein the non-naturally occurring microbe is *Corynebacterium glutamicum*.

* * * * *

```
                      SEQUENCE LISTING

<160> NUMBER OF SEQ ID NOS: 11

<210> SEQ ID NO 1
<211> LENGTH: 2682
<212> TYPE: DNA
<213> ORGANISM: Moorella thermoacetica

<400> SEQUENCE: 1
atggttaatc tgacgatcga cggtcaacgt gttacggcgc ctgagggtat gacgatcttg      60
gaggttgcgc gtgagaacgg tatccacatt ccaacgctgt gtcatcaccc gaaactgcgt     120
ccgctgggct actgtcgtct gtgcctggtg gatatcgagg gtgcagcgaa gccgatgacc     180
gcgtgcaata ccccggtggc cgagggtatg gtgattcgca ccagcacccc ggtgatcgaa     240
gagatgcgca agggtatcat tgagatgttg ctgagcctgc atcctgagga ctgtctgacg     300
tgcgaaaagg cgggtaactg tcagctgcag gattgtgcat atacgtacgg cgtaaaacat     360
ggtgagctgc cggtcaagcg cgaagaatta ccggtgttga agaaaaccc gtttatcgtg      420 cgtgattaca acaagtgtat tgtctgtggt cgttgtgtgc gcgcgtgcca ggaagtgcaa     480
gttcagcgtg ttgtggacct ggtcggtaag ggtagcgcg cacgcgtcgg cgctaccaag     540
gccggtgctg aagttagcct ggaagagggc ggctgcgttt tctgcggcaa ttgcgtccaa     600
gtttgtccgg tgggtgcgct gaccgagaaa gccggcctgg gccagggtcg tgagtgggaa     660
ttcaaaaaag ttcgctcgat ctgtagctat tgcggtgtgg gctgcaatct gactctgtac     720
gtgaaggacg gtaaagtcgt taaggttcgc ggttatgaga cccggaagt aaacaacggt      780 tggctgtgtg ttaagggccg cttcggtttt gattacattc acaacccgga ccgtattacg     840
cgtccgctga ttcgcgaggg cgatcgtgag aaaggttatt tccgtgaggc gtcctgggaa     900
gaagcgctgg ccctggtgag ccagaaactg acccaaatca aaggttctta cggttccgaa     960
gcactgggtt ttctgtgcag cgccaagtgc acgaacgaag agaattacct gttgcaaaag    1020
ttagctcgtg gtgtgctcgg taccaataac gtcgatcatt gtgcacgcct gtgacactct    1080
tctacggttc aggtctgca ccaaacgttc ggcagcggtg ccatgaccaa tagcatcgcg     1140
gatattgcga gcgcggactg cattttttgtt atcggtagca acaccaccga aaatcacccg    1200
```

```
gttattgccc tgaaagtcaa agaggcagtc cgtcgtggtg cgcgtctgat cgtcgcggat    1260
cctcgccgta tcgagttggt caatttcagc tatctttggc tgcgccagaa gccgggtacc    1320
gacttggccc tgctgaatgg cctgttgcac gttatcatta agaagaact gtacgataaa    1380 gaattcatcg cacagcgtac cgaaggcttt gaggctttga actggcagt ggaagagtac    1440 actccggcaa aagtttccga ggtcaccggt gtgccggcag gcgacattat cgaagcggct    1500
cgcacctatg cgcgtggtcc atccagcacc attctgtatg cgatgggtat tacgcaacac    1560
attacgggca ccgcaaacgt gatggcatta gcgaatctgg cgatggcgtg cggccaggtt    1620
ggtaaggaag gcaacggcgt caacccgctg cgcggtcaat caaacgttca gggtgcgtgc    1680
gacatgggtg gcctgccgaa tgtcctcccg ggttatcaac cggttaccga cccgggtgtg    1740
cgtcacaagt tcagcgaaac ttggggtgtg ccggatctgc cgggtgagcc aggtctgacg    1800
ctgatggaga tgatggcagc ggcccaggag ggcaagttga agggtatgta tatcctgggt    1860
gaaaaccctg ttctgaccga tccagacgtg agccatgtta aagaggccct gaagaacctg    1920
gaattcttgg tcgtccaaga catctttctg acggaaaccg cacgcatggc tgatgttgtg    1980
ctgccgggtg cgagctttgc ggagaaagaa ggcacctta cttccaccga gcgtcgtgtg    2040
cagctgctgc ataaagcaat tgaaccgcct ggcgaggcgc gtccggattg gctgattctg    2100
aatgacctgt tgctgttgat gggctatccg cgcaaataca gcagcccggg tgagatcatg    2160
caagaaattg cgggcctgac cccgagctat gcgggtatca cctacgagcg tctggaggac    2220
aagggcctgc agtggccggt tctgagcctg gagcacccgg gtacgccggt cctgcaccgt    2280
gagaaattca gccgtggcta cggtcagttc caagttgtcc attaccgtcc accggcagag    2340
gaaccggacg aagagtaccc gtttctgttt accaccggcc gtaacctgta ccactatcac    2400
accgtcatct cgcgcaagag ccgcggtttg aagaaatgt gcccagcccc ggttgtcgag    2460
attaatgata acgatgccgc tcgcctgggc atccgtgagg gcgagatgat tgagattgtg    2520
agccgtcgcg gtaaggtccg tgttaaagcg ctggtgaccg accgtatccc tcgcggccaa    2580
gtgtttatga atttccattt ccacgaagcg gctgccaatc tgctgacgat tgctgcgctg    2640
gatccggtcg ctaagattcc gattatcaaa ccggttctgt aa                      2682
```

<210> SEQ ID NO 2
<211> LENGTH: 1095
<212> TYPE: DNA
<213> ORGANISM: Candida boidinii

<400> SEQUENCE: 2

```
atgaaaatcg ttctggtgct gtatgatgcc ggcaaacatg cggccgatga agaaaaactg     60
tacggctgca ccgaaaacaa actgggtatc gcaaattggc tgaaagatca gggccacgaa    120
ctgattacca cgagtgataa agaaggtgaa accagcgaac tggataaaca tatcccggat    180
gccgatatta tcattaccac gccgtttcac ccggcatata ttacgaaaga acgcctggat    240
aaagcaaaaa acctgaaact ggtggttgtg gcgggcgttg gtagtgatca tatcgatctg    300
gattacatta accagaccgg caagaaaatt agcgttctgg aagtgacggg tagcaatgtt    360
gtgtctgtgg cagaacacgt tgtgatgacc atgctggttc tggtgcgtaa ctttgttccg    420
gcgcatgaac agatcattaa tcacgattgg gaagtggcag cgatcgcgaa agatgcctat    480
gatattgaag gcaaaaccat cgcgacgatt ggcgccggtc gtattggtta ccgcgttctg    540
gaacgtctgc tgccgttcaa cccgaaagaa ctgctgtatt acgattatca ggccctgccg    600
aaagaagcag aagaaaaagt tggcgcgcgt cgcgtggaaa atatcgaaga actggtggcc    660
```

```
caggcagata ttgttaccgt gaacgcaccg ctgcatgcgg gcacgaaagg tctgatcaac      720
aaagaactgc tgagtaaatt caagaaaggc gcgtggctgg ttaataccgc acgcggtgcg      780
atttgtgttg ccgaagatgt tgcggcagcc ctggaaagcg gtcagctgcg tggttatggc      840
ggtgatgtgt ggttcccgca gccggcaccg aaagatcatc cgtggcgtga tatgcgcaac      900
aaatatggcg ccggtaatgc aatgaccccg cactacagcg gtaccacgct ggatgcgcag      960
acccgctatg ccgaaggcac gaaaaacatt ctggaatctt tctttaccgg taaattcgat     1020
taccgtccgc aggatatcat tctgctgaat ggcgaatatg tgacgaaagc gtacggtaaa     1080
cacgataaaa aataa                                                     1095

<210> SEQ ID NO 3
<211> LENGTH: 4719
<212> TYPE: DNA
<213> ORGANISM: Escherichia coli

<400> SEQUENCE: 3
ccggtttgct gatagttttc tttaccacca gcgcttctga gttacccagt tttgacgcca       60
gcaagaagac ttcaatcggc acctgttggc tggctgcaac cgctaacggg ctggaaccaa      120
ggttgccgat ttgcacgtcg ccagaagcca gcgcccgcac gatgctggct ccgctgtcaa      180
acttacgcca gtccacggtt gctccgcttt ctttagcaaa ggtgttgtcg gcctgagcca      240
cttttcgccg gttcggctgag gtttgatacg ccacggtgac gttcaccgcc tgtgcctgaa      300
aagcgatgaa tgccagtgcg gcaagaagtg tgtttcgcga tgaaattgcc atgattgtct      360
gctcccctgt cttgttatgg gagcagtatt caggaataaa acattcatt aaaagaatta      420 gtcgttatcg cacagatgat tttattctta gcaaaaaaac ggtgatgctg ccaacttact      480
gatttagtgt atgatggtgt ttttgaggtg ctccagtggc ttctgttttct atcagctgtc      540 cctcctgttc agctactgac ggggtggtgc gtaacggcaa aagcaccgcc ggacatcagc      600
gctatctctg ctctcactgc cgtaaaacat ggcaactgca gttcacttac accgcttctc      660
aacccggtac gcaccagaaa atcattgata tggccatgaa tggcgttgga tgccgggcaa      720
ctgcccgcat tatgggcgtt ggcctcaaca cgattttacg tcacttaaaa aactcaggcc      780
gcagtcggta acctcgcgca tacagccggg cagtgacgtc atcgtctgcg cggaaatgga      840
cgaacagtgg ggctatgtcg gggctaaatc gcgccagcgc tggctgtttt acgcgtatga      900
caggctccgg aagacggttg ttgcgcacgt attcggtgaa cgcactatgg cgacgctggg      960
gcgtcttatg agcctgatgt caccctttga cgtggtgata tggatgacgg atggctggcc     1020
gctgtatgaa tcccgcctga agggaaagct gcacgtaatc agcaagcgat atacgcagcg     1080
aattgagcgc ataacctga atctgaggca gcacctggca cggctgggac ggaagtcgct     1140
gtcgttctca aaatcggtgg agctgcatga caaagtcatc gggcattatc tgaacataaa     1200
acactatcaa taagttggag tcattaccta gaacgtaatt tacctgccgg aacttattca     1260
ctccgacaag aacttatccg tacaggagat taaaatgata aaacggacgt tattagcggc     1320
ggccattttt agcgcattgc ccgcttatgc cgggttaact tccattaccg cgggctacga     1380
ttttaccgat tattctggcg atcatggcaa ccgtaattta gcgtatgctg aactggtggc     1440
gaaagttgaa aacgcaacgc tgcttttta tctttcccag gggcgtcgtg attatgaaac     1500
tgaacatttc aatgccactc gcggtcaggg tgcggtctgg tataaatgga ataactggct     1560
gacaacccga acgggtattg cctttgcgga taatacgccg gtctttgccc gccaggattt     1620
```

```
tcgtcaggat attaacctgg ccctgttgcc aaaaacgctt ttcacgaccg gttatcgcta    1680
cactaaatat tacgatgatg tcgaagtcga tgcctggcaa ggcggcgtat cactctatac    1740
tggcccggtg atcaccagct accgctatac ccattatgac tccagcgatg caggtggtag    1800
ttatagcaat atgatttccg tcgtctgaa tgacccgcgc ggcactggtt atacgcaact     1860
atggctaagc cgcggaacag gcgcttacac ctatgactgg acgccagaaa cacgctacgg    1920
cagcatgaag agcgtcagtc tgcaacgtat tcaaccgctg actgagcaac ttaatctcgg    1980
gctgacggca ggtaaagtgt ggtacgacac cccaaccgat gattataacg gtctgcaact    2040
tgcagcccat ctgacctgga aattctgatt ccttctgccg cccgctatcc ggggcggcct    2100
tccctgccga ttagcccccc cctttcctct ttgttttccg accacattca ccggataaat    2160
tttattctcc agtgttatat actataggg ggtatgcatt gacatatagc ataccccct     2220 atagtatatt gcgtgcagat aatgaggtgc gaaatgccca gtactccgga agagaagaaa    2280
aaggtcctta ctcgagttcg tcgtattcga gggcagattg atgctctgga acggtcgctg    2340
gagggtgatg ccgaatgccg tgccatactc caacagatcc ctgccgttcg gggcgcggct    2400
aatgggctga tggcagaagt gcttgaaagc catatccggg aaacgtttga ccgaaatgac    2460
tgctacagcc gcgaagtcag ccaatccgtt gacgacacta ttgaactggt tcgagcctat    2520
cttaaatagc tgaatctatt accatattga ggaagagcga gagtgaaat cacgtgctgc     2580 cgttgcattt gctcccggta aaccgctgga aatcgttgaa attgacgttg caccaccgaa    2640
aaaaggtgaa gtgctgatta agtcaccca taccggcgtt tgccataccg acgcatttac    2700
cctctccggg gatgacccgg aaggtgtatt cccggtggtt ctcggtcacg aaggggccgg    2760
cgttgtggtt gaagtcggtg aaggcgtaac cagcgtcaaa cctggcgacc atgtgatccc    2820
gctttacacc gcggagtgcg gcgagtgtga gttctgtcgt tctggcaaaa ctaacctctg    2880
tgttgcggtt cgcgaaaccc agggtaaagg cttgatgcca gacggcacca cccgttttc     2940 ttacaacggg cagccgcttt atcactacat gggatgctca acattcagtg aatacaccgt    3000
ggtcgcggaa gtgtctctgg ccaaaattaa tccagaagca aaccatgaac acgtctgcct    3060
gctgggctgt ggcgtgacca ccggtattgg cgcggtgcac aacacagcta aagtccagcc    3120
aggtgattct gttgccgtgt tggtcttgg cgcgattggt ctggcagtgg ttcagggcgc     3180
gcgtcaggcg aaagcgggac ggattatcgc tatcgatacc aacccgaaga aattcgatct    3240
ggctcgtcgc ttcggtgcta ccgactgcat taacccgaat gactacgaca aaccgattaa    3300
agatgtcctg ctggatatca acaaatgggg tatcgaccat acctttgaat gcatcggtaa    3360
cgtcaacgtg atgcgtgcgg cgctggaaag tgcgcaccgc ggctggggtc agtcggtgat    3420
catcggggta gcaggtgccg gtcaggaaat ctccacccga ccattccagt ggtcaccgg    3480 tcgcgtatgg aaaggttccg cgtttggcgg cgtgaaaggt cgttcccagt taccgggtat    3540
ggttgaagat gcgatgaaag gtgatatcga tctggaaccg tttgtcacgc ataccatgag    3600
ccttgatgaa attaatgacg ccttcgacct gatgcatgaa ggcaaatcca ttcgaaccgt    3660
aattcgttac tgatttcccg caggtatacc ccgtccactt cagacggggt tcttaatact    3720
ctccctgggc agccgtccgg gggattaacc gtgagataat gactgatgga actcattgaa    3780
aaacatgcca gctttggcgg ctggcaaaat gtgtatcggc attattccca atcactgaaa    3840
tgtgaaatga atgtcggcgt ctatctccca ccaaaagccg cgaatgaaaa attgccggtg    3900
ttgtactggc tttcaggcct gacttgcaac gagcagaatt tcattactaa atcggggatg    3960
cagcgttacg cggctgagca caacattatt gttgttgcgc cggacaccag tccgcgaggc    4020
```

```
agtcatgtcg cagatgctga ccgttacgat ctcgggcaag gtgccgggtt ttacctgaac    4080
gcgacgcaag cgccgtggaa tgaacattac aaaatgtatg actatatccg caacgagctg    4140
ccggatttag tgatgcatca ttttccggca acggccaaaa agtctatctc tggtcattct    4200
atgggcgggc tggcgcgct ggtgctggcg ttacgtaacc cagatgaata tgtcagcgtc    4260
tcggcgtttt cgcccattgt ctccccatcg caagtgccgt ggggacagca agcctttgct    4320
gcatatcttg ctgaaaataa agatgcctgg ttggattacg acccggtgag tcttatttca    4380
caaggtcaac gcgttgcgga atcatggtt gatcaggggt tgagtgatga tttttacgca    4440
gaacagctgc ggactccaaa tcttgaaaag atctgccagg agatgaatat caagacgtta    4500
atccgttatc acgagggtta tgatcacagc tattattttg tctccagttt tattggcgag    4560
catattgcct accacgccaa taaactgaat atgcgttgat aatagtgcac gactgccgga    4620
tgcggcgtga acgccttatc cggcctacac ttcgcccgta aaccgtagga agatctgatt    4680
ggcaaacgca tcgccgtacc gtttatctct accacccac                          4719
```

<210> SEQ ID NO 4
<211> LENGTH: 14
<212> TYPE: PRT
<213> ORGANISM: Moorella thermoacetica

<400> SEQUENCE: 4

His Ser Ser Thr Val Ala Gly Leu Ala Thr Thr Phe Gly Ser
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

His Ser Ser Thr Val Ala Gly Leu His Gln Thr Phe Gly Ser
1               5                   10

<210> SEQ ID NO 6
<211> LENGTH: 70
<212> TYPE: DNA
<213> ORGANISM: Artificial Sequence
<220> FEATURE:
<223> OTHER INFORMATION: Synthetic

<400> SEQUENCE: 6
atatagcata ccccctata gtatattgcg tgcagataat gaggtgcgaa attccgggga    60
tccgtcgacc                                                          70

<210> SEQ ID NO 7
<211> LENGTH: 70
<212> TYPE: DNA
<213> ORGANISM: Artificial Sequence
<220> FEATURE:
<223> OTHER INFORMATION: Synthetic

<400> SEQUENCE: 7
tgtaggccgg ataaggcgtt cacgccgcat ccggcagtcg tgcactatta tgtaggctgg    60
agctgcttcg                                                          70

<210> SEQ ID NO 8

<211> LENGTH: 2682
<212> TYPE: DNA
<213> ORGANISM: Moorella thermoacetica

<400> SEQUENCE: 8

```
atggttaacc tgaccattga cggacaaagg gttacggctc cagagggcat gaccatcctg      60
gaggtggccc gggaaaatgg tatccatatc cccaccctgt gccaccatcc aaagttgcgg     120
cccctggggt attgccgtct gtgcctggtc gacatcgagg gcgccgcaaa acccatgacg     180
gcctgcaata cgccggtcgc cgagggtatg gtgatccgga ccagcacgcc tgttatagag     240
gagatgcgca aggtattat tgaaatgctt ttaagcctcc acccggagga ctgcctgacc     300
tgcgaaaaag caggtaactg ccagctccag gattgcgcct acacttacgg tgtaaagcat     360
ggcgaactgc cagtaaaacg cgaggaattg cccgttttga aggaaaatcc cttcattgtg     420
cgggattata ataaatgtat cgtttgcggc cgttgcgtcc cgcctgcca ggaggtgcag     480
gtccagaggg tcgtggacct ggtgggtaaa ggcagcgccg cccggtgggg ggcgacgaag     540
gccggagcgg aagtaagcct ggaagaaggg ggctgcgtct tttgcggtaa ctgtgtccag     600
gtctgcccgg tgggagctct gacgagaag gccggcctgg gccagggccg cgagtgggag     660
ttcaaaaaag tccgcagtat ttgttcttac tgcggcgtgg gttgtaatct caccctttat     720
gtaaaagatg gtaaggtggt aaaagttagg ggttacgaaa accctgaggt aaacaacggc     780
tggctgtgcg taaaaggccg cttggttt gactatattc acaatcctga caggataacc     840
aggccgttga tccgggaggg agataggaa aaaggctatt ccgggaggc ttcctgggaa     900
gaagctttag cccttgtatc ccagaaatta actcagatta aaggcagcta cggctctgaa     960
gctctgggct ttctttgttc agctaaatgt accaatgaag agaattatct cttacaaaag    1020
ctggcccggg gggtactggg caccaataat gttgatcact gtgctcgcct ctgacacagc    1080
tctaccgtag caggtctgct cgctacattt ggaagcggtg caatgaccaa ttctatcgct    1140
gacatcgcca gcgcagattg tatctttgtc attggcagca atacaaccga gaaccatcct    1200
gttattgccc ttaaagtaaa agaagctgtc cgtcgtggag ccaggctcat tgttgctgat    1260
ccccggcgta ttgaactggt gaacttcagt tacttgtggt taagacaaaa acccggaaca    1320
gatcttgctc tgctgaatgg actgcttcat gtaatcatca aggaagagct ttatgacaaa    1380
gaatttattg cccagaggac ggaaggtttt gaggctctaa aacttgccgt agaggagtat    1440
acaccagcaa aggtgtcaga agttacaggt gttccggcag gcgatattat cgaggcagca    1500
aggacttatg cccgggggtcc gagctctact attttgtacg caatgggaat aacccagcat    1560
ataactggta cggccaacgt gatggccctg gccaacctgg ccatggcctg tggtcaggtc    1620
ggtaaagaag gtaacggcgt aaatcccctg cgggggcaga gcaatgtcca gggtgcctgc    1680
gatatgggtg gattacccaa tgtattaccg ggataccaac cagtaacaga tccgggggtt    1740
cgccataaat ttagcgaaac ctggggggta ccggacttac ccggagaacc tggcctgaca    1800
ttaatggaga tgatggcggc agcccaagaa ggcaaattga aagggatgta tattttagga    1860
gaaaaccctg tcttgactga tccagatgtc tcccatgtaa agaggcgtt aaagaacctg    1920
gagtttctgg tggtacagga tattttttg acggagacag ccaggatggc ggatgttgtt    1980
ttacctggag cttcctttgc ggaaaaggaa ggtacctta ccagtacgga gcgccgggtg     2040
cagcttttgc ataaagccat tgaacctccc ggtgaagcac ggccggattg cttattttta     2100
aacgatttgt tgctgttaat gggatatccg cggaaatatt cgtcgcctgg ggagataatg     2160
caggagatag cagggttaac tcccagctat gcgggtataa cttatgagcg cctggaagat     2220
```

```
aaagggttac agtggccggt gctttccctc gaacatccgg gtacacccgt tctccatcgg    2280
gaaaaattta gcagaggtta tgggcagttc caggtagtgc attaccggcc gccggccgaa    2340
gaacctgatg aagagtaccc gttcttattt accactggca ggaatttgta tcactatcat    2400
actgttattt cccgtaagtc caggggctg aagagatgt gtcctgctcc tgtggtggag    2460
attaatgata acgatgcagc ccgtttgggt atacgggaag gagaaatgat tgagattgtt    2520
tcccgacgtg gtaaagtaag ggttaaagca ttggttacgg atcgcatacc ccggggccag    2580
gtatttatga atttccattt ccatgaagca gcagccaacc tgcttacaat tgctgccctg    2640
gatccggttg ctaaaatacc gattataaaa cctgtgctgt ag                      2682
```

<210> SEQ ID NO 9
<211> LENGTH: 2184
<212> TYPE: DNA
<213> ORGANISM: Moorella thermoacetica

<400> SEQUENCE: 9

```
atgctgattc gccgcttccg tgcttgtccg cgtgatcgta cgcaacgtcg tgataccgct     60
ctgggtgaag tcgtcttttc aacctggggt ggcaaagtgg ttgatcatcg cggcggtccg    120
agtggcggtg gcccgtcctg gcgggtgaa tttggtggcc gtcagctgaa agccttcatt    180
ggctgggacg tctggtcgt gacggatccg gcagtggacc tgctggcagc actgcaagct    240
tattaccagg cggttcaagg cgaaagctgc ggtcgctgtg tgccgtgccg tgttggcacc    300
cgtgtcattt ataacgtgct ggttcgtatc gcaggtggcg aaggtctgcc gagcgatctg    360
gacctgctgc gtcgcgtggc gtggatcgtt cgcgatggct ctctgtgcga actgggccag    420
gcaggtgcta aagcggtgct ggatttctg gactattaca gcgaagcact gcgcccgttc    480
ctggaagatt ctggccgtgt tgcgggtggc cagcgtcgcc cgggtccggg tggccgtgtc    540
caagtgctgg catcaggtcg tgttctggtc ggtaatgatc gtggtaaagg tgcagctgca    600
gcatcgccgg cagctggtct gacctataaa ccgtttgtga cggcaccgtg tctgaaacgt    660
tgcccggcac atctggatat tccggcctat attgatgcaa tcaaagacgg tcgttacgaa    720
gaatccctgg cgattatccg tcagcgtacc gcactggcag gcgtgctggg tcgcgtgtgt    780
gttcacccgt gcgaagaaaa actgtcgtcgc ggcaatgttg atgaaccgct ggcaatccgc    840
ggtctgaaac gttttgtcgc tgactacgaa gtgaaacgtg tcgtcgccc ggtcgcagtg    900 tgtggtggca acctgttcac cggtccgtgg cgtccggctg gtcaggcggg tggcgaagaa    960
accacggctg ttacgtcagg caagaaagtg gcgattatcg gtgcaggtcc ggcaggtctg   1020
tcggcagcat atcaactggc aggtcgcggt tacaaagtga ccatttttga agctctgccg   1080
gtcgcgggtg gcatgctggc agtgggtatt ccgagttatc gcctgccgcg tgatatcctg   1140
gccggcgaaa ttgaagctat caaagcgctg gtgtgaccca tcaacctgaa tacgcgcgtt   1200
ggcgtcgatg tgaccatgga ccagctgcaa cgtgattatg acgccgtttt cattgcaacg   1260
ggtctgcatg ctagctctcg tatgggcgtg gcgggtgaag atgaaggcta cggtggcttt   1320
atcccgggtg ttaaattcct gcgcgatctg aacctggacc gttgcccgtc tctggaaggc   1380
aaagttgtcg ccgtggttgg tggcggtaat gtggcaatgg attgtgcacg tagtgcactg   1440
cgtcgcggtg cccgtgaagt tcatctgatt tatcgtcgct cccgcgcaga aatgccggct   1500
cacgcaaccg aagtgcgtga tgccgaagca gaaggcgtga tttaccactt tctggttaac   1560
ccgacggctc tggtcgcgga aaaaggcaat atcaagggta tgcagtgcgt tcgtatgaaa   1620
```

```
ctgggtgaac cggatgacag cggtcgtcgc cgtccggttc cggtcccggg taccgaattt    1680
ttcctgccgt gtgatattgt cgtgccggcg atcggccaag cagctgatct gtcttttctg    1740
gacggtcgca ttgaagtggg caaacgtggt accatctcag tcgatccggt gaccctggct    1800
acgtcggttc cgggcgtctt cgcgggcggt gacattgttc tgggtgcccg cacggttgtc    1860
gaagctgttg cacagggtaa tcgtgcagca gtcagtatcg atcagtatct gcgtcaaggt    1920
accacgtccc cgaccgtgga agatgaactg gacgcctggc tggaaaaagt gggcgtttat    1980
gatccggaag aagacgtcgg tatttacggc ggtcgtccgc gtcaggcaga acgtgtggca    2040
ccgctggcag aacgcgtgaa agattttcgt gaagttgaag gcggttttga cttctacgcg    2100
ggccgcgccg aagcagaacg ttgcctgcgt tgttatcgtg tcggtatgat ggtgctggcg    2160
ggcgaaggcg aatccaatgg ctga                                          2184
```

<210> SEQ ID NO 10
<211> LENGTH: 2184
<212> TYPE: DNA
<213> ORGANISM: Moorella thermoacetica

<400> SEQUENCE: 10

```
atgctgattc gccgcttccg tgcttgtccg cgtgatcgta cgcaacgtcg tgataccgct      60
ctgggtgaag tcgtcttttc aacctggggt ggcaaagtgg ttgatcatcg cggcggtccg     120
agtggcggtg gccgtcctg gcgggtgaa tttggtggcc gtcagctgaa agccttcatt      180
ggctgggacg gtctggtcgt gacggatccg gcagtggacc tgctggcagc actgcaagct     240
tattaccagg cggttcaagg cgaaagctgc ggtcgctgtg tgccgtgccg tgttggcacc     300
cgtgtcattt ataacgtgct ggttcgtatc gcaggtggcg aaggtctgcc gagcgatctg     360
gacctgctgc gtcgcgtggc gtggatcgtt cgcgatggct ctctgtgcga actgggccag     420
gcaggtgcta aagcggtgct ggattttctg gactattaca gcgaagcact cgcccgttc      480 ctggaagatt ctgccgtgt tgcgggtggc cagcgtcgcc cgggtccggg tggccgtgtc     540
caagtgctgg catcaggtcg tgttctggtc ggtaatgatc gtggtaaagg tgcagctgca     600
gcatcgccgg cagctggtct gacctataaa ccgtttgtga cggcaccgtg tctgaaacgt     660
tgcccggcac atctggatat ccggcctat attgatgcaa tcaaagacgg tcgttacgaa     720
gaatccctgg cgattatccg tcagcgtacc gcactggcag cgtgctgggg tcgcgtgtgt     780
gttcacccgt gcgaagaaaa ctgtcgtcgc ggcaatgttg atgaaccgct ggcaatccgc     840
ggtctgaaac gttttgtcgc tgactacgaa gtgaaacgtg tcgtcgccc ggtcgcagtg     900 tgtggtggca acctgttcac cggtccgtgg cgtccggctg gtcaggcggg tggcgaagaa     960 accacgctc ttacgtcagg caagaaagtg gcgattatcg tgcaggtcc ggcaggtctg    1020 tcggcagcat atcaactggc aggtcgcggt tacaaagtga ccattttga agctctgccg    1080 gtcgcgggtg gcatgctggc agtgggtatt ccgagttatc gcctgccgcg tgatatcctg    1140
gccggcgaaa ttgaagctat caaagcgctg gtgtgacca tcaacctgaa tacgcgcgtt    1200
ggcgtcgatg tgaccatgga ccagctgcaa cgtgattatg acgccgtttt cattgcaacg    1260
ggtctgcatg ctagctctcg tatgggcgtg cgggtgaag atgaaggcta cggtggcttt    1320
atcccgggtg ttaaattcct cgcgatctg aacctggacc gttgccgtc tctggaaggc    1380 aaagttgtcg ccgtggttgg tggcggtaat gtgcaatgg attgtgcacg tagtgcactg    1440
cgtcgcggtg cccgtgaagt tcatctgatt tatcgtcgct cccgcgcaga aatgccggct    1500
cacgcaaccg aagtgcgtga tgccgaagca gaaggcgtga tttaccactt tctggttaac    1560
```

```
ccgacggctc tggtcgcgga aaaaggcaat atcaagggta tgcagtgcgt tcgtatgaaa    1620
ctgggtgaac cggatgacag cggtcgtcgc cgtccggttc cggtcccggg taccgaattt    1680
ttcctgccgt gtgatattgt cgtgccggcg atcggccaag cagctgatct gtcttttctg    1740
gacggtcgca ttgaagtggg caaacgtggt accatctcag tcgatccggt gaccctggct    1800
acgtcggttc cgggcgtctt cgcgggcggt gacattgttc tgggtgcccg cacggttgtc    1860
gaagctgttg cacagggtaa tcgtgcagca gtcagtatcg atcagtatct gcgtcaaggt    1920
accacgtccc cgaccgtgga agatgaactg gacgcctggc tggaaaaagt gggcgtttat    1980
gatccggaag aagacgtcgg tatttacggc ggtcgtccgc gtcaggcaga acgtgtggca    2040
ccgctggcag aacgcgtgaa agattttcgt gaagttgaag gcggttttga cttctacgcg    2100
ggccgcgccg aagcagaacg ttgcctgcgt tgttatcgtg tcggtatgat ggtgctggcg    2160
ggcgaaggcg aatccaatgg ctga                                           2184
```

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

```
His Ser Ser Thr Val Ala Gly Leu Leu Ala Thr Phe Gly Ser
1               5                   10
```